(12) United States Patent
Ehring et al.

US007728034B2

(10) Patent No.: US 7,728,034 B2
(45) Date of Patent: Jun. 1, 2010

(54) TREATING NEUROLOGICAL DISORDERS USING SELECTIVE ANTAGONISTS OF PERSISTENT SODIUM CURRENT

(75) Inventors: George R. Ehring, Huntington Beach, CA (US); Joseph S. Adorante, Irvine, CA (US); Larry A. Wheeler, Irvine, CA (US); Thomas Malone, Irvine, CA (US); Scott M. Whitcup, Laguna Hills, CA (US)

(73) Assignee: Allergan, Inc., Irvine, CA (US)

( * ) Notice: Subject to any disclaimer, the term of this patent is extended or adjusted under 35 U.S.C. 154(b) by 1184 days.

(21) Appl. No.: 11/326,264

(22) Filed: Jan. 5, 2006

(65) Prior Publication Data

US 2006/0106103 A1    May 18, 2006

Related U.S. Application Data

(62) Division of application No. 10/928,949, filed on Aug. 27, 2004, now Pat. No. 7,060,723.

(60) Provisional application No. 60/498,902, filed on Aug. 29, 2003.

(51) Int. Cl.
| | |
|---|---|
| *A01N 37/00* | (2006.01) |
| *A61K 31/21* | (2006.01) |
| *A01N 37/18* | (2006.01) |
| *A61K 31/16* | (2006.01) |
| *A01N 35/00* | (2006.01) |
| *A61K 31/12* | (2006.01) |

(52) U.S. Cl. ........................ 514/506; 514/510; 514/613; 514/675; 514/678; 514/679; 514/680
(58) Field of Classification Search .................. 514/646, 514/506, 510, 613, 675, 678, 679, 680
See application file for complete search history.

(56) References Cited

U.S. PATENT DOCUMENTS

| | | | |
|---|---|---|---|
| 5,661,035 | A | 8/1997 | Tsien et al. |
| 5,688,830 | A | 11/1997 | Berger et al. |
| 5,922,746 | A | 7/1999 | Adorante |
| 6,342,379 | B1 | 1/2002 | Tsien et al. |
| 6,479,498 | B1 | 11/2002 | Marquess et al. |
| 6,646,012 | B2 | 11/2003 | Choi et al. |
| 6,686,193 | B2 | 2/2004 | Maher et al. |
| 6,699,493 | B2 | 3/2004 | Wong |
| 6,726,918 | B1 | 4/2004 | Wong et al. |
| 6,756,400 | B2 | 6/2004 | Chinn et al. |
| 2002/0077297 | A1 | 6/2002 | Adorante et al. |
| 2004/0054374 | A1 | 3/2004 | Weber et al. |
| 2004/0137059 | A1 | 7/2004 | Nivaggioli et al. |

FOREIGN PATENT DOCUMENTS

EP      1 182 193 A1    2/2002

OTHER PUBLICATIONS

Agrawal, Newton et al., *Increased Persistent Sodium Currents in Rat Entorhinal Cortex Layer V Neurons in a Post-Status Epilepticus Model of Temporal Lobe Epilepsy*, 44(12) Epilepsia 1601-1604 (2003).
Ahern, Gerard P. et al., *Induction of Persistent Sodium Current by Exogenous and Endogenous Nitric Oxide*, 275(37) J. Biol. Chem. 28810-28815 (2000).
Anger, Thorsten et al., *Medicinal Chemistry of Neuronal Voltage-Gated Sodium Channel Blockers*, 44(2) J. Med. Chem. 115-137 (2001).
Barbato, Joel E. & Edith Tzeng, *Nitric Oxide and Arterial Disease* 40(1) J. Vasc. Surg. 187-193 (2004).
Barber, Alistair J., *A New View of Diabetic Retinopathy: A Neurodegenerative Disease of the Eye*, 27(2) Prog. Neuropsychopharmacol. Biol. Psychiatry. 283-290 (2003).
Barnham, Kevin J. et al., *Neurogegenerative diseases and Oxidative Stress*, 3(3) Nat. Rev. Drug. Dis. 205-214 (2004).
Bass, B. L., *RNA Interference. The Short Answer*, 411(6836) Nature 428-429 (2001).
Bolanos, Juan P. & Angeles Almeida, *Roles of Nitric Oxide in Brain Hypoxia-Ischemia*, 1411(2-3) Biochim. Biophys. Acta. 415-436 (1999).
Bonanni, Paolo et al., *Generalized Epilepsy with Febrile Seizures Plus (GEFS+): Clinical Spectrum in Seven Italian Families Unrelated to SCN1A, SCN1B, and GABRG2 Gene Mutations*, 45(2) Epilepsia 149-158 (2004).
Brismar, Tom, *Abnormal Na-Currents in Diabetic Rat Nerve Nodal Membrane*, 10(Suppl. 2) Diabet. Med. 110S-112S (1993).
Broadbent, H. Smith et al., *Quinoxalines. I. Preparation and Stereochemistry of Decahydroquinoxalines*, 82(1) J. Amer. Chem. Soc. 189-193 (1960).
Catterall, William A., *From Ionic Currents to Molecular Mechanism: The Structure and Function of Voltage-gated Sodium Channels*, 26(1) Neuron 13-25 (2000).
Ceulemans, Berten P. G. M. et al., *Clinical Correlations of Mutations in the SCN1A Gene: from Febrile Seizures to Severe Myoclonic Epilepsy in Infancy*, 30(4) Pediatr. Neurol. 236-243 (2004).
Craner, Matthew J. et al., *Co-Localization of Sodium Channel $Na_v1.6$ and the Sodium-Calcium Exchanger at Sites of Axonal Injury in the Spinal Cord in EAE*, 127(2) Brain 294-303 (2004).
Craner, Matthew J. et al., *Molecular Changes in Neurons in Multiple Sclerosis: Altered Axonal Expression of $Na_v1.2$ and $Na_v1.6$ Sodium Channels and Na+/Ca2+ Exchanger*, 101(21) Proc. Natl. Acad. Sci. U.S.A. 8168-8173 (2004).
Crill, Wayne E., *Persistent Sodium Current in Mammalian Central Neurons* 58 Annu. Rev. Physiol. 349-362 (1996).
Current Protocols in Molecular Biology (Frederick M. Ausubel et al., eds., John Wiley & Sons, 2004).

(Continued)

*Primary Examiner*—Yong S Chong
(74) *Attorney, Agent, or Firm*—Dean G. Stathakis; Joel B. German; Allergan, Inc.

(57) ABSTRACT

The present invention provides methods of treating neurological disorders in a mammal by administering to the mammal an effective amount of a selective persistent sodium channel antagonist that has at least 20-fold selectivity for persistent sodium current relative to transient sodium current.

46 Claims, 7 Drawing Sheets

OTHER PUBLICATIONS

Do, Michael Tri H. & Bruce P. Bean, *Subthreshold Sodium Currents and Pacemaking of Subthalamic Neurons: Modulation by Slow Inactivation*, 39(1) Neuron 109-120 (2003).

Elbashir, Sayda M. et al., *Duplexes of 21—nucleotide RNAs Mediate RNA Interference in Cultured Mammalian Cells*, 411(6836) Nature 494-498 (2001).

Fukuma, Goryu et al., *Mutations of Neuronal Voltage-Gated Na+ Channel Alpha 1 Subunit Gene SCN1A in Core Severe Myoclonic Epilepsy in Infancy(SMEI) and in Borderline SMEI(SMEB)*, 45(2) Epilepsia 140-148 (2004).

Gardner, Thomas W. et al., *Diabetic Retinopathy: More than Meets the Eye*, 47(Suppl. 2) Surv. Ophthalmol. S253-S262 (2002).

Garthwaite, Gita et al., *Mechanisms of Ischaemic Damage to Central White Matter Axons: A Quantitative Histological Analysis Using Rat Optic Nerve*, 94(4) Neuroscience 1219-1230 (1999).

Garthwaite, Gita et al., *Nitric Oxide Toxicity in CNS White Matter: An in Vitro Study Using Rat Optic Nerve*, 109(1) Neuroscience 145-155 (2002a).

Garthwaite, Gita et al., *Soluble Guanylyl Cyclase Activator YC-1 Protects White Matter Axons From Nitric Oxide Toxicity and Metabolic Stress, Probably Through Na (+) Channel Inhibition*, 61(1) Mol. Pharmacol. 97-104 (2002b).

GenBank database (National Institutes of Health, National Library of Medicine, http://www.ncbi.nlm.nih.gov/).

Ghofrani, Hossein A. et al., *Nitric Oxide Pathway and Phosphodiesterase Inhibitors in Pulmonary Arterial Hypertension*, 43(12 Suppl. S) J. Am. Coll. Cardiol. 68S-72S (2004).

Goldin, Alan L., *Diversity of Mammalian Voltage-gated Sodium Channels*, 868 Ann. N.Y. Acad. Sci. 38-50 (1999).

Gonzalez, Jesus E. & Michael P. Maher, *Cellular Fluorescent Indicators and Voltage/Ion Probe Reader(VIPR) Tools for Ion Channel and Receptor Drug Discovery*, 8(5-6) Receptors Channels 283-295, (2002).

Gonzalez, Jesus E. & Roger Y. Tsien, *Improved Indicators of Cell Membrane Potential That Use Fluorescence Resonance Energy Transfer* 4(4) Chem. Biol. 269-277 (1997).

Goodman & Gilman's The Pharmacological Basis of Therapeutics (Joel G. Hardman et al., eds., McGraw-Hill Professional, 10$^{th}$ ed. 2001).

Hammarström, Anna H. K. & Peter W. Gage, *Oxygen-sensing Persistent Sodium Channels in Rat Hippocampus*, 529(1) J. Physiol. 107-118 (2000).

Hammarström, Anna K. M. & Peter W. Gage, *Hypoxia and Persistent Current*, 31 (3) Eur. Biophys. J. 323-330 (2002).

Hammarström, Anna K. M. & Peter W. Gage, *Nitric Oxide Increases Persistent Sodium Current in Rat Hippocampal Neurons*, 520(2) J. Physiol. 451-461 (1999).

Handbook of Pharmaceutical Excipients (Raymond C. Rowe et al., APhA Publications, 4$^{th}$ edition 2003).

Heller, *Biodegradable Polymers in Controlled Drug Delivery* (CRC Critical Reviews in Therapeutic Drug Carrier Systems, vol. 1. CRC Press, 1987).

Imaging Neurons: A Laboratory Manual (Rafael Yuste, et al., eds., Cold Spring Harbor Laboratory Press, 2000).

Jayasena, Sumedha D., *Aptamers: An Emerging Class of Molecules That Rival Antibodies in Diagnostics*, 45(9) Clin. Chem. 1628-1650 (1999).

Johnson, Iain D., *Fluorescent Probes for Living Cells* 30(3) Histochem. J. 123-140 (1998).

Ju, Yue-Kun et al., *Hypoxia Increases Persistent Sodium Current in Rat Ventricular Myocytes*, 497(2) J. Physiol. 337-347 (1996).

Kamiya, Kazusaku et al., *A Nonsense Mutation of the Sodium Channel Gene SCN2A in a Patient with Intractable Epilepsy and Mental Decline*, 24(11) J. Neurosci. 2690-2698 (2004).

Karabinos, Anton et al., *Essential Roles for Four Cytoplasmic Intermediate Filament Proteins in Caenorhabditis elegans Development*, 98(14) Proc. Natl. Acad. Sci. USA 7863-7868 (2001).

Klein, Joshua P. et al., *Dysregulation of Sodium Channel Expression in Cortical Neurons in a Rodent Model of Absence Epilepsy*, 1000(1-2) Brain Res. 102-109 (2004).

Kohling, Rudiger, *Voltage-gated Sodium Channels in Epilepsy*, 43(11) Epilepsia 1278-1295 (2002).

Lieth, Erich et al., *Retinal Neurodegeneration: Early Pathology in Diabetes*, 28(1) Clin. Experiment. Ophthalmol. 3-8 (2000).

Lipton, Peter, *Ischemic Cell Death in Brain Neurons*, 79(4) Physiol. Rev. 1431-1568 (1999).

Lossin, Christoph et al., *Molecular Basis of an Inherited Epilepsy* 34(6) Neuron 877-84 (2002).

Magistretti, Jacopo & Angel Alonso, *Biophysical Properties and Slow-voltage Dependent Inactivation of a Sustained Sodium Current in Entorhinal Cortex Layer-II Principal Neurons: A Whole-Cell and Single-Channel Study* 114(4) J. Gen. Physiol. 491-509 (1999).

Maier, Sebastian K. G. et al., *An Unexpected Requirement for Brain-Type Sodium Channels for Control of Heart Rate in the Mouse Sinoatrial Node*, 100(6) Proc. Natl. Acad. Sci. U. S. A. 3507-3512 (2003).

Maier. Sebastian K. G. et al., *Distinct Subcellular Localization of Different Sodium Channel Alpha and Beta Subunits in Single Ventricular Myocytes from Mouse Heart*, 109(11) Circulation 1421-1427 (2004).

Maltsev, Victor A. et al., *Novel, Ultraslow Inactivating Sodium Current in Human Ventricular Cardiomyocytes*, 98(23) Circulation 2545-2552 (1998).

Meisler, Miriam H., et al., *Mutations of Voltage-gated Sodium Channels in Movement Disorders and Epilepsy*, 241 Novartis Found. Symp. 72-81 (2002).

Miyasaka, Nobuyuki & Yukio Hirata, *Nitric Oxide and Inflammatory Arthritides*, 61(21) Life Sci. 2073-2081 (1997).

Molecular Cloning A Laboratory Manual (Joseph Sambrook & David W. Russell eds., Cold Spring Harbor Laboratory Press, 3$^{rd}$ ed. 2001).

Moro, María A. et al., *Role of Nitric Oxide after Brain Ischaemia*, 36(3-4) Cell Calcium 265-275 (2004).

Mulrennan, Siobhan A. & Anthony E. Redington, *Nitric Oxide Synthase Inhibition: Therapeutic Potential in Asthma*, 3(2) Treat. Respir. Med. 79-88 (2004).

Novakovic, Sanja D. et al., *Regulation of Na+ Channel Distribution in the Nervous System*, 24(8) Trends Neurosci. 473-478 (2001).

Panahian, Nariman et al., *Attenuated Hippocampal Damage After Global Cerebral Ischemia in Mice Mutant in Neuronal Nitric Oxide Synthase*, 72(2) Neuroscience 343-354 (1996).

Pharmaceutical Dosage Forms and Drug Delivery Systems (Howard C. Ansel et al., eds., Lippincott Williams & Wilkins Publishers, 7$^{th}$ ed. 1999).

Prabhakar, Sharma S., *Role of Nitric Oxide in Diabetic Nephropathy*, 24(4) Semin. Nephrol. 333-344 (2004).

Quasthoff, Stefan, *The Role of Axonal Ion Conductances in Diabetic Neuropathy: A Review*, 21(10) Muscle Nerve 1246-1255 (1998).

Ragsdale, David S. & Avoli, Massimo, *Sodium Channels as Molecular Targets for Antiepileptic Drugs*, 26(1) Brain Res. Brain Res. Rev. 16-28 (1998).

Remington: The Science and Practice of Pharmacy (Alfonso R. Gennaro ed., Lippincott, Williams & Wilkins, 20$^{th}$ ed. 2000).

Ricciardolo, Fabio L. M. et al., *Nitric Oxide in Health and Disease of the Respiratory System*, 84(3) Physiol. Rev. 731-765 (2004).

Sakmann, Bert & Erwin Neher, Single Channel Recording (Plenum Press, 2$^{nd}$ ed. 1995).

Segal, Michael M., *Sodium Channels and Epilepsy Electrophysiology*, 241 Novartis Found. Symp. 173-180 (2002).

Shih, Tsung-Ming et al., *High-level Expression and Detection of Ion Channels in Xenopus Oocytes*, 529-556 (Methods in Enzymology: Ion Channels Part B, vol. 293, P. Michael Conn ed., Academic Press 1998).

Spadoni, Francesca et al., *Lamotrigine Derivatives and Riluzole Inhibit INa,P in Cortical Neurons*, 13(9) Neuroreport. 1167-1170 (2002).

Spampanato, J. et al., *Generalized Epilepsy with Febrile Seizures Plus Type 2 Mutation W1204R Alters Voltage-Dependent Gating of Na(V) 1.1 Sodium Channels*, 116(1) Neuroscience 37-48 (2003).

Splawski, Igor et al., *Variant of SCN5A Sodium Channel Implicated in Risk of Cardiac Arrhythmia*, 297 Science 1333-1336 (2002).

Stefani, Alessandro et al., *Differential Inhibition by Riluzole, Lamotrigine, and Phenytoin of Sodium and Calcium Currents in Cortical Neurons: Implications for Neuroprotective Strategies*, 147(1) Exp. Neurol. 115-122 (1997).

Strijbos, Paul J. et al., *Vicious Cycle Involving Na$^+$ Channels, Glutamate Release, and NMDA Receptors Mediates Delayed Neurodegeneration Through Nitric Oxide Formation*, 16(16) J. Neurosci. 5004-5013 (1996).

Stys, Peter K. et al., *Ionic Mechanisms of Anoxic Injury in Mammalian CNS White Matter: Role of Na$^+$ Channels and Na$^{(+)}$-Ca2$^+$ Exchanger*, 12(2) J. Neurosci. 430-439 (1992).

Stys, Peter K. et al., *Noninactivating, Tetrodotoxin-Sensitive Na$^+$ Conductance in Rat Optic Nerve Axons*, 90(15) Proc. Natl. Acad. Sci. USA, 6976-6980 (1993).

Stys, Peter K., *Anoxic and Ischemic Injury of Myelinated Axons in CNS White Matter: From Mechanistic Concepts to Therapeutics*, 18(1) J. Cereb. Blood Flow Metab. 2-25 (1998).

Taddese, Abraha & Bruce P. Bean, *Subthreshold Sodium Current from Rapidly Inactivating Sodium Channels Drives Spontaneous Firing of Tubermammillary Neurons*, 33(4) Neuron 587-600 (2002).

Urbani, Andrea & Ottorino Belluzzi, *Riluzole Inhibits the Persistent Sodium Current in Mammalian CNS Neurons*, 12(10) Eur. J. Neurosci. 3567-3574 (2000).

Vreugdenhil, Martin et al., *Persistent Sodium Current in Subicular Neurons Isolated from Patients with Temporal Lobe Epilepsy*, 19(10) Eur. J. Neurosci. 2769-2778 (2004).

Waxman, Stephen G., *Ion Channels and Neuronal Dysfunction in Multiple Sclerosis*, 59(9) Arch. Neurol. 1377-1380 (2002).

Waxman, Stephen G., *Sodium Channels as Molecular Targets in Multiple Sclerosis*, 39(2) J. Rehabil. Res. Dev. 233-242 (2002).

Wood, John N. & Mark D. Baker, *Voltage-Gated Sodium Channels*, 1(1) Curr. Opin. Pharmacol. 17-21 (2001).

Yu, Frank H. & William A. Catterall, *Overview of the Voltage-Gated Sodium Channel Family*, 4(3) Genome Biol. 207 (2003).

Zamore, Phillip D., *RNA Interference: Listening to the Sound of Silence*, 8(9) Nat. Struct. Biol. 746-750 (2001).

Nielsen et al, "Solution Structure of μ-Conotoxin PIIIA, a Preferential Inhibitor of Persistent Tetrodotoxin-Sensitive Sodium Channels", The Journal of Biological Chemistry, vol. 277, No. 30, Jul. 26, 2002, pp. 27247-27255.

| Compound ID | Molecular Formula | MW | Structure | IC50 (P), mM | IC50 (T), mM | Selectivity |
|---|---|---|---|---|---|---|
| Compound 1 (Formula 1) | C15H17NOS | 259.37 | 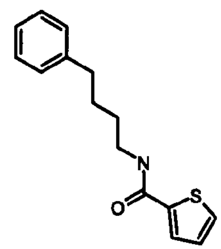 | 0.09 | 2.9 | 32 |
| Compound 2 (Formula 2) | C21H18N3O | 328.40 | 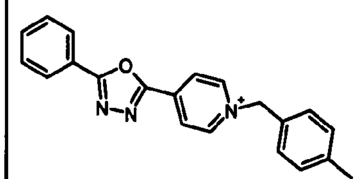 | 0.42 | 16 | 38 |
| Compound 3 (Formula 3) | C27H33NO2 | 403.57 | 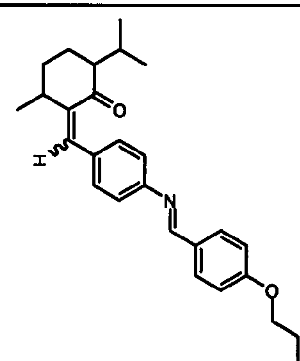 | 0.9 | 408 | 453 |
| Compound 4 (Formula 4) | C17H12NO4F3 | 351.28 | 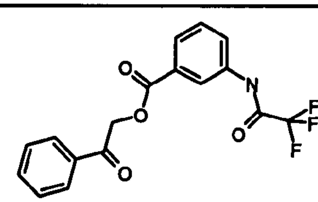 | 0.24 | 26.4 | 110 |

Fig. 1

TREATING NEUROLOGICAL DISORDERS USING SELECTIVE ANTAGONISTS OF PERSISTENT SODIUM CURRENT

CROSS REFERENCES TO RELATED APPLICATIONS

This application is a divisional and claims priority pursuant to 35 U.S.C. §120 to U.S. patent application Ser. No. 10/928,949, filed Aug. 27, 2004, an application that claims priority pursuant to 35 U.S.C. §119(e) to provisional application Ser. No. 60/498,902 filed Aug. 29, 2003, both of which are hereby incorporated by reference in their entirety.

BACKGROUND OF THE INVENTION

1. Field of the Invention

This invention relates generally to the fields of neurobiology, physiology, biochemistry and medicine and can be directed toward the treatment of neurological disorders and, in particular, to the therapeutic use of compounds that selectively reduce persistent sodium currents to treat neurological disorders.

2. Background Information

The lipid bilayer membrane of all cells forms a barrier that is largely impermeable to the flux of ions and water. Residing within the membrane are a superfamily of proteins called ion channels, which provide selective pathways for ion flux. Precisely regulated conductances produced by ion channels are required for intercellular signaling and neuronal excitability. Over the past 50 years, an increasing number of diseases of the nervous system and other excitable tissues have been shown to result from the dysregulation of ion channels. This class of disease has been termed channelopathies.

In particular, a group of ion channels that open upon depolarization of excitable cells are classified as voltage-gated and are responsible for electrical activity in nerve, muscle and cardiac tissue. In neurons, ion currents flowing through voltage-gated sodium channels are responsible for rapid spike-like action potentials. During action potentials the majority of sodium channels open very briefly. These brief openings result in transient sodium currents. However, a subset of voltage-gated sodium channels does not close rapidly, but remain open for relatively long intervals. These channels therefore generate sustained or persistent sodium currents. The balance between transient and persistent sodium current is crucial for maintaining normal physiological function and electrical signaling throughout the entire nervous system.

In conditions characterized by aberrant levels of persistent sodium current, normal function is disrupted when neurons discharge signals inappropriately and include, e.g., neuropathies; hypoxias and ischemias; behavioral disorders and dementia; and movement and neurodegenerative diseases. For example, in the case of the neuropathies embraced by epilepsy, there can be a brief electrical "storm" arising from neurons that are inherently unstable because of a genetic defect as in various types of inherited epilepsy, or from neurons made unstable by metabolic abnormalities such as low blood glucose, or alcohol. In other cases, the abnormal discharge can come from a localized area of the brain, such as in patients with epilepsy caused by head injury or brain tumor. In the case of ischemic injuries, such as, e.g., cerebral ischemia and myocardial ischemia, there can be prolonged electrical activity arising from neurons in which persistent sodium channel expression or activity is increased. Such aberrant electrical activity can cause or contribute to neuronal death, which can lead to debilitating injury or death of an individual. Aberrant electrical activity also can contribute to neurodegenerative disorders such as, without limitation, Parkinson's disease, Alzheimer's disease, Huntington's disease, amyotrophic lateral sclerosis and multiple sclerosis.

At present, treatments for many diseases characterized by aberrant levels of persistent sodium channel current are inadequate or non-existent. Current therapies, such as, e.g., Berger et al., *Treatment of Neuropathic Pain*, U.S. Pat. No. 5,688,830 (Nov. 18, 1997); Marquess et al., *Sodium Channel Drugs and Uses*, U.S. Pat. No. 6,479,498 (Nov. 12, 2002); Choi et al., *Sodium Channel Modulators*, U.S. Pat. No. 6,646,012 (Nov. 11, 2003); and Chinn et al., *Sodium Channel Modulators*, U.S. Pat. No. 6,756,400 (Jun. 29, 2004), encompass general sodium channel modulators that systemically effect transient currents. As such, the usefulness of available sodium channel blocking drugs is severely limited by potentially adverse side effects, such as, e.g., paralysis and cardiac arrest.

Thus, there exists a need to identify new therapeutic methods that can be used to selectively treat conditions characterized by aberrant levels of persistent sodium current, such as, e.g., neuropathies; hypoxias and ischemias; behavioral disorders and dementia; and movement and neurodegenerative diseases, and to protect the brain from the damaging effects of persistent sodium current. The present invention satisfies these needs and provides related advantages as well.

SUMMARY OF THE INVENTION

The present invention provides methods of treating a mammal having a condition characterized by aberrant levels of persistent sodium current. In one embodiment, the method involves administering to the mammal an effective amount of a selective persistent sodium current antagonist that has at least 20-fold selectivity for a persistent sodium current relative to transient sodium current. In further embodiments, the antagonist has at least 50-fold selectivity for a persistent sodium current, at least 200-fold selectivity for a persistent sodium current, at least 400-fold selectivity for a persistent sodium current, at least 600-fold selectively for a persistent sodium current, or at least 1000-fold selectively for a persistent sodium current, relative to a transient sodium current. A variety of mammals can be treated by the methods of the invention including, without limitation, humans.

The methods of the invention can be used to treat a variety of conditions characterized by aberrant levels of persistent sodium current. In certain embodiments, the methods are directed to treating neuropathies, including, without limitation, amyloidosis, autoimmune disorders, palsies, connective tissue disorders, epilepsies, and conditions associated with neuropathies like alcoholism, cancers, infectious diseases, organ disorders and vitamin deficiencies. In other embodiments, the methods are directed to treating hypoxic and ischemic conditions, such as, e.g., cerebral ischemia, myocardial ischemia, ischemia retinae, diabetes ischemia and postural ischemia. In still other embodiments, the methods are directed to treating behavioral disorders, dementia, movement disorders, and neurodegenerative diseases, such as, without limitation, Parkinson's disease, Alzheimer's disease, Huntington's disease, amyotrophic lateral sclerosis and multiple sclerosis. In further embodiments, the methods are directed to treating diabetic retinopathy. In yet other embodiments, the methods are directed to treating conditions characterized by aberrant levels of intracellular nitric oxide. In additional embodiments, the methods provide for reducing neuronal death associated with aberrant levels of persistent sodium current.

A variety of selective persistent sodium current antagonists can be useful in the methods of the invention. In one embodiment, a method of the invention is practiced by administering an effective amount of a selective antagonist that has at least 20-fold selectivity for a persistent sodium current relative to a transient sodium current. In further embodiments, the antagonist has at least 50-fold selectivity for a persistent sodium current; at least 200-fold selectivity for a persistent sodium current; at least 400-fold selectivity for a persistent sodium current; at least 600-fold selectively for a persistent sodium current; or at least 1000-fold selectively for a persistent sodium current, relative to transient sodium current.

In further embodiments, the methods of the invention involve administering an effective amount of a selective persistent sodium current antagonist belonging to one of the disclosed structural classes of selective persistent sodium current antagonists. Such a selective persistent sodium channel antagonist can be, without limitation, a compound represented by a formula selected from Formula 1:

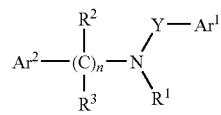

wherein,
$Ar^1$ is an aryl group;
$Ar^2$ is an aryl group;
Y is absent or is selected from:

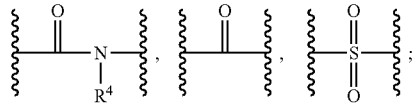

$R^1$ is selected from hydrogen, $C_1$-$C_8$ alkyl, aryl, arylalkyl;
$R^2$ and $R^3$ are independently selected from hydrogen, $C_1$-$C_8$ alkyl, aryl, arylalkyl, hydroxy, fluoro, $C_1$-$C_8$ carbocyclic ring, or $C_1$-$C_8$ heterocyclic ring;
$R^4$ is selected from hydrogen, $C_1$-$C_8$ alkyl, aryl, arylalkyl;
$R^5$ and $R^6$ are selected from hydrogen, fluoro, $C_1$ to $C_8$ alkyl, hydroxy;
$R^7$ is selected from hydrogen, $C_1$ to $C_8$ alkyl, aryl, arylalkyl; and
n is an integer of from 1 to 6;
Formula 4

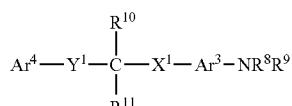

wherein,
$Ar^3$ is an aryl group;
$Ar^4$ is an aryl group;
$X^1$ and $Y^1$ are independently selected from

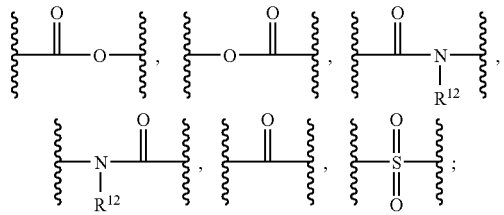

$R^5$ and $R^6$ are independently selected from hydrogen, fluoro, $C_1$ to $C_8$ alkyl, hydroxy;
$R^7$ is selected from hydrogen, $C_1$ to $C_8$ alkyl, aryl, arylalkyl;
$R^8$ and $R^9$ are selected from hydrogen, $C_1$-$C_8$ alkyl, aryl, arylalkyl, $COR^{12}$, $COCF_3$;
$R^{10}$ and $R^{11}$ are selected from hydrogen, halogen, hydroxyl, $C_1$-$C_8$ alkyl, aryl, arylalkyl, and
$R^{12}$ is selected from hydrogen, $C_1$-$C_8$ alkyl, aryl, arylalkyl;
Formula 2

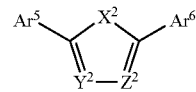

wherein,
$Ar^5$ is an aryl group;
$Ar^6$ is an aryl group;
$X^2$ is O, S, or $NR^{14}$;
$Y^2$ is N or $CR^{15}$;
$Z^2$ is N or $CR^{16}$;
$R^5$ and $R^6$ are selected from hydrogen, fluoro, $C_1$ to $C_8$ alkyl, hydroxy;
$R^7$ is selected from hydrogen, $C_1$ to $C_8$ alkyl, aryl, arylalkyl;
$R^{13}$ is selected from halogen, $C_1$-$C_8$ alkyl, arylalkyl, and $(CR^5R^6)_cN(R^7)_2$;
$R^{14}$ is selected from hydrogen, halogen, $C_1$ to $C_8$ alkyl, $CF_3$, $OCH_3$, $NO_2$, $(CR^5R^6)_cN(R^7)_2$;
$R^{15}$ is selected from hydrogen, halogen, $C_1$ to $C_8$ alkyl, $CF_3$, $OCH_3$, $NO_2$, $(CR^5R^6)_cN(R^7)_2$;
$R^{16}$ is selected from hydrogen, halogen, $C_1$ to $C_8$ alkyl, $CF_3$, $OCH_3$, $NO_2$, $(CR^5R^6)_cN(R^7)_2$; and
c is 0 or an integer from 1 to 5; and
Formula 3

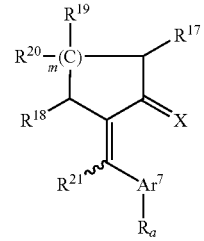

wherein,
$Ar^7$ is an aryl group;
R is selected from halogen, $C_1$-$C_8$ alkyl, $NR^{22}R^{23}$, $OR^{22}$;
$R^5$ and $R^6$ are selected from hydrogen, fluoro, $C_1$ to $C_8$ alkyl, hydroxy;

$R^7$ is selected from hydrogen, $C_1$ to $C_8$ alkyl, aryl, arylalkyl;

$R^{17}$ and $R^{18}$ are independently selected hydrogen, $C_1$-$C_8$ alkyl, aryl, arylalkyl, hydroxy;

$R^{19}$ and $R^{20}$ are independently selected from hydrogen, halogen, $C_1$-$C_8$ alkyl, hydroxy, amino, $CF_3$;

$R^{21}$, $R^{22}$, and $R^{23}$ are independently selected from hydrogen, aryl or $C_1$-$C_8$ alkyl;

a is 0 or an integer from 1 to 5; and m is 0 or and integer from 1 to 3.

A compound corresponding to any of the above formulas also can be a pharmaceutically acceptable salt, ester, amide, or geometric, steroisomer, or racemic mixture.

Any of the variety of routes of administration can be useful for treating a neurological disorder according to a method of the invention. In particular embodiments, administration is performed peripherally, systemically or orally.

BRIEF DESCRIPTION OF THE DRAWINGS

FIG. 1 shows four compounds that are selective persistent sodium current antagonists.

DETAILED DESCRIPTION OF THE INVENTION

I. Voltage-gated Sodium Channels

Figure 2:
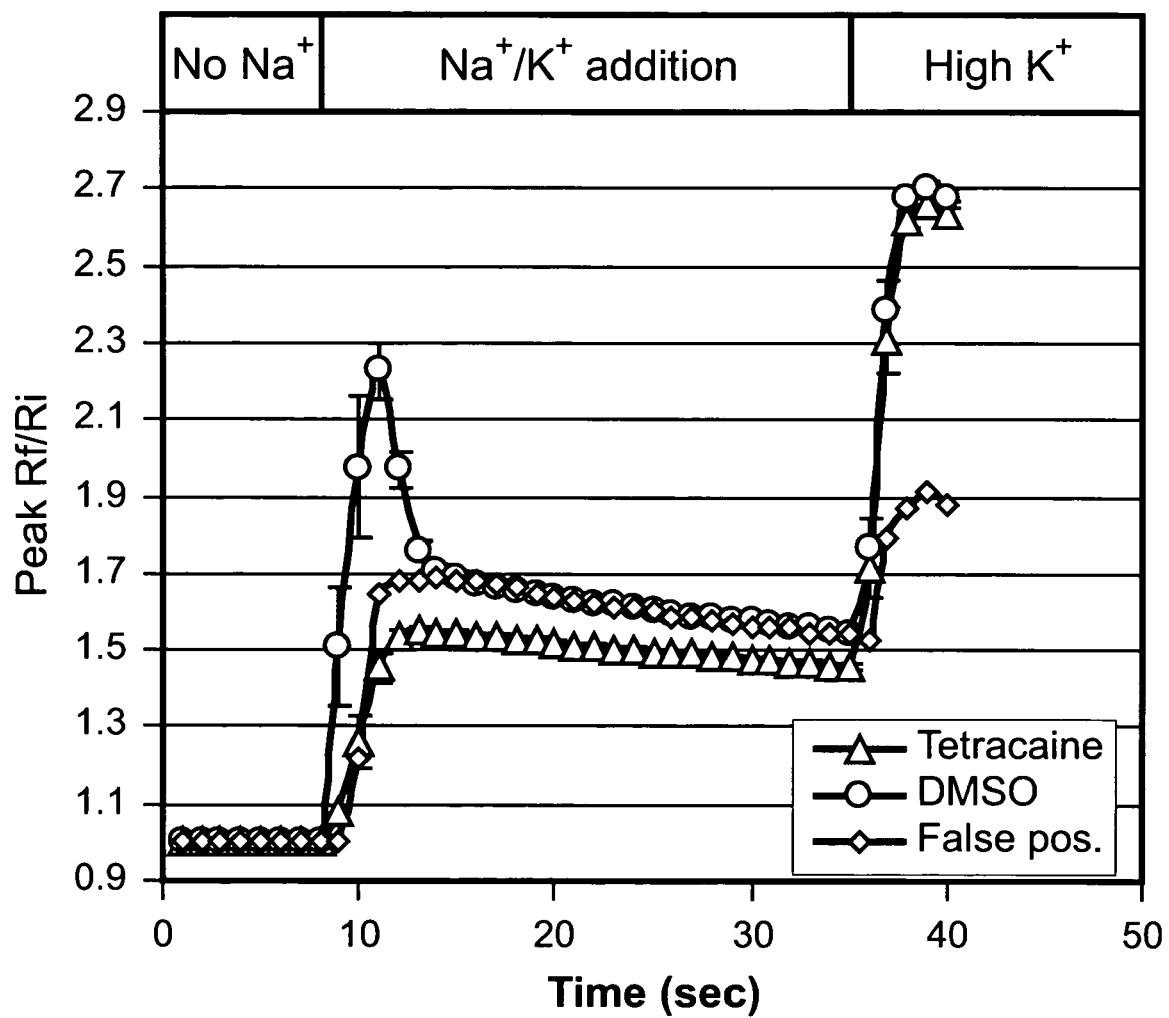
FIG. 2 shows inhibition of persistent current-dependent depolarization by $Na^+$ channel blockers. In the this assay, cells are resting in wells containing 80 µl of TEA-MeSO$_3$ ($Na^+$-free box) to which is added 240 µl of NaMeSO$_3$ buffer containing 13 mM KMeSO$_3$ for a final $K^+$ concentration of 10 mM and a final $Na^+$ concentration of 110 mM ($Na^+$/$K^+$-addition). This elicits a robust depolarizing response. Following the resolution of the sodium-dependent depolarization, a second aliquot of KMeSO$_3$ is added to the well bringing the final $K^+$ concentration to 80 mM (High potassium-addition). This addition results in a second depolarizing response. Compounds that reduce the sodium-dependent, but not the potassium-dependent depolarizations are selected as persistent sodium channel blockers. Circles indicate the control response with 0.1% DMSO added, triangles show the effects of the sodium channel inhibitor tetracaine (10 µM) and the diamonds show the response during the application of a non-specific channel blocker.

In the normal functioning of the nervous system, neurons are capable of receiving a stimulus, and in response, propagating an electrical signal away from their neuron cell bodies (soma) along processes (axons). From the axon, the signal is delivered to the synaptic terminal, where it is transferred to an adjacent neuron or other cell. Voltage-sensitive sodium channels have a critical role in nervous system function because they mediate propagation of electrical signals along axons.

Voltage-gated sodium channels are members of a large mammalian gene family encoding at least 9 alpha- and 3 beta-subunits. While all members of this family conduct $Na^+$ ions through the cell membrane, they differ in tissue localization, regulation and, at least in part, in kinetics of activation and inactivation, see, e.g., William A. Catterall, *From Ionic Currents to Molecular Mechanism: The Structure and Function of Voltage-gated Sodium Channels*, 26(1) NEURON 13-25 (2000); and Sanja D. Novakovic et al., *Regulation of $Na^+$ Channel Distribution in the Nervous System*, 24(8) TRENDS NEUROSCI. 473-478 (2001), which are hereby incorporated by reference in their entirety.

Generally, under resting conditions, sodium channels are closed-until a stimulus depolarizes the cell to a threshold level. At this threshold, sodium channels begin to open and then rapidly generate the upstroke of the action potential. Normally during an action potential, sodium channels open briefly (one millisecond) and then close (inactivate) until the excitable cell returns to its resting potential and the sodium channels re-enter the resting state.

Without wishing to be bound by the following, this behavior of voltage-gated sodium channels can be understood as follows. Sodium channels can reside in three major conformations or states. The resting or "closed" state predominates at negative membrane potentials ($\leq -60$ mV). Upon depolarization, channels open and allow current to flow. Transition from the resting state to the open state occurs within a millisecond after depolarization to positive membrane potentials. Finally, during sustained depolarization (>1-2 ms), channels enter a second closed or inactive state. Subsequent re-opening of channels requires recycling of channels from an inactive state to a resting state, which occurs when the membrane potential returns to a negative value (repolarization). Therefore, membrane depolarization not only causes sodium channels to open, but also causes them to close, during sustained depolarization.

A small fraction of the sodium channels can fail to inactivate even with sustained depolarization. This non-inactivating sodium current is called a "persistent" sodium current. Four sodium channels, Nav1.3, Nav1.5, Nav1.6 and Nav1.9, have historically been known to generate a persistent current. Recent evidence, however, suggests that all voltage-gated sodium channels are capable of producing a persistent current, see, e.g., Abraha Taddese & Bruce P. Bean, *Subthreshold Sodium Current from Rapidly Inactivating Sodium Channels Drives Spontaneous Firing of Tubermammillary Neurons*, 33(4) NEURON 587-600 (2002); Michael Tri H. Do & Bruce P. Bean, *Subthreshold Sodium Currents and Pacemaking of Subthalamic Neurons: Modulation by Slow Inactivation*, 39(1) NEURON 109-120 (2003). The mechanism that produces a persistent current is poorly understood. Two hypothesis are (1) that different sodium channels produce transient and persistent currents, and (2) that a sodium channel capable of producing transient sodium current enters a different gating mode to produce a persistent current. Persistent sodium channels can open at more negative membrane potentials relative to normal sodium channels and inactivate at more positive potentials, see, e.g., Jacopo Magistretti & Angel Alonso, *Biophysical Properties and Slow-voltage Dependent Inactivation of a Sustained Sodium Current in Entorhinal Cortex Layer-II Principal Neurons: A Whole-Cell and Single-Channel Study* 114(4) J. GEN. PHYSIOL. 491-509 (1999). Persistent sodium current have been observed at membrane potentials as negative as −80 mV, see, e.g., Peter K. Stys, *Anoxic and Ischemic Injury of Myelinated Axons in CNS White Matter: From Mechanistic Concepts to Therapeutics,* 18(1) J. CEREB. BLOOD FLOW METAB. 2-25 (1998) and have been shown to persist for seconds following depolarization at potentials as positive as 0 mV, see, e.g., Magistretti & Alonso, supra, (1999). Thus, persistent sodium current is distinct from, and can be readily distinguished from, transient sodium current.

Although the physiological role of persistent sodium current is not fully understood, such current can function in generating rhythmic oscillations; integrating synaptic input; modulating the firing pattern of neurons; and regulating neuronal excitability and firing frequency, see, e.g., Wayne E. Crill, *Persistent Sodium Current in Mammalian Central Neurons* 58 ANNU. REV. PHYSIOL. 349-362 (1996); and David S. Ragsdale & Massimo Avoli, *Sodium Channels as Molecular Targets for Antiepileptic Drugs,* 26(1) BRAIN RES. BRAIN RES. REV. 16-28 (1998). Aberrant persistent sodium current can contribute to the development or progression of many pathological conditions. For example, persistent sodium current are thought to induce deleterious phenomena, including, e.g., neuropathies, cardiac arrhythmia, epileptic seizure, neurodegeneration, and neuronal cell death under hypoxic and ischemic conditions, see, e.g., Christoph Lossin et al., *Molecular Basis of an Inherited Epilepsy* 34(6) NEURON 877-84 (2002); Peter K. Stys et al., *Ionic Mechanisms of Anoxic Injury in Mammalian CNS White Matter: Role of Na$^+$ Channels and Na$^{(+)}$—Ca2$^+$ Exchanger,* 12(2) J. NEUROSCI. 430-439 (1992); Peter K. Stys et al., *Noninactivating, Tetrodotoxin-Sensitive Na$^+$ Conductance in Rat Optic Nerve Axons,* 90(15) PROC. NATL. ACAD. SCI. USA, 6976-6980 (1993); and Giti Garthwaite et al., *Mechanisms of Ischaemic Damage to Central White Matter Axons: A Quantitative Histological Analysis Using Rat Optic Nerve,* 94(4) NEUROSCIENCE 1219-1230 (1999). Thus, aberrant persistent sodium current can contribute to development or progression of pathological conditions by collapsing the normal cell transmembrane gradient for sodium, leading to reverse operation of the sodium-calcium exchanger, and resulting in an influx of intracellular calcium, which injures the axon, see, e.g., Stys et al., supra, (1992).

While abnormal activity of a persistent current can underlie a wide array of neurological disorders, the underlying mechanisms appears to be similar. It is generally understood that abnormally increased persistent sodium current can depolarize the resting membrane potential or reduce the rate of repolarization during an action potential. Either effect may produce a state of hyper-excitability in which aberrant neuronal behavior is manifested. This aberrant neuronal behavior can result in a neuron with increased firing rates, enhanced sensitivity to synaptic input or abnormal repetitive or rhythmic firing patterns. It is also generally understood that abnormally high levels of persistent current generate sustained membrane depolarization and a concomitant increase of Na$^+$ within the cell. This high Na$^+$ influx, in turn, drives the sodium/calcium exchanger, which in turn, results in detrimental levels of Ca$^{2+}$ to accumulate inside affected cells. Abnormally high levels of Ca$^{2+}$ result in neuronal cell dysfunction and neuronal cell death. Thus, by collapsing the normal cell transmembrane gradient for sodium, a persistent current can reverse the operation of the sodium-calcium exchanger, and the resulting an influx of intracellular calcium would cause injures or death to a nerve. As disclosed herein, conditions associated with aberrant persistent sodium current can be treated by selectively inhibiting or reducing persistent sodium current without compromising normal transient sodium current function, thereby allowing normal neuronal function (excitability).

II. Neurological Disorders and Persistent Sodium Current

The methods of the invention can be used to reduce or eliminate aberrant levels of persistent sodium current in a mammal, and thus can be used, for example, to treat any of a variety of neurological conditions that involve aberrant levels of persistent sodium current. Neuronal disturbance, including neuronal dysfunction and neuronal death, associated with unwanted persistent neuronal firing can contribute to, or cause, a variety of disorders of the central and peripheral nervous systems. Therefore, a compound that decreases persistent sodium current without a similar decrease in non-pathological transient sodium current can effectively treat such conditions, without harmful side effects that generally accompany non-selective sodium channel blockers currently in use. Because all sodium channels seem capable of generating a persistent current, and since any condition whose underlying cause includes an aberrant persistent sodium current, a very wide range of neurological abnormalities can be treated using a persistent sodium channel antagonist. Conditions that can be treated according to a method of the invention include, without limitation, neuropathies such as, e.g., epilepsies, palsies, connective tissue disorders and conditions associated with neuropathies, like, alcoholism, cancers, infectious diseases, organ disorders and vitamin deficiencies; hypoxia and ischemia, such as, e.g., cerebral hypoxia/ischemia, myocardial hypoxia/ischemia, myoischemia, diabetes ischemia and hypoxia/ischemic retinopathy; and behavioral disorders, dementia, movement disorders and neurodegenerative conditions such as. e.g., Parkinson's disease, Alzheimer's disease, Huntington's disease, amyotrophic lateral sclerosis and multiple sclerosis.

Based on the identification of selective persistent sodium current antagonists that have at least 20-fold selectivity for persistent sodium current relative to transient sodium current, the present invention provides therapeutic methods that involve selectively antagonizing persistent sodium channel. Whereas certain conditions have been treated using non-selective sodium channel blockers, albeit with significant side effects, the methods of the present invention involve administering to a mammal an effective amount of a selective persistent sodium current antagonist that has at least 20-fold selectivity for persistent sodium current relative to transient sodium current.

By preventing or reducing aberrant levels of persistent sodium current, the progression of various conditions associated with unwanted persistent neuronal firing can be stopped or slowed, and improvement in the pathophysiology or symptoms appreciated. As used herein, the term "conditions associated with unwanted persistent neuronal firing" means a disorder in which persistent membrane sodium conductance causes or contributes to functional changes resulting from disease or injury. Such functional changes, or pathophysiology, can involve either neuronal damage, including neuronal death; unwanted persistent neuronal firing; or both. As used herein, the term "reducing," when used in reference to neuronal death means preventing, decreasing or eliminating unwanted persistent neuronal firing or aberrant levels of persistent sodium current. Reducing aberrant levels of persistent sodium current by administering a selective persistent sodium current antagonist can be an effective method for treating conditions involving neuronal dysfunction or neuronal death, for example, for treating conditions characterized by aberrant levels of persistent sodium current or aberrant levels of intracellular nitric oxide.

III. Treatment of Neuropathies Using a Selective Persistent Sodium Current Antagonist The present invention provides methods of treating a neuropathy by administering an effective amount of a selective persistent sodium current antagonist having at least 20-fold selectivity for persistent sodium current relative to transient sodium current. Aberrant levels of sodium current are associated with a variety of neuropathic conditions that led to neuronal dysfunction or neuronal death. As used herein, the term "neuropathic condition" means any condition resulting in nerve damage, including, e.g., motor nerve damage, sensory nerve damage, autonomic nerve damage. Neuropathic conditions include a heterogeneous group of conditions of the central or peripheral nervous system that include, without limitation, headache, pain, inflammatory diseases, movement disorders, tumors, birth injuries, developmental abnormalities, neurocutaneous disorders, autonomic disorders, and paroxysmal disorders. As such, a neuropathic condition have a wide range of different etiologies, including, e.g., hereditary or sporatic, secondary to a toxic or metabolic process, and can result from an injury, trauma, disease, or infection. Such conditions can be characterized by abnormalities of relatively specific regions of the brain or specific populations of neurons. The particular cell groups affected in different neuropathic conditions typically determine the clinical phenotype of the condition.

Exemplary examples of neuropathies include, without limitation, amyloidosis; autoimmune disorders such as, e.g., Guillain-Barré syndrome, Hashimoto's thyroiditis, pernicious anemia, Addison's disease, type I diabetes, rheumatoid arthritis, systemic lupus erythematosus, dermatomyositis, Sjogren's syndrome, lupus erythematosus, multiple sclerosis, myasthenia gravis, Reiter's syndrome, Grave's disease; movement disorders like palsies involving injury or damage to nerves such as, e.g., cerebral palsy, Bell's palsy, diver's palsy, extrapyramidial cerebral palsy, lead palsy, Ramsey Hunt syndrome, obstetrical palsy, like Erb palsy and Klumpke palsy, posticus palsy, Scrivener's palsy, tardy median palsy, tardy ulnar palsy, and progressive supranuclear palsy; arthritis/connective tissue disorders such as, e.g., osteoarthritis, rheumatoid arthritis, juvenile arthritis, gouty arthritis; spondyloarthritis, scleroderma, fibromyalgia, osteoporosis, noise sensitivity, multiple chemical sensitivity and asthma; conditions associated with neuropathies like alcoholism, cancers, infectious diseases, organ disorders and vitamin deficiencies; and epilepsies, seizures and paroxysmal conditions. The skilled person understands that these and other mild, moderate or severe neuropathic conditions can be treated according to a method of the invention.

As a non-limiting example, epilepsies are conditions that can be characterized by aberrant levels of persistent sodium current. Epilepsies and other seizure disorders, are a group of neuronal dysfunction disorders of the central nervous system and are generally characterized by sudden seizures, muscle contractions, and partial or total loss of consciousness. Epilepsy is a disorder characterized by the occurrence of at least 2 unprovoked seizures. Seizures are the manifestation of abnormal hypersynchronous discharges of cortical neurons. The clinical signs or symptoms of seizures depend upon the location and extent of the propagation of the discharging cortical neurons. That seizures are a common nonspecific manifestation of neurologic injury and disease should not be surprising, because the main function of the brain is the transmission of electrical impulses. The lifetime likelihood of experiencing at least one epileptic seizure is about 9%, and the lifetime likelihood of being diagnosed as having epilepsy is almost 3%. However, the prevalence of active epilepsy is only 0.8%.

Epilepsies can be divided into two major categories. Partial-onset seizures begin in one focal area of the cerebral cortex, while generalized-onset seizures have an onset recorded simultaneously in both cerebral hemispheres. Some seizures are difficult to fit into one particular class, and they are considered as unclassified seizures. Partial-onset seizures include, e.g., simple partial seizures, complex partial seizures and secondarily generalized tonic-clonic seizures. Generalized-onset seizures include, e.g., absence seizures, tonic seizures, clonic seizures, myoclonic seizures, primary generalized tonic-clonic seizures, and atonic seizures. Likewise, epileptic syndromes can be classified into two major groups, localization-related syndromes and generalized-onset syndromes.

Voltage-gated sodium channels, which play an important role in initiation and transmission of action potentials, are involved in the etiology of epilepsy, and appear to include $Na_v1.1$, $Na_v1.2$, $Na_v1.3$, $Na_v1.5$, and $Na_v1.6$, see, e.g., Rudiger Kohling, *Voltage-gated Sodium Channels in Epilepsy*, 43(11) Epilepsia 1278-1295 (2002); Michael M. Segal *Sodium Channels and Epilepsy Electrophysiology*, 241 NOVARTIS FOUND. SYMP. 173-180 (2002), which are hereby incorporated by reference in their entirety. Examination of individuals suffering from hereditary forms of epilepsy has revealed these individuals carried deleterious mutations in $Na_v1.1$ or $Na_v1.2$, see, e.g., Lossin et al., supra, (2002); Miriam H. Meisler et al., *Mutations of Voltage-gated Sodium Channels in Movement Disorders and Epilepsy*, 241 NOVARTIS FOUND. SYMP. 72-81 (2002); J. Spampanato et al., *Generalized Epilepsy with Febrile Seizures Plus Type 2 Mutation W1204R Alters Voltage-Dependent Gating of Na(V) 1.1 Sodium Channels*, 116(1) NEUROSCIENCE 37-48 (2003); Paolo Bonanni et al., *Generalized Epilepsy with Febrile Seizures Plus (GEFS+): Clinical Spectrum in Seven Italian Families Unrelated to SCN1A, SCN1B, And GABRG2 Gene Mutations*, 45(2) EPILEPSIA 149-158 (2004); Berten P. G. M. Ceulemans et al., *Clinical Correlations Of Mutations in the SCN1A Gene: from Febrile Seizures to Severe Myoclonic Epilepsy in Infancy*, 30(4) PEDIATR. NEUROL. 236-243 (2004); Goryu Fukuma et al., *Mutations of Neuronal Voltage-Gated $Na^+$ Channel Alpha 1 Subunit Gene SCN1A in Core Severe Myoclonic Epilepsy in Infancy (SMEI) and in Borderline SMEI (SMEB)*, 45(2) EPILEPSIA 140-148 (2004); and Kazusaku Kamiya et al., *A Nonsense Mutation of the Sodium Channel Gene SCN2A in a Patient with Intractable Epilepsy and Mental Decline*, 24(11) J. NEUROSCI. 2690-2698 (2004), which are hereby incorporated by reference in their entirety. In addition, epilepsy appears to be caused by abnormal nerve discharges in the brain that result in aberrant levels of persistent sodium current, see, e.g., Newton Agrawal et al., *Increased Persistent Sodium Currents in Rat Entorhinal Cortex Layer V Neurons in a Post-Status Epilepticus Model of Temporal Lobe Epilepsy*, 44(12) EPILEPSIA 1601-1604 (2003); and Martin Vreugdenhil et al., *Persistent Sodium Current in Subicular Neurons Isolated from Patients with Temporal Lobe Epilepsy*, 19(10) EUR. J. NEUROSCI. 2769-2778 (2004), which are hereby incorporated by reference in their entirety. Both $Na_v1.1$ and $Na_v1.6$ are thought to be capable of producing a persistent current, see, e.g., Joshua P. Klein et al., *Dysregulation of Sodium Channel Expression in Cortical Neurons in a Rodent*

*Model of Absence Epilepsy,* 1000(1-2) BRAIN RES. 102-109 (2004), which is hereby incorporated by reference in its entirety. In view of the role of persistent sodium currents in epilepsy, a selective persistent sodium current antagonist can be advantageously used to treat epilepsy without deleterious side effects associated with non-selective sodium channel blockers.

IV. Treatment of Hypoxias and Ischemias Using a Selective Persistent Sodium Current Antagonist The present invention also provides methods of treating a hypoxia or ischemia by administering an effective amount of a selective persistent sodium current antagonist having at least 20-fold selectivity for persistent sodium current relative to transient sodium current. Neuronal damage or death occurring as a result of changes induced by hypoxia or ischemia appears to be associated with increased persistent sodium current, see, e.g., Anna K. M. Hammarström & Peter W. Gage, *Hypoxia and Persistent Current*, 31 (3) EUR. BIOPHYS. J. 323-330 (2002), which is hereby incorporated by reference in its entirety. As used herein, the term "hypoxia" means an incident during which the oxygen supply to a tissue is diminished or eliminated. A hypoxia can include, e.g., cerebral hypoxia, diffusion hypoxia, hypoxic hypoxia, cell hypoxia, ischemic hypoxia, or any other accidental or purposeful reduction or elimination of oxygen supply to a tissue. As used herein, the term "ischemia" means an incident during which the blood supply to a tissue is reduced or completely obstructed. An ischemia can include, e.g., cerebral ischemia, myocardiac ischemia, myoischemia, diabetes ischemia, ischemia retinae, postural ischemia, or any other accidental or purposeful reduction or complete obstruction of blood supply to a tissue. That a reduction or complete obstruction of blood to a tissue necessarily means a reduction or elimination of oxygen supply to that tissue, ischemias and hypoxias are usually related. The skilled person understands that these and other mild, moderate or severe hypoxic and ischemic conditions can be treated according to a method of the invention.

As a non-limiting example, cerebral ischemia occurs when a blood vessel bringing oxygen and nutrients to the brain bursts or is clogged by a blood clot or other material. Because of this rupture or blockage, part of the brain is deprived of its normal blood flow and the oxygen it contains. In the absence of oxygen, nerve cells in the affected area of the brain undergo deleterious changes and die. This neuronal cell death can lead to a stroke, resulting in loss of control of the body part normally controlled by these nerve cells. The devastating effects of stroke are often permanent because damaged nerve cells are not replaced.

Cerebral hypoxia or ischemia can result, without limitation, from CNS surgery, open heart surgery or any procedure during which the function of the cardiovascular system is compromised; trauma that results in reduction of blood flow to the brain; disease that causes reduction of blood flow to the brain, including cerebrovascular disease, such as chronic subdural hematoma, cavernous angioma, arteriovenous malformation, vascular dementia, carotid or circle of Willis hypertensive encephalopathy, multiple embolic infarctions, hypertensive encephalopathy and cerebral hemorrhage; infectious diseases that can cause cranial swelling that reduces blood flow to neurons, such as meningitis, Lyme encephalopathy, Herpes encephalitis, Creutzfeld-Jakob disease, cerebral toxoplasmosis and the like; trauma, such as head trauma and traumatic brain injury that cause a reduction in blood flow to neurons; and proliferative disorders that cause a reduction in blood flow to neurons, including diseases associated with the overgrowth of connective tissues, such as various fibrotic diseases, vascular proliferative disorders, and benign tumors. Proliferative disorders of the central nervous system include, for example, cerebellar astrocytomas, and medulloblastomas, ependymomas, gliomas, germinomas, and metastatic adenocarcinoma, metastatic bronchogenic carcinoma, meningioma, sarcoma and neuroblastoma.

Sodium channel inhibitors, such as, tetrotoxin (TTX) and lidocaine, and extracelluar $Na^+$ ions protect neurons from hypoxic and ischemic damage, suggesting that voltage-gated sodium channel activity is an early and important step in sensing oxygen levels and cell damage in neurons. It was subsequently shown that these oxygen sensing channels generated a persistent current, and hypoxic/ischemic conditions increased the activity of these persistent current channels that result in an abnormally high intake of $Na^+$., see, e.g., Anna H. K. Hammarström & Peter W. Gage, *Oxygen-sensing Persistent Sodium Channels in Rat Hippocampus,* 529(1) J. PHYSIOL. 107-118 (2000), which is hereby incorporated by reference in its entirety. The influx of $Na^+$ would drive the sodium/calcium exchanger, which in turn, would result in detrimental levels of $Ca^{2+}$ accumulate inside affected cells and cell death, see, e.g., Peter Lipton, *Ischemic Cell Death in Brain Neurons,* 79(4) PHYSIOL. REV. 1431-1568 (1999), which is hereby incorporated by reference in its entirety. Therefore, application of a selective persistent sodium current antagonist can serve as a neuroprotectant against cerebral hypoxia or ischemia, without the deleterious side effects associated with non-selective sodium channel blockers.

As another non-limiting example, myocardial ischemia is a disorder of cardiac function caused by insufficient blood flow to the muscle tissue of the heart. The decreased blood flow may be due to narrowing of the coronary arteries (coronary arteriosclerosis), to obstruction by a thrombus (coronary thrombosis), or less commonly, to diffuse narrowing of arterioles and other small vessels within the heart. Severe interruption of the blood supply to the myocardial tissue results in a concomitant interruption in oxygen which may lead to necrosis of cardiac muscle (myocardial infarction).

Abnormal levels of a persistent sodium current, which become prominent following cardiac hypoxia or ischemia, are associated with arrhythmias, which can trigger a heart attack, see, e.g., Hammarström & Gage, supra, (2002). Cardiac cells, such as, e.g., Purkinje fibers and ventricular myocytes, generate a persistent sodium current. Examination of ventricular myocytes in the presence or absence of oxygen indicates that persistent sodium current increases during hypoxia, and that this aberrant current could trigger early after depolarization, arrhythmia, and heart failure, see, e.g., Yue-Kun Ju et al., *Hypoxia Increases Persistent Sodium Current in Rat Ventricular Myocytes,* 497(2) J. PHYSIOL. 337-347 (1996), which is hereby incorporated by reference in its entirety. Additionally, application of tetrotoxin (TTX), a voltage-gated sodium channel inhibitor, reduces the action potential duration of a persistent current in human ventricular myocytes, as well as abolishes the early after depolarization in myocytes isolated from heart failure patients, see, e.g., Victor A. Maltsev et al., *Novel, Ultraslow Inactivating Sodium Current in Human Ventricular Cardiomyocytes,* 98(23) CIRCULATION 2545-2552 (1998), which is hereby incorporated by reference in its entirety.

Several voltage-gated sodium channels are localized in specific regions of the heart where they are believed to regulate distinct activities. The persistent sodium channel $Na_v1.5$ is found in the myocardium and intercalated disks/AV node and seems to be involved primarily in initiation and propagation of the action potential from cell to cell. On the other hand, $Na_v1.1$ and $Na_v1.3$ appear to generate a persistent current in the transverse tubules/SA node and may function in coordinating and synchronizing the action potential from the cell surface into the interior, see, e.g., Sebastian K. G. Maier et al., *An Unexpected Requirement for Brain-Type Sodium Channels for Control of Heart Rate in the Mouse Sinoatrial Node*, 100(6) PROC. NATL. ACAD. SCI. U.S.A. 3507-3512 (2003); and Sebastian K. G. Maier et al., *Distinct Subcellular Localization of Different Sodium Channel Alpha and Beta Subunits in Single Ventricular Myocytes from Mouse Heart*, 109(11) CIRCULATION 1421-1427 (2004), which are hereby incorporated by reference in their entirety. Furthermore, a missense mutation in $Na_v1.5$ that accelerates channel activation is associated with individuals diagnosed with cardiac arrhythmia, see, e.g., Igor Splawski et al., *Variant of SCN5A Sodium Channel Implicated in Risk of Cardiac Arrhythmia*, 297 SCIENCE 1333-1336 (2002), which is hereby incorporated by reference in its entirety. Thus, as seen in cerebral hypoxia/ischemia, as described above, elevated $Na^+$ levels due to an increased persistent current, will cause the sodium/calcium exchanger to import abnormally high levels $Ca^{2+}$, thereby triggering myocardial cell death. Thus, a selective persistent sodium current antagonist can be used beneficially to prevent cardiac hypoxia or ischemia without the harmful side effects associated with current non-selective sodium channel blockers.

In a third non-limiting example, ischemia retinae is a diminished blood supply in the retina due to diminished or failed blood circulation that can result in bilateral transitory or permanent blindness. Ischemia of the neuroretina and optic nerve can arise during an embolism, such as, e.g., retinal branch vein occlusion, retinal branch artery occlusion, central retinal artery occlusion, central retinal vein occlusion; as a result of a disease, such, e.g., diabetic retinopathy; during intravitreal surgery; by poisoning, such as, e.g., quinine; in retinal degenerations such as, e.g., retinitis pigmentosa, and in age-related macular degeneration; during an inflammation; during an infection; or exsanguination from recurring profuse haemorrhages (e.g., in parturition, gastric and duodenal ulcers, and pulmonary tuberculosis). The skilled person understands that the methods of the invention can be used to treat these and other types of ischemia known in the art.

The earliest ophthalmolscopic indication of an ischemic retinopathy is the appearance of microaneruysms, which correspond with areas of focal ischemia, see, e.g., Thomas W. Gardner et al., *Diabetic Retinopathy: More than Meets the Eye*, 47(Suppl. 2) SURV. OPHTHALMOL. s253-S262 (2002); and Alistair J. Barder, *A New View of Diabetic Retinopathy: A Neurodegenerative Disease of the Eye*, 27(2) PROG. NEUROPSYCHOPHARMACOL. BIOL. PSYCHIATRY. 283-290 (2003), which are hereby incorporated by reference in their entirety. Coincident with or preceding these clinical findings, significant electrophysiological changes can be observed, including reduction in oscillatory potentials, delays in visual evoked potentials and changes in pattern and multi-focal electroretinograms, see, e.g., Erich Lieth et al., *Retinal Neurodegeneration: Early Pathology in Diabetes*, 28(1) CLIN. EXPERIMENT. OPHTHALMOL. 3-8 (2000), which is hereby incorporated by reference in its entirety. Alterations in the normal ionic conductances of the neural retina, including retinal ganglion cells and their axons, have been associated with ischemic retinopathy, see, e.g., Stefan Quasthoff, The Role of Axonal Ion Conductances in Diabetic Neuropathy: A Review, 21(10) MUSCLE NERVE 1246-1255 (1998), which is hereby incorporated by reference in its entirety. Key observations include a decrease in conduction velocity, a dysfunction of nodal sodium channels and an increase in intracellular $Na^+$ concentration, see, e.g., Tom Brismar, *Abnormal Na-Currents in Diabetic Rat Nerve Nodal Membrane*, 10(Suppl. 2) DIABET. MED. 110S-112S (1993), which is hereby incorporated by reference in its entirety. The increased influx of $Na^+$ would drive the sodium/calcium exchanger to import abnormally high levels of intracellular calcium, a major cause of neuronal cell death, see, e.g., Lipton, supra, (1999). The gradual loss of neurons in the retina indicates that progress of the disease is ultimately irreversible, since these cells cannot usually be replaced. Selectively reducing persistent sodium current can provide an effective means for reducing symptoms or pathophysiology of retinal ischemia. Thus, analogous to the neuroprotective effects of selective persistent sodium current blockers during cerebral hypoxia/ischemia, the present invention discloses a method that prevents retinal ischemias.

V. Treatment of Neurodegenerative Conditions Using a Selective Persistent Sodium Current Antagonist The present invention further provides methods of treating a neurodegenerative condition by administering an effective amount of a selective persistent sodium current antagonist having at least 20-fold selectivity for persistent sodium current relative to transient sodium current. Aberrant levels of sodium current are associated with a variety of neurodegenerative conditions. As used herein, the term "neurodegenerative condition or disorder" means a condition characterized by progressive loss of neural tissue. Neurodegenerative conditions include a heterogeneous group of aberrant conditions of the central or peripheral nervous system that include, without limitation, behavioral disorders, dementia, neuromuscular disorders, movement disorders, inflammatory disorders and demyelinating diseases. Such conditions have many different etiologies such as, without limitation, sporatic or hereditary, secondary to toxic or metabolic processes, and can result from an injury, a trauma, a disease, or an infection. Neurodegenerative conditions are progressive conditions that can be age associated or chronic. Such conditions can be characterized by abnormalities of relatively specific regions of the brain or specific populations of neurons. The particular cell groups affected in different neurodegenerative conditions typically determine the clinical phenotype of the condition. In particular, neurodegenerative conditions can be associated with atrophy of a particular affected central or peripheral nervous system structure, and aberrant levels of sodium current and subsequent elevation of intracellular sodium can be a cause or contributing factor to this atrophy.

Exemplary neurodegenerative conditions include, but are not limited to, Motor Neuron Disease (ALS), Parkinsonian Syndromes, diffuse sclerosis, amyotrophic lateral sclerosis, multiple sclerosis, diffuse cerebral cortical atrophy, Lewy-body dementia, Pick disease, mesolimbocortical dementia, thalamic degeneration, bulbar palsy, Huntington chorea, cortical-striatal-spinal degeneration, cortical-basal ganglionic degeneration, cerebrocerebellar degeneration, familial dementia with spastic paraparesis, polyglucosan body disease, Shy-Drager syndrome, olivopontocerebellar atrophy, progressive supranuclear palsy, dystonia musculorum deformans, Hallervorden-Spatz disease, Meige syndrome, familial tremors, Gilles de la Tourette syndrome, acanthocytic chorea, Friedreich ataxia, Holmes familial cortical cerebellar atrophy, AIDS related dementia, Gerstmann-Straussler-Scheinker disease, progressive spinal muscular atrophy, progressive balbar palsy, primary lateral sclerosis, hereditary muscular atrophy, spastic paraplegia, peroneal muscular atrophy, hypertrophic interstitial polyneuropathy, heredopathia atactica polyneuritiformis, optic neuropathy, diabetic retinopathy, Alzheimer's disease and ophthalmoplegia. The skilled person understands that these and other mild, moderate or severe neurodegenerative conditions can be treated according to a method of the invention.

As a non-limiting example, multiple sclerosis is a condition that can be characterized by aberrant levels of persistent sodium current. Multiple Sclerosis (MS) an chronic inflammatory disease of the central nervous system affecting white matter tissue impacts more than 350,000 persons in the United States and world-wide may affect as many as 30 cases per 100,000 population. MS can therefore be considered a nerve fiber, or axonal disease. MS can cause damage in a random manner within the CNS causing lesions or plaques to appear in CNS axons. A lesion is characterized by a loss of myelin (demyelination), the material that insulates axons. Demyelination profoundly effects the electrical properties of the axon, slowing or blocking nervous impulses from occurring. A variety of bodily functions are affected as a result of the adverse effects on axon physiology. During the course of the disease axons are destroyed classifying MS as a neurodegenerative disease. Many people with the disorder are affected during what normally would be the most productive years of their lives since the age of onset is often between 28 and 35. Drug therapies currently available at best may slow down the disease or lessen the symptoms. It is obvious that there is an unmet need for therapies to treat this form of neurological disorder.

This neurodegenerative condition is typically marked by lack of muscle coordination, muscle weakness, speech problems, paresthesia, and visual impairments. In human patients with multiple sclerosis as well as animal models of this condition, there is evidence that onset of multiple sclerosis produces changes in the expression pattern of sodium channels within Purkinje cells. Dysregulated sodium channel expression can contribute to symptoms of multiple sclerosis. For example, a persistent sodium current can trigger calcium-mediated axonal injury via reverse sodium-calcium exchange, see, e.g., Stephen G. Waxman, *Sodium Channels as Molecular Targets in Multiple Sclerosis*, 39(2) J. REHABIL. RES. DEV. 233-242 (2002); and Stephen G. Waxman, *Ion Channels and Neuronal Dysfunction in Multiple Sclerosis*, 59(9) ARCH. NEUROL. 1377-1380 (2002), which are hereby incorporated by reference in their entirety. In myelinated axons, voltage-gated sodium channels $Na_v1.2$ and $Na_v1.6$ specifically cluster at the nodes of Ranvier. However, both exhibit altered expression along demyelinated axons derived from patients suffering with multiple sclerosis. In addition, $Na_v1.6$ and the sodium/calcium exchanger co-localize within axons expressing β-APP, a maker of axonal injury in multiple sclerosis. Thus in patients suffering from multiple sclerosis, altered distribution of $Na_v1.6$ is thought to produce a persistent current that results in aberrantly high influx of $Na^+$ which drives a sodium/calcium exchanger to import abnormally high levels of intraaxonal calcium, which triggers the neuronal damage seen in these individuals, see, e.g., Matthew J. Craner et al., *Molecular Changes in Neurons In Multiple Sclerosis: Altered Axonal Expression of $Na_v1.2$ and $Na_v1.6$ Sodium Channels And $Na^+/Ca2+$ Exchanger*, 101(21), PROC. NATL. ACAD. SCI. U.S.A. 8168-8173 (2004); and Matthew J. Craner et al., *Co-Localization of Sodium Channel $Na_v1.6$ and the Sodium-Calcium Exchanger at Sites of Axonal Injury in the Spinal Cord in EAE*, 127(2) BRAIN 294-303 (2004), which are hereby incorporated by reference in their entirety. Thus, selectively reducing this abnormally high persistent sodium current can provide an effective means for treating an individual having multiple sclerosis.

As another non-limiting example, amyotrophic lateral sclerosis (ALS) or "Motor Neuron Disease" is a neurodegenerative disorder of both the upper and lower motor neurons. The mean age of onset is approximately 55 years and the incidence of ALS is about two per 100,000. The prevalence of ALS in the USA is about 11 per 100,000 affecting approximately 30,000 people. There are about 5,000 new cases per year, or 15 per day. ALS is characterized by progressive weakness of the lower and upper extremities as well as stiffness, muscle twitching and shaking and muscle atrophy. ALS is a fatal disease with only 20% of those inflicted surviving 5 years. At present Riluzole is only FDA-approved drug that appears to slow down progression of the disease.

The etiology of ALS is unknown but one hypothesis proposes that glutamate excitotoxicity causes neuronal cell death associated with the disease. Interestingly, in an in vitro model of neuronal excitotoxicity, voltage-gated sodium channels, NMDA receptors and glutamate release were shown to mediate delayed neurodegeneration via nitric oxide formation, see, e.g., Paul J. Strijbos et al, *Vicious Cycle Involving $Na^+$ Channels, Glutamate Release, and NMDA Receptors Mediates Delayed Neurodegeneration Through Nitric Oxide Formation*, 16(16) J. NEUROSCI. 5004-5013 (1996), which is hereby incorporated by reference in its entirety. It is thought that glutamate release requires the activation of voltage-gated $Na^+$ channels and therefore blocking these channels can prevent cytotoxic effects from excess spillover of glutamate. In a transgenic mouse model of ALS it was found that the morphological changes associated with neurogenenration in the peripheral axons of these mice were accompanied by changes in membrane conductance and excitability Jasna Kriz et al, *Altered Ionic Conductances in Axons Of Transgenic Mouse Expressing the Human Neurofilament Heavy Gene: A Mouse Model of Amyotrophic Lateral Sclerosis*, 163(2) EXP. NEUROL. 414-421 (2000). These authors suggested that the inactivation rate of the sodium channels from the axons of the transgenic mice were significantly slowed compared to controls. Moreover, of the many drugs tested for ALS the only drug shown to slow the progression of the disease (Riluzole) was found to block voltage-gated $Na^+$ channels and subsequent glutamate release, see, e.g., Alessandro Stefani et al., *Differential Inhibition by Riluzole, Lamotrigine, and Phenytoin of Sodium and Calcium Currents in Cortical Neurons: Implications for Neuroprotective Strategies*, 147(1) EXP. NEUROL. 115-122 (1997); and Thomas Anger et al., *Medicinal Chemistry of Neuronal Voltage-Gated Sodium Channel Blockers*, 44(2) J. MED. CHEM. 115-137 (2001), which are hereby incorporated by reference in their entirety. It was subsequently shown that Riluzole targets persistent sodium currents, see, e.g., Andrea Urbani & Ottorino Belluzzi, *Riluzole Inhibits the Persistent Sodium Current in Mammalian CNS Neurons*, 12(10) EUR. J. NEUROSCI. 3567-3574 (2000); and Francesca Spadoni et al., *Lamotrigine Derivatives and Riluzole Inhibit INa,P in Cortical Neurons*, 13(9) NEUROREPORT. 1167-1170 (2002), which are hereby incorporated by reference in their entirety. Thus persistent sodium currents appear to play a role in the progression of ALS, and selectively reducing this aberrantly high persistent sodium current can provide an effective means for treating an individual having ALS.

VI. Treatment of Ocular Conditions Using a Selective Persistent Sodium Current Antagonist The present invention also provides a method for treating an ocular condition by administering an effective amount of a selective persistent sodium current antagonist having at least 20-fold selectivity for persistent sodium current relative to transient sodium current. Unwanted neuronal firing and neuronal death induced by aberrant levels of persistent sodium channels can be a cause or contributing factor in ocular conditions.

An ocular condition can include a disease, aliment or condition which affects or involves the eye or one of the parts or regions of the eye. Broadly speaking the eye includes the eyeball and the tissues and fluids which constitute the eyeball, the periocular muscles (such as the oblique and rectus muscles) and the portion of the optic nerve which is within or adjacent to the eyeball. An anterior ocular condition is a disease, ailment or condition which affects or which involves an anterior (i.e. front of the eye) ocular region or site, such as a periocular muscle, an eye lid or an eye ball tissue or fluid which is located anterior to the posterior wall of the lens capsule or ciliary muscles. Thus, an anterior ocular condition primarily affects or involves, the conjunctiva, the cornea, the conjunctiva, the anterior chamber, the iris, the posterior chamber (behind the retina but in front of the posterior wall of the lens capsule), the lens or the lens capsule and blood vessels and nerve which vascularize or innervate an anterior ocular region or site. A posterior ocular condition is a disease, ailment or condition which primarily affects or involves a posterior ocular region or site such as choroid or sclera (in a position posterior to a plane through the posterior wall of the lens capsule), vitreous, vitreous chamber, retina, optic nerve (i.e. the optic disc), and blood vessels and nerves which vascularize or innervate a posterior ocular region or site.

Thus, a posterior ocular condition can include a disease, ailment or condition, such as for example, macular degeneration (such as non-exudative age related macular degeneration and exudative age related macular degeneration); choroidal neovascularization; acute macular neuroretinopathy; macular edema (such as cystoid macular edema and diabetic macular edema); Behcet's disease, retinal disorders, diabetic retinopathy (including proliferative diabetic retinopathy); retinal arterial occlusive disease; central retinal vein occlusion; uveitic retinal disease; retinal detachment; ocular trauma which affects a posterior ocular site or location; a posterior ocular condition caused by or influenced by an ocular laser treatment; posterior ocular conditions caused by or influenced by a photodynamic therapy; photocoagulation; radiation retinopathy; epiretinal membrane disorders; branch retinal vein occlusion; anterior ischemic optic neuropathy; non-retinopathy diabetic retinal dysfunction, retinitis pigmentosa and glaucoma. Glaucoma can be considered a posterior ocular condition because the therapeutic goal is to prevent the loss of or reduce the occurrence of loss of vision due to damage to or loss of retinal cells or optic nerve cells (i.e. neuroprotection).

An anterior ocular condition can include a disease, ailment or condition, such as for example, aphakia; pseudophakia; astigmatism; blepharospasm; cataract; conjunctival diseases; conjunctivitis; corneal diseases; corneal ulcer; dry eye syndromes; eyelid diseases; lacrimal apparatus diseases; lacrimal duct obstruction; myopia; presbyopia; pupil disorders; refractive disorders and strabismus. Glaucoma can also be considered to be an anterior ocular condition because a clinical goal of glaucoma treatment can be to reduce a hypertension of aqueous fluid in the anterior chamber of the eye (i.e. reduce intraocular pressure).

Examples of ocular conditions that can be treated using a method of the invention include, but are not limited to, maculopathies and retinal degeneration such as, e.g., Non-Exudative Age Related Macular Degeneration (ARMD), Exudative Age Related Macular Degeneration (ARMD), Choroidal Neovascularization, Diabetic Retinopathy, Central Serous Chorioretinopathy, Cystoid Macular Edema, Diabetic Macular Edema, Myopic Retinal Degeneration; retinal inflammatory diseases, such as, e.g., Acute Multifocal Placoid Pigment Epitheliopathy, Behcet's Disease, Birdshot Retinochoroidopathy, Infectious (Syphilis, Lyme, Tuberculosis, Toxoplasmosis), Intermediate Uveitis (Pars Planitis), Multifocal Choroiditis, Multiple Evanescent White Dot Syndrome (MEWDS), Ocular Sarcoidosis, Posterior Scleritis, Serpiginous Choroiditis, Subretinal Fibrosis and Uveitis Syndrome, Vogt-Koyanagi-Harada Syndrome, Punctate Inner Choroidopathy, Acute Posterior Multifocal Placoid Pigment Epitheliopathy, Acute Retinal Pigement Epitheliitis, Acute Macular Neuroretinopathy; retinal vascular and exudative diseases, such as, e.g., Diabetic retinopathy, Central Retinal Arterial Occlusive Disease, Central Retinal Vein Occlusion, Disseminated Intravascular Coagulopathy, Branch Retinal Vein Occlusion, Hypertensive Fundus Changes, Ocular Ischemic Syndrome, Retinal Arterial Microaneurysms, Coat's Disease, Parafoveal Telangiectasis, Hemi-Retinal Vein Occlusion, Papillophlebitis, Central Retinal Artery Occlusion, Branch Retinal Artery Occlusion, Carotid Artery Disease (CAD), Frosted Branch Angiitis, Sickle Cell Retinopathy and other Hemoglobinopathies, Angioid Streaks, Familial Exudative Vitreoretinopathy; Eales Disease; traumatic, surgical and environmental disorders, such as, e.g., Sympathetic Ophthalmia, Uveitic Retinal Disease, Retinal Detachment, Trauma, Retinal Laser, Photodynamic therapy, Photocoagulation, Hypoperfusion During Surgery, Radiation Retinopathy, Bone Marrow Transplant Retinopathy; proliferative disorders, such as, e.g., Proliferative Vitreal Retinopathy and Epiretinal Membranes; infectious disorders, such as, e.g., Ocular Histoplasmosis, Ocular Toxocariasis, Presumed Ocular Histoplasmosis Syndrome (POHS), Endophthalmitis, Toxoplasmosis, Retinal Diseases Associated with HIV Infection, Choroidal Disease Associate with HIV Infection, Uveitic Disease Associate with HIV Infection, Viral Retinitis, Acute Retinal Necrosis, Progressive Outer Retinal Necrosis, Fungal Retinal Diseases, Ocular Syphilis, Ocular Tuberculosis, Diffuse Unilateral Subacute Neuroretinitis, Myiasis; genetic disorders, such as. e.g., Retinitis Pigmentosa, Systemic Disorders with Accosiated Retinal Dystrophies, Congenital Stationary Night Blindness, Cone Dystrophies, Stargardt's Disease And Fundus Flavimaculatus, Best's Disease, Pattern Dystrophy of the Retinal Pigmented Epithelium, X-Linked Retinoschisis, Sorsby's Fundus Dystrophy, Benign Concentric Maculopathy, Bietti's Crystalline Dystrophy, pseudoxanthoma elasticum; optic neuropathies, such as, e.g., glaucoma; retinal injuries, such as, e.g., Macular Hole, Giant Retinal Tear; retinal tumors, such as, e.g., Retinal Disease Associated With Tumors, Congenital Hypertrophy Of The RPE, Posterior Uveal Melanoma, Choroidal Hemangioma, Choroidal Osteoma, Choroidal Metastasis, Combined Hamartoma of the Retina and Retinal Pigmented Epithelium, Retinoblastoma, Vasoproliferative Tumors of the Ocular Fundus, Retinal Astrocytoma, and Intraocular Lymphoid Tumors.

"Glaucoma" means primary, secondary and/or congenital glaucoma. Primary glaucoma can include open angle and closed angle glaucoma. Secondary glaucoma can occur as a complication of a variety of other conditions, such as injury, inflammation, vascular disease and diabetes.

VII. Neurological Conditions and Intracellular Nitric Oxide

The present invention further provides a method for treating a neurological condition associated with abnormal levels of nitric oxide by administering an effective amount of a selective persistent sodium current antagonist having at least 20-fold selectivity for persistent sodium current relative to transient sodium current. As disclosed herein, selective persistent sodium current antagonists are useful for selectively reducing persistent sodium current, thereby providing a neuroprotective benefit for acute and chronic neuronal insults. Such antagonists also are useful for reducing deleterious cellular effects resulting from inappropriately high levels of intracellular nitric oxide, and therefore, can effectively treat conditions characterized by aberrant levels of intracellular nitric oxide. As used herein, the term "condition characterized by aberrant levels of intracellular nitric oxide" means a disorder characterized by amounts of nitric oxide in the cells of an individual, that are increased compared to normal amounts of nitric oxide. Such excessive amounts of nitric oxide can result, for example, from excess or unregulated synthesis of nitric oxide.

Nitric oxide is a free radical gas that functions as a signaling molecule in at least three systems: white blood cells, where nitric oxide mediates tumoricidal and bactericidal effects; blood vessels, where it represents endothelium-derived relaxing factor activity, and in neurons, where it functions much like a neurotransmitter. In addition to its normal role in neurons, nitric oxide can also function as a neurotoxic mediator under pathophysiological conditions. For example, mice having a deletion of the nitric oxide synthase gene were found to be resistant to focal and transient global ischemia, see, e.g., Nariman Panahian et al., *Attenuated Hippocampal Damage After Global Cerebral schemia in Mice Mutant in Neuronal Nitric Oxide Synthase*, 72(2) NEUROSCIENCE 343-354 (1996), which is hereby incorporated by reference in its entirety. Therefore, without wishing to be bound by the following, nitric oxide can cause neuronal death by activating persistent sodium channels and causing intracellular calcium overload. As non-limiting examples, conditions characterized by aberrant levels of intracellular nitric oxide include vascular shock, stroke, diabetes, neurodegeneration, asthma, arthritis and chronic inflammation, see, e.g., Nobuyuki Miyasaka & Yukio Hirata, *Nitric Oxide and Inflammatory Arthritides*, 61(21) LIFE SCI. 2073-2081 (1997); Juan P. Bolanos & Ángeles Almeida, *Roles of Nitric Oxide in Brain Hypoxia-Ischemia*, 1411(2-3) BIOCHIM. BIOPHYS. ACTA. 415-436 (1999); Joel E. Barbato & Edith Tzeng *Nitric Oxide and Arterial Disease* 40(1) J. VASC. SURG. 187-193 (2004); Kevin J. Barnham at al., *Neurogegenerative diseases and Oxidative Stress*, 3(3) NAT. REV. DRUG. DIS. 205-214 (2004); Hossein A. Ghofrani et al., *Nitric Oxide Pathway and Phosphodiesterase Inhibitors in Pulmonary Arterial Hypertension*, 43(12 Suppl. S) J. AM. COLL. CARDIOL. 68S-72S (2004); Maria A. Moro et al., *Role of Nitric Oxide after Brain ischaemia*, 36(3-4) CELL CALCIUM 265-275 (2004); S A. Mulrennan & A. E. Redington, *Nitric Oxide Synthase Inhibition: Therapeutic Potential in Asthma*, 3(2) TREAT. RESPIR. MED. 79-88 (2004); Fabio L. M. Ricciardolo et al., *Nitric Oxide in Health and Disease of the Respiratory System*, 84(3) PHYSIOL. REV. 731-765 (2004); and Sharma S. Prabhakar, *Role of Nitric Oxide in Diabetic Nephropathy*, 24(4) SEMIN. NEPHROL. 333-344 (2004), which are hereby incorporated by reference in their entirety.

Nitric oxide can cause, neurodegeneration and neurotoxicity via voltage-gated sodium channels, see, e.g., Garthwaite et al, supra, (1999). For example in the optic nerve, the neurodestructive effects of nitric oxide donors were shown to be ameliorated by compounds that block voltage-gated $Na^+$ channels such as TTX, see, e.g., Gita Garthwaite et al, *Nitric Oxide Toxicity in CNS White Matter: An in Vitro Study Using Rat Optic Nerve*, 109(1) NEUROSCIENCE 145-155 (2000a); and Gita Garthwaite et al., *Soluble Guanylyl Cyclase Activator YC-1 Protects White Matter Axons From Nitric Oxide Toxicity and Metabolic Stress, Probably Through Na(+) Channel Inhibition*, 61 (1) MOL. PHARMACOL. 97-104 (2000b), which are hereby incorporated by reference in their entirety. Thus blocking voltage-gated $Na^+$ channels would appear to be a protective strategy against the injurious effects of nitric oxide toxicity. However, the normal rapidly inactivating $Na^+$ channels do not appear to be the targets for this strategy. For example, increases in either endogenous or exogenous levels of intracellular nitric oxide generate aberrant persistent sodium currents in central neurons and cardiac cells, see, e.g., Anna K. M. Hammarström & Peter W. Gage, *Nitric Oxide Increases Persistent Sodium Current in Rat Hippocampal Neurons*, 520(2) J. PHYSIOL. 451-461 (1999); and Gerard P. Ahern et al., *Induction of Persistent Sodium Current by Exogenous and Endogenous Nitric Oxide*, 275(37) J. BIOL. CHEM. 28810-28815 (2000), which are hereby incorporated by reference in their entirety. This up-regulation of persistent sodium current by nitric oxide is independent of guanylate cyclase and thus independent of cGMP formation, see, e.g., Ahern et al., supra, (2000). As such, nitric oxide may contribute to neurodestruction or neurodegeneration via activating or increasing persistent sodium current. Blocking persistent sodium current upregulated by nitric oxide should therefore prevent cellular $Na^+$ and subsequent $Ca^{2+}$ overload associated with neuronal cell death under pathophysiological conditions where this current plays a role. Thus blocking the persistent sodium current in neurons may afford a neuroprotective benefit in the treatment acute and chronic neuronal insults including neurodegenerative diseases where nitric oxide is thought to play a neurodestructive role.

An additional advantage of targeting the persistent sodium channel/current is that it appears to be the final common effector in the neurodestructive pathway caused by nitric oxide. For example, activation of NMDA receptors under excitotoxic conditions results in excess nitric oxide production, see, e.g., Strijbos et al, supra, (1996) that then up-regulates persistent sodium currents, see, e.g., Garthwaite et al, supra, (2000b). Activation of persistent sodium channels would then lead to further membrane depolarization (leading to further glutamate release), elevated intracellular $Ca^{2+}$ (via $Ca^{2+}$ influx through NMDA receptor channels) and reversal of the sodium/calcium exchanger. Elevation of $Ca^{2+}$ through the NMDA receptor and reverse sodium/calcium exchange would further exacerbate the situation since additional $Ca^{2+}$ entry would activate more nitric oxide synthase causing a pernicious cycle of neurodestruction.

It is understood that conditions characterized by aberrant levels of persistent sodium current or aberrant levels of intracellular nitric oxide can be identified or confirmed using routine methods, including methods described herein. It is also understood that one or more transient sodium currents also can be increased. Similarly, a level of intracellular nitric oxide in a cell from a subject having a disease or pathological condition can be compared to a level of intracellular nitric oxide in a cell from a normal or non-diseased subject. An increased level of intracellular nitric oxide can typically be observed in at least one cell type of a subject having a condition characterized by aberrant levels intracellular nitric oxide. Human conditions characterized by aberrant levels of persistent sodium current or aberrant levels of intracellular nitric oxide in addition to these described herein above can be identified by those skilled in the art.

VIII. Selective Persistent Sodium Current Blockers

The methods of the invention involve administering a compound that selectively reduces persistent sodium current relative to transient sodium current. As used herein, the term "selective," when used herein in reference to a compound, such as an antagonist, means a compound that, at least one particular dose reduces persistent sodium current at least 20-fold more than transient sodium current is reduced. Therefore, a compound that selectively reduces persistent sodium current has at least 20-fold selectively for persistent sodium current relative to transient sodium current, and can have, for example, at least 50-fold selectively for persistent sodium current relative to transient sodium current, at least 100-fold, at least 200-fold, at least 400-fold, at least 600-fold, or at least 1000-fold selectively for persistent sodium current relative to transient sodium current.

As used herein, the term "persistent sodium current" means a sodium channel mediated current that is non-transient; that can remain active during prolonged depolarization or that activates at voltage more negative than −60 mV and thus can contribute to hyperexcitability of the neural membrane. Prolonged depolarization refers to depolarization that occurs over a time period greater than the time period during which a transient current typically inactivates. As a non-limiting example, prolonged depolarization can occur within a time period greater than the time period during which the transient current of a sodium channel, such as $Na_v1.2$, typically inactivates. Therefore, prolonged depolarization refers to depolarization that persists for at least 0.002 second, such as at least 0.01 second, at least 0.1 second and at least 1 second.

A compound that selectively reduces persistent sodium current can be, for example, a persistent sodium channel antagonist. As used herein, the term "persistent sodium channel antagonist," means a compound that inhibits or decreases persistent current mediated through a sodium channel by binding to the sodium channel. It is understood that a persistent sodium channel antagonist can act by any antagonistic mechanism, such as by directly binding a persistent sodium channel at the pore entrance, thereby inhibiting movement of ions through the channel, or by binding a channel at another site to alter channel conformation and inhibit movement of ions through the channel. Exemplary selective persistent sodium channel antagonists that represent four structural classes of organic molecules are disclosed herein as Formulas 1, 2, 3 and 4.

It further is understood that a compound that selectively reduces persistent sodium current can act indirectly, for example, by reducing or down-regulating expression of a persistent sodium channel, for example, by inactivating a positive regulator of transcription or activating a negative regulator of transcription, without a corresponding reduction transient sodium channel; by increasing the expression or activity of a molecule that inactivates or reduces persistent sodium channel function, such as a protease, modifying enzyme or other molecule, without a corresponding reduction in transient sodium current; or by decreasing the expression or activity of a molecule that transmits a downstream signal from a persistent sodium current without a corresponding reduction in transient sodium current, for example, without substantially altering the downstream signal from a transient sodium channel.

As disclosed herein, structurally unrelated molecules can have at least 20-fold selectivity for reducing persistent sodium current relative to transient sodium current and, therefore, can be useful in the methods of the invention. For example, such a compound can be a naturally or non-naturally occurring macromolecule, such as a peptide, peptidomimetic, nucleic acid, carbohydrate or lipid. The compound further can be an antibody, or antigen-binding fragment thereof such as a monoclonal antibody, humanized antibody, chimeric antibody, minibody, bifunctional antibody, single chain antibody (scFv), variable region fragment (Fv or Fd), Fab or F(ab)$_2$. The compound also can be a partially or completely synthetic derivative, analog or mimetic of a naturally occurring macromolecule, or a small organic or inorganic molecule.

A selective persistent sodium current antagonist that is a nucleic acid can be, for example, an anti-sense nucleotide sequence, an RNA molecule, or an aptamer sequence. An anti-sense nucleotide sequence can bind to a nucleotide sequence within a cell and modulate the level of expression of a persistent, sodium channel gene, or modulate expression of another gene that controls the expression or activity of a persistent sodium channel. Similarly, an RNA molecule, such as a catalytic ribozyme, can bind to and alter the expression of a persistent sodium channel gene, or other gene that controls the expression or activity of a persistent sodium channel. An aptamer is a nucleic acid sequence that has a three dimensional structure capable of binding to a molecular target, see, e.g., Sumedha D. Jayasena, *Aptamers: An Emerging Class of Molecules That Rival Antibodies in Diagnostics*, 45(9) CLIN. CHEM. 1628-1650 (1999), which is hereby incorporated by reference in its entirety. As such, an aptamer can serve as a persistent sodium current selective compound.

A selective persistent sodium current antagonist that is a nucleic acid also can be a double-stranded RNA molecule for use in RNA interference methods. RNA interference (RNAi) is a process of sequence-specific gene silencing by post-transcriptional RNA degradation, which is initiated by double-stranded RNA (dsRNA) homologous in sequence to the silenced gene. A suitable double-stranded RNA (dsRNA) for RNAi contains sense and antisense strands of about 21 contiguous nucleotides corresponding to the gene to be targeted that form 19 RNA base pairs, leaving overhangs of two nucleotides at each 3' end (Sayda M. Elbashir et al., *Duplexes of 21-nucleotide RNAs Mediate RNA Interference in Cultured Mammalian Cells*, 411(6836) NATURE 494-498 (2001); B. L. Bass, *RNA Interference. The Short Answer*, 411(6836) NATURE 428-429 (2001); Phillip D. Zamore, *RNA Interference: Listening to the Sound of Silence*, 8(9) NAT. STRUCT. BIOL. 746-750 (2001), which are hereby incorporated by reference in their entirety. dsRNAs of about 25-30 nucleotides have also been used successfully for RNAi (Anton Karabinos et al., *Essential Roles for Four Cytoplasmic Intermediate Filament Proteins in Caenorhabditis elegans Development*, 98(14) PROC. NATL. ACAD. SCI. USA 7863-7868 (2001), which is hereby incorporated by reference in its entirety. dsRNA can be synthesized in vitro and introduced into a cell by methods known in the art.

A persistent sodium channel selective compound that is an antibody can be, for example, an antibody that binds to a persistent sodium channel and inhibits movement of ions through the channel, or alters the activity of a molecule that regulates persistent sodium current expression or activity, such that sodium current is decreased. It is understood that such a compound binds selectively such that a corresponding reduction in transient sodium current is not affected.

A persistent sodium channel selective compound that is a small molecule can have a variety of structures. In several embodiments, a compound that selectively reduces persistent sodium current that has at least 20-fold selectivity for reducing persistent sodium current to non-persistent sodium current is an organic molecule represented by a formula shown herein below, or a pharmaceutically acceptable salt, ester, amide, steroisomer or racemic mixture thereof. As disclosed herein in FIG. 1, several identified compounds are selective for persistent sodium current relative to transient sodium current, with selectivities of 32-fold, 38-fold, 110-fold and 453-fold. It is understood that these and other compounds with at least 20-fold selectivity for persistent sodium current relative to transient sodium current, for example, identified by the methods disclosed herein in Examples 1, 2, 3 and 4 can be useful for treating a neurological disorder according to a method of the invention.

In one embodiment, a compound useful in a method of the invention, or a pharmaceutically acceptable salt, ester, amide, stereoisomer or racemic mixture thereof, has a structure from Formula 1:

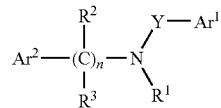

wherein,

Ar$^1$ is an aryl group;
Ar$^2$ is an aryl group;
Y is absent or is selected from:

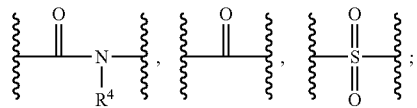

R$^1$ is selected from hydrogen, C$_1$-C$_8$ alkyl, aryl, or arylalkyl;

R$^2$ and R$^3$ are independently selected from hydrogen, C$_1$-C$_8$ alkyl, aryl, arylalkyl, hydroxy, fluoro, C$_1$-C$_8$ carbocyclic ring, or C$_1$-C$_8$ heterocyclic ring;

R$^4$ is selected from hydrogen, C$_1$-C$_8$ alkyl, aryl, or arylalkyl;

R$^5$ and R$^6$ are selected from hydrogen, fluoro, C$_1$ to C$_8$ alkyl, or hydroxy;

R$^7$ is selected from hydrogen, C$_1$ to C$_8$ alkyl, aryl, or arylalkyl, and n is an integer of from 1 to 6.

In one aspect of this embodiment, Ar$^1$ is thienyl, or substituted thienyl. For example, the thienyl can be substituted with one or more of halogen, C$_1$-C$_8$ alkyl, NO$_2$, CF$_3$, OCF$_3$, OCF$_2$H, CN, (CR$^5$R$^6$)$_c$N(R$^7$)$_2$, wherein c is 0 or an integer from 1 to 5; and In another aspect of this embodiment, Ar$^2$ is phenyl or substituted phenyl. For example, the phenyl can be substituted with halogen, C$_1$-C$_8$ alkyl, arylalkyl, NO$_2$, CF$_3$, OCF$_3$, OCF$_2$H, CN and (CR$^5$R$^6$)$_c$N(R$^7$)$_2$, wherein c is 0 or an integer from 1 to 5.

In another embodiment, a compound useful in a method of the invention, or a pharmaceutically acceptable salt, ester, amide, stereoisomer or racemic mixture thereof, has a structure from Formula 4:

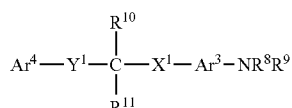

wherein,

Ar$^3$ is an aryl group;
Ar$^4$ is an aryl group;
X$^1$ and Y$^1$ are independently selected from:

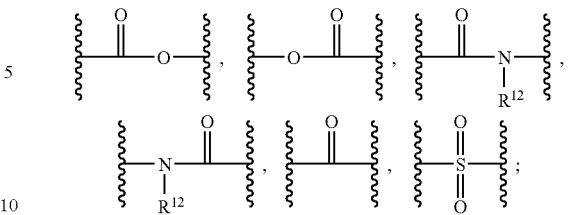

R$^5$ and R$^6$ are independently selected from: hydrogen, fluoro, C$_1$ to C$_8$ alkyl, hydroxy;

R$^7$ is selected from hydrogen, C$_1$ to C$_8$ alkyl, aryl, arylalkyl;

R$^8$ and R$^9$ are selected from hydrogen, C$_1$-C$_8$ alkyl, aryl, arylalkyl, COR$^{12}$, COCF$_3$;

R$^{10}$ and R$^{11}$ are selected from hydrogen, halogen, hydroxyl, C$_1$-C$_8$ alkyl, aryl, arylalkyl; and R$^{12}$ is selected from hydrogen, C$_1$-C$_8$ alkyl, aryl, arylalkyl.

In one aspect of this embodiment, Ar$^3$ can be phenyl or substituted phenyl. For example, the phenyl can be substituted with one or more of halogen, C$_1$-C$_8$ alkyl, NO$_2$, CF$_3$, OCF$_3$, OCF$_2$H, CN, (CR$^5$R$^6$)CN(R$^7$)$_2$, wherein c is 0 or an integer from 1 to 5.

In another aspect of this embodiment, Ar$^4$ is substituted with one or more of halogen, C$_1$-C$_8$ alkyl, arylalkyl, NO$_2$, CF$_3$, OCF$_3$, OCF$_2$H, CN or (CR$^5$R$^6$)$_c$N(R$^7$)$_2$, wherein c is 0 or an integer from 1 to 5.

In yet another embodiment, a compound useful in a method of the invention, or a pharmaceutically acceptable salt, ester, amide, stereoisomer or racemic mixture thereof, has a structure from Formula 2:

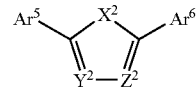

wherein,

Ar$^5$ is an aryl group;
Ar$^6$ is an aryl group;
X$^2$ is O, S, or NR$^{14}$;
Y$^2$ is N or CR$^{15}$;
Z$^2$ is N or CR$^{16}$;
R$^5$ and R$^6$ are selected from hydrogen, fluoro, C$_1$ to C$_8$ alkyl, hydroxy;

R$^7$ is selected from hydrogen, C$_1$ to C$_8$ alkyl, aryl, arylalkyl;

R$^{13}$ is selected from halogen, C$_1$-C$_8$ alkyl, arylalkyl, and (CR$^5$R$^6$)$_c$N(R$^7$)$_2$;

R$^{14}$ is selected from hydrogen, halogen, C$_1$ to C$_8$ alkyl, CF$_3$, OCH$_3$, NO$_2$, (CR$^5$R$^6$)$_c$N(R$^7$)$_2$;

R$^{15}$ is selected from hydrogen, halogen, C$_1$ to C$_8$ alkyl, CF$_3$, OCH$_3$, NO$_2$, (CR$^5$R$^6$)$_c$N(R$^7$)$_2$;

R$^{16}$ is selected from hydrogen, halogen, C$_1$ to C$_8$ alkyl, CF$_3$, OCH$_3$, NO$_2$, (CR$^5$R$^6$)$_c$N(R$^7$)$_2$, and wherein c is 0 or an integer from 1 to 5.

In one aspect of this embodiment, Ar$^5$ is phenyl or substituted phenyl. For example, the phenyl can be substituted with one or more of halogen, C$_1$-C$_8$ alkyl, NO$_2$, CF$_3$, OCF$_3$, OCF$_2$H, CN, or (CR$^5$R$^6$)$_c$N(R$^7$)$_2$, wherein c is 0 or an integer from 1 to 5.

In another aspect of this embodiment, $Ar^6$ is substituted with halogen, $C_1$-$C_8$ alkyl, arylalkyl, $NO_2$, $CF_3$, $OCF_3$, $OCF_2H$, CN or $(CR^5R^6)_cN(R^7)_2$, wherein c is 0 or an integer from 1 to 5.

In yet another aspect of this embodiment, $Ar^6$ is selected from:

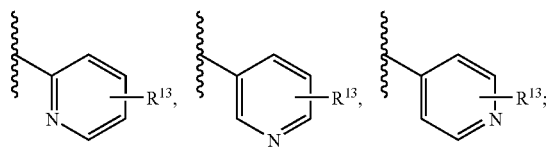

In yet another embodiment, a compound useful in a method of the invention, or a pharmaceutically acceptable salt, ester, amide, stereoisomer or racemic mixture thereof, has a structure from Formula 3:

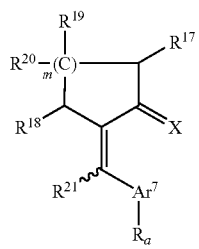

wherein,
$Ar^7$ is an aryl group;
$R_a$ is selected from halogen, $C_1$-$C_8$ alkyl, $NR^{22}R^{23}$, $OR^{22}$;
$R^5$ and $R^6$ are selected from hydrogen, fluoro, $C_1$ to $C_8$ alkyl, hydroxy;
$R^7$ is selected from hydrogen, $C_1$ to $C_8$ alkyl, aryl, arylalkyl;
$R^{17}$ and $R^{18}$ are independently selected hydrogen, $C_1$-$C_8$ alkyl, aryl, arylalkyl, and hydroxy;
$R^{19}$ and $R^{20}$ are independently selected from hydrogen, halogen, $C_1$-$C_8$ alkyl, hydroxy, amino, $CF_3$;
$R^{21}$, $R^{22}$, and $R^{23}$ are independently selected from hydrogen, aryl or $C_1$-$C_8$ alkyl;
a is 0 or an integer from, 1 to 5, and
m is 0 or and integer from 1 to 3.

In one aspect of this embodiment, $Ar^7$ is phenyl or substituted phenyl. For example the phenyl can be substituted with one or more of halogen, $C_1$-$C_8$ alkyl, $NO_2$, $CF_3$, $OCF_3$, $OCF_2H$, CN, $(CR^5R^6)_cN(R^7)_2$, wherein c is 0 or an integer from 1 to 5.

In another aspect of this embodiment, R is amino or

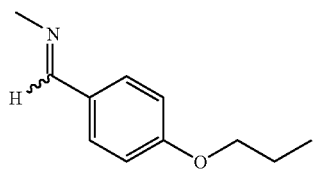

In yet another aspect of this embodiment, $R^{17}$ is isopropyl; in one embodiment, $R^{18}$ is methyl.

Exemplary compounds that are persistent sodium channel antagonists useful in a method of the invention are shown as Formulas 1, 2, 3 and 4. In addition, the compounds shown in FIG. 1 have selectivities for persistent sodium current of 32-fold, 38-fold, 110-fold, and 453-fold, relative to transient sodium current.

As used herein, the term "alkyl" means a straight-chain, branched or cyclic saturated aliphatic hydrocarbon. For example, an alkyl group can have 1 to 12 carbons, such as from 1 to 7 carbons, or from 1 to 4 carbons. Exemplary alkyl groups include methyl, ethyl, propyl, isopropyl, butyl, isobutyl, tertiary butyl, pentyl, hexyl and the like. An alkyl group may be optionally substituted with one or more substituents are selected from the group consisting of hydroxyl, cyano, alkoxy, =O, =S, $NO_2$, halogen, dimethyl amino, and SH.

As used herein, the term "alkenyl" means a straight-chain, branched or cyclic unsaturated hydrocarbon group containing at least one carbon-carbon double bond. For example, an alkenyl group can have 1 to 12 carbons, such as from 1 to 7 carbons, or from 1 to 4 carbons. An alkenyl group can optionally be substituted with one or more substituents. Exemplary substituents include hydroxyl, cyano, alkoxy, =O, =S, $NO_2$, halogen, dimethyl amino, and SH.

As used herein, the term "alkynyl" means a straight-chain, branched or cyclic unsaturated hydrocarbon containing at least one carbon-carbon triple bond. For example, an alkynyl group can have 1 to 12 carbons, such as from 1 to 7 carbons, or from 1 to 4 carbons. An alkynyl group can optionally be substituted With one or more substituents. Exemplary substituents include hydroxyl, cyano, alkoxy, =O, =S, $NO_2$, halogen, dimethyl amino, and SH.

As used herein, the term "alkoxyl" means an "O-alkyl" group.

As used herein, the term "aryl" means an aromatic group which has at least one ring having a conjugated pi electron system and includes carbocyclic aryl, heterocyclic aryl and biaryl groups. An aryl group can optionally be substituted with one or more subtituents. Exemplary substituents include halogen, trihalomethyl, hydroxyl, SH, OH, $NO_2$, amine, thioether, cyano, alkoxy, alkyl, and amino.

As used herein, the term "alkaryl" means an alkyl that is covalently joined to an aryl group. The alkyl can be, for example, a lower alkyl.

As used herein, the term "carbocyclic aryl" means an aryl group wherein the ring atoms are carbon.

As used herein, the term "heterocyclic aryl" means an aryl group having from 1 to 3 heteroatoms as ring atoms, the remainder of the ring atoms being carbon. Heteroatoms include oxygen, sulfur, and nitrogen. Thus, heterocyclic aryl groups include furanyl, thienyl, pyridyl, pyrrolyl, N-lower alkyl pyrrolo, pyrimidyl, pyrazinyl, imidazolyl and the like.

As used herein, the term "hydrocarbyl" means a hydrocarbon radical having only carbon and hydrogen atoms. For example, an hydrocarbyl radical can have from 1 to 20 carbon atoms, such as from 1 to 12 carbon atoms or from 1 to 7 carbon atoms.

As used herein, the term "substituted hydrocarbyl" means a hydrocarbyl radical wherein one or more, but not all, of the hydrogen and/or the carbon atoms are replaced by a halogen, nitrogen, oxygen, sulfur or phosphorus atom or a radical including a halogen, nitrogen, oxygen, sulfur or phosphorus atom, e.g. fluoro, chloro, cyano, nitro, hydroxyl, phosphate, thiol, etc.

As used herein, the term "amide" means —C(O)—NH—R', wherein R' is alkyl, aryl, alkylaryl or hydrogen. As used herein, the term "thioamide" means —C(S)—NH—R', wherein R' is alkyl, aryl, alkylaryl or hydrogen. As used herein, the term "amine" means a —N(R")R'" group, wherein R" and R'" are independently selected from the group consisting of alkyl, aryl, and alkylaryl. As used herein, the term "thioether" means —S—R", wherein R" is alkyl, aryl, or alkylaryl. As used herein, the term "sulfonyl" refers to —S(O)$_2$—R"", where R"" is aryl, C(CN)=C-aryl, CH$_2$CN, alkaryl, sulfonamide, NH-alkyl, NH-alkylaryl, or NH-aryl.

IX. Screening Assays

The ability of a compound to selectively reduce persistent sodium current relative to transient sodium current can be determined using a variety of assays. Such assays can be performed, for example, in a cell or tissue that expresses an endogenous or recombinantly expressed persistent sodium current, and generally involve determining persistent and transient sodium current prior to and following application of a test compound.

Methods for measuring sodium current are well known to those skilled in the art, and are described, see, e.g., Joseph S. Adorante, *Inhibition of Noninactivating Na Channels of Mammalian Optic Nerve as a Means of Preventing Optic Nerve Degeneration Associated with Glaucoma*, U.S. Pat. No. 5,922,746 (Jul. 13, 1999); Bert Sakmann & Erwin Neher, SINGLE CHANNEL RECORDING (Plenum Press, 2$^{nd}$ ed. 1995); and Tsung-Ming Shih et al., *High-level Expression and Detection of Ion Channels in Xenopus Oocytes*, 529-556 (METHODS IN ENZYMOLOGY: ION CHANNELS PART B, Vol. 293, P. Michael Conn ed., Academic Press 1998), which are hereby incorporated by reference in their entirety. These protocols are routine procedures well within the scope of one skilled in the art and from the teaching herein (see, e.g., Examples 1, 2, 3 and 4). Since the rate at which sodium currents open and close is rapid and the speed at which ions flow through the channel is high, channel function can be studied using an electrophysiological approach, which is capable of measuring the ion flux at the rate of one million ions per second with a millisecond time resolution. In addition, as shown in Examples 1, 2 and 3, a method for identifying a selective persistent sodium channel antagonist or other persistent sodium current antagonist can involve using a fluorescent dye that is sensitive to change in cell membrane potential in order to enable optical measurement of cell membrane potential. As disclosed herein below, a compound to be tested is added to a well containing cells that express a sodium channel capable of mediating a persistent sodium current, and express a potassium channel or a sodium/potassium ATPase or both.

Methods for measuring membrane potential with voltage-sensitive dyes are well known to those skilled in the art, and are described, see, e.g., Iain D. Johnson, *Fluorescent Probes for Living Cells* 30(3) HISTOCHEM. J. 123-140 (1998); and IMAGING NEURONS: A LABORATORY MANUAL (Rafael Yuste, et al., eds., Cold Spring Harbor Laboratory Press, 2000). In particular, the example listed below takes advantage of the high temporal and spatial resolution that derives from utilization of fluorescence resonance energy transfer (FRET) in the measurement of membrane potential by voltage-sensitive dyes as described, see, e.g., Jesus E. Gonzalez & Roger Y. Tsien, *Improved Indicators of Cell Membrane Potential That Use Fluorescence Resonance Energy Transfer* 4(4) CHEM. BIOL. 269-277 (1997); Roger Y. Tsien & Jesus E. Gonzalez, *Voltage Sensing by Fluorescence Resonance Energy Transfer*, U.S. Pat. No. 5,661,035 (Aug. 26, 1997); Roger Y. Tsien & Jesus E. Gonzalez, *Detection of Transmembrane Potentials by Optical Methods*, U.S. Pat. No. 6,342,379 (Jan. 29, 2002); Jesus E. Gonzalez & Michael P. Maher, *Cellular Fluorescent Indicators and Voltage/Ion Probe Reader (VIPR) Tools for Ion Channel and Receptor Drug Discovery*, 8(5-6) RECEPTORS CHANNELS 283-295, (2002); and Michael P. Maher & Jesus E. Gonzalez, *High Throughput Method and System for Screening Candidate Compounds for Activity Against Target Ion Channels*, U.S. Pat. No. 6,686,193 (Feb. 3, 2004), which are hereby incorporated by reference in their entirety.

In addition, the selectivity of a compound for persistent sodium current versus transient sodium current can be confirmed, as shown in the teaching herein (see, e.g., Examples 2 and 3).

A variety of cell types, including naturally occurring cells and genetically engineered cells can be used in an in vitro assay to detect persistent sodium current. Naturally occurring cells having non-inactivating sodium current include, for example, several types of neurons, such as squid axon, cerebellar Purkinje cells, neocortical pyramidal cells, thalamic neurons, CA1 hipppocampal pyramidal cells, striatal neurons and mammalian CNS axons. Other naturally occurring cells having persistent sodium current can be identified by those skilled in the art using methods disclosed herein below and other well known methods. Cells for use in testing a compound for its ability to alter persistent sodium current can be obtained from a mammal, such as a mouse, rat, pig, goat, monkey or human, or a non-mammal containing a cell expressing a sodium channel capable of mediating persistent sodium current.

Genetically engineered cells having persistent sodium current can contain, for example, a cDNA encoding a sodium channel capable of mediating a persistent current such as Na$_v$1.3; or can be a cell engineered to have increased expression of a sodium channel capable of mediating a persistent current, decreased expression of a sodium channel mediating a transient current, or both. Recombinant expression is advantageous in providing a higher level of expression of a sodium channel capable of mediating a persistent sodium current than is found endogenously and also allows expression in cells or extracts in which the channel is not normally found. One or more recombinant nucleic acid expression constructs generally contain a constitutive or inducible promoter of RNA transcription appropriate for the host cell or transcription-translation system, operatively linked to a nucleotide sequence that encodes one or more polypeptides of the channel of interest. The expression construct can be DNA or RNA, and optionally can be contained in a vector, such as a plasmid or viral vector. Based on well-known and publicly available knowledge of nucleic acid sequences encoding subunits of many sodium channels, including several sodium channels capable of mediating a persistent sodium current, one skilled in the art can express desired levels of a biologically active persistent or transient sodium channels using routine laboratory methods as described, see, e.g., Molecular Cloning A Laboratory Manual (Joseph Sambrook & David W. Russell eds., Cold Spring Harbor Laboratory Press, 3$^{rd}$ ed. 2001); and CURRENT PROTOCOLS IN MOLECULAR BIOLOGY (Frederick M. Ausubel et al., eds., John Wiley & Sons, 2004), which are hereby incorporated by reference in their entirety. cDNAs for several families of sodium channels have been cloned and sequenced, and are described, see, e.g, Alan L. Goldin, *Diversity of Mammalian Voltage-gated Sodium Channels*, 868 ANN. N.Y. ACAD. SCI. 38-50 (1999), William A. Catterall, *From Ionic Currents to Molecular Mechanisms: The Structure and Function of Voltage-gated Sodium Channels*, 26(1) NEURON 13-25 (2000); John N. Wood & Mark D. Baker, *Voltage-gated Sodium Channels*, 1(1) CURR. OPIN. PHARMACOL. 17-21 (2001); and Frank H. Yu & William A. Catterall, *Overview of the Voltage-Gated Sodium Channel Family*, 4(3) GENOME BIOL. 207 (2003), which are hereby incorporated by reference in their entirety. In addition, both nucleotide and protein sequences all currently described sodium channels are publicly available from the GenBank database (National Institutes of Health, National Library of Medicine, http://www.ncbi.nlm.nih.gov/), which is hereby incorporated by reference in its entirety.

Exemplary host cells that can be used to express recombinant sodium channels include isolated mammalian primary cells; established mammalian cell lines, such as COS, CHO, HeLa, NIH3T3, HEK 293-T and PC12; amphibian cells, such as *Xenopus* embryos and oocytes; and other vertebrate cells. Exemplary host cells also include insect cells such as *Drosophila*, yeast cells such as *S. cerevisiae, S. pombe*, or *Pichia pastoris* and prokaryotic cells (such as *E. coli*,) engineered to recombinantly express sodium channels.

X. Reaction Schemes

A compound used in a method of the invention can be synthesized by general synthetic methodology, such as by the specific synthetic reaction schemes and methodologies described below and in Examples 5, 6, 7 and 8. Modifications of these synthetic methodologies will become readily apparent to the practicing synthetic organic chemist in view of the following disclosure and general knowledge available in the art.

The reaction schemes disclosed below are directed to the synthesis of exemplary compounds used in a method of the invention. The synthetic processes described herein are adaptable within the skill of the practicing organic chemist and can be used with such adaptation for the synthesis of compounds useful in a method of the invention that are not specifically described. Reaction schemes 1, 2, 3 and 4 disclose synthetic routes to compounds having Formulas 1, 2, 3 and 4, respectively. Examples 5, 6, 7 and 8 describe methodology useful for synthesizing exemplary compounds representative of Formulas 1, 2, 3 and 4, respectively.

The specific reaction conditions described in Examples 5, 6, 7 and 8 are directed to the synthesis of exemplary compounds useful in a method of the invention. Whereas each of the specific and exemplary synthetic methods shown in Examples 5, 6, 7 and 8 describe specific compounds within the scope of general Formulas 1 through 4, the synthetic processes and methods used therein are adaptable within the skill of the practicing organic chemist and can be used with such adaptation for the synthesis of compounds useful in a method of the invention that are not specifically described herein as examples.

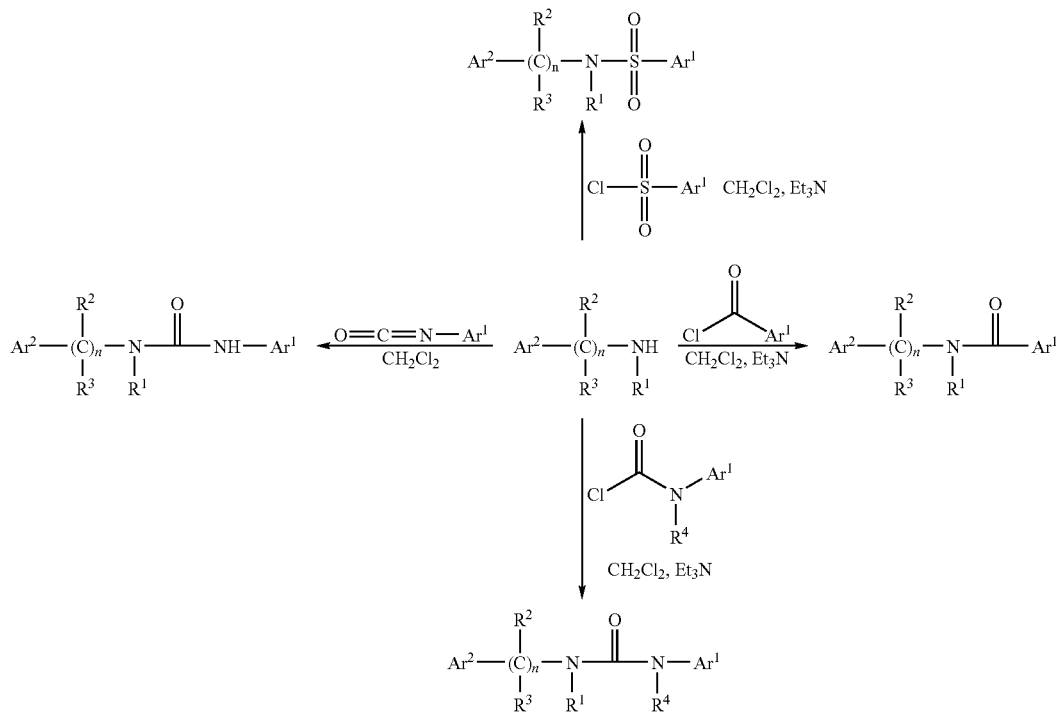

Reaction Scheme 1

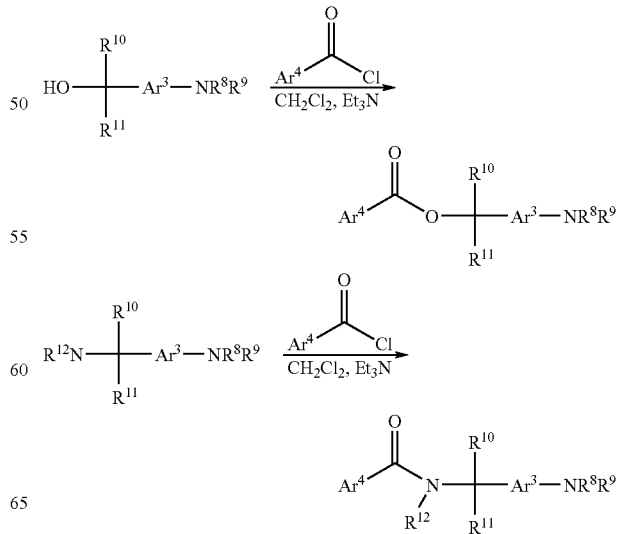

Reaction Scheme 2

-continued
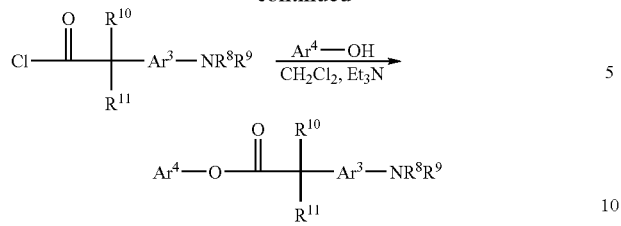
Reaction Scheme 3
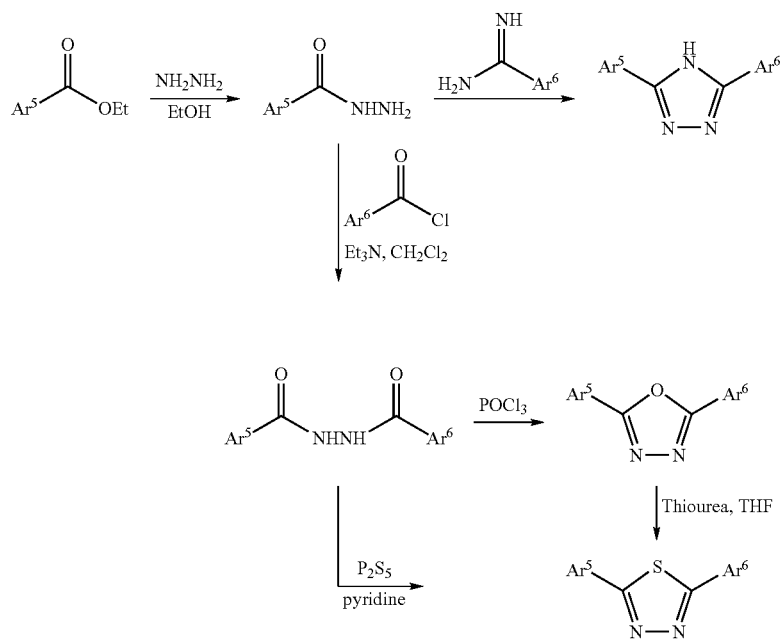
Reaction Scheme 4
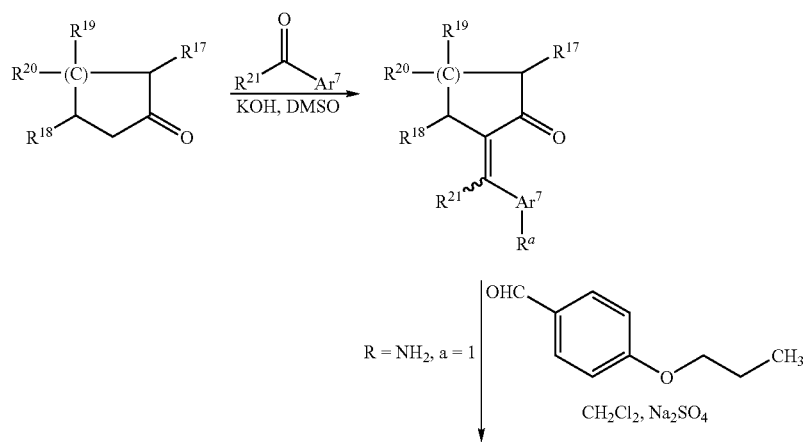

-continued

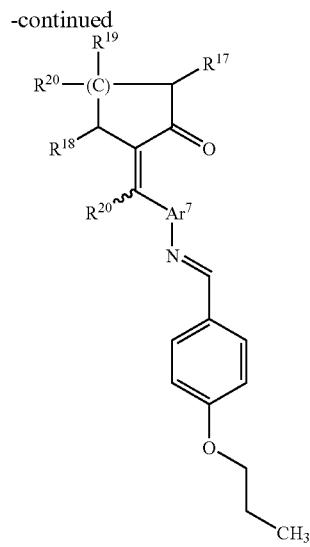

XI. Animal Models

The efficacy of a compound that selectively reduces persistent sodium current, such as a selective persistent sodium current antagonist, in treating a condition characterized by aberrant levels of sodium current or aberrant levels of intracellular nitric oxide in a mammal can be confirmed using a variety of well-known methods. Well-known animal models can be useful for determining the ability of a compound, such as a selective persistent sodium current antagonist, to reduce neuronal death or treat a condition characterized by aberrant levels of sodium current or condition characterized by aberrant levels of intracellular nitric oxide. Ischemia can be induced in several animal species using any of several surgical procedures, which can employ, for example, any of intralumenal occlusions, extralumenal occlusions, vascular clips, miniature hydraulic occluders or Ameroid occluders. Specific animal models of ischemia are well known to those skilled in the art, and exemplary ischemia models including rodent, monkey, baboon, dog, gerbil and rabbit models are described, see, e.g., Douglas E. McBean & Paul A. T. Kelly, *Rodent Models of Global Cerebral Ischemia: A Comparison of Two-Vessel Occlusion and Four-Vessel Occlusion* 30(4) GEN. PHARMACOL. 431-434 (1998); E. M. Nemoto, *Monkey Model of Complete Global Ischemia*, 24(2) STROKE 328-329 (1993); R. F. Spetzler et al., *Chronic Reversible Cerebral Ischemia: Evaluation of a New Baboon Model*, 7(3) NEUROSURGERY 257-261 (1980); A. Mitro et al., *Method of the Development of Irreversible, Complete Cerebral Ischemia in Dog*, 21(2) NEUROPATOL. POL. 315-321 (1983); T. Yoshimine & T Yanagihara, *Regional Cerebral Ischemia by Occlusion of the Posterior Communicating Artery and the Middle Cerebral Artery in Gerbils*, 58(3) J. NEUROSURG. 362-367 (1983); R. Pluta, *Experimental Treatment with Prostacyclin of Global Cerebral Ischemia in Rabbit-New Data*, 28(3-4) NEUROPATOL. POL. 205-215 (1990); J. Guo & Y. D. Chao, *Modification of a Model for Cerebral Ischemia in the Cat: A New Method to Occlude the Middle Cerebral Artery*, 25(1) NEUROSURGERY 49-53 (1989).

Animal models of neurodegenerative disorders are well known in the art, and include, for example, include Alzheimer's disease models, such as transgenic mice over-expressing mutant forms of amyloid precursor protein and presenilin-1, and models in which animals treated with amyloid β-peptide or excitotoxins. An exemplary model of Parkinson's disease involves administration of the toxin MPTP (1-methyl-4-phenyl-1,2,3,6-tetrahydropyridine) to animals, such as monkeys and mice, which results in selective loss of substantia nigra dopaminergic neurons and associated motor dysfunction. Neurodegenerative disease models can employ a variety of animals including, but not limited to, mice, gerbils, rats, rabbits, pigs, cats, dogs, sheep and primates, see, e.g., Senile Dementia of Alzheimer Type: Early Diagnosis, Neuropathology and Animal Models (J Traber & W. H. Gispen, eds., Springer Verlag, 1985); CENTRAL NERVOUS SYSTEM DISEASES: INNOVATIVE ANIMAL MODELS FROM LAB TO CLINIC (Dwaine F. Emerich et al., eds., Humana Press, 1999).

End-points useful for assessing the effect of a compound that selectively reduces persistent sodium current, such as a selective persistent sodium current antagonist, on the extent of neuronal death or dysfunction in comparison to a control animal that has not received the compound depend, in part, on the condition to be treated and are well known to those skilled in the art. Such end points included, for example, reduction in lesion size, improved physiological function, and improved behavior.

The activity of a compound that selectively reduces persistent sodium current, such as a selective persistent sodium current antagonist, also can be confirmed in a cell-based model of neuronal damage. Such a cell-based model can provide another read-out for the activity of an antagonist prior to its use in an animal model, and can also be used to identify antagonists or other compounds useful for reducing death of cultured neurons. Exemplary cell-based assays include cell models of ischemia-induced neuronal damage in which neurons demonstrate one or more indicia of apoptosis in response to a substance or condition, such as hypoxia, glucose deprivation, oxidative or excitotoxic insult. Exemplary cell-based models of ischemia-induced neuronal damage are known to those of skill in the art and are described, for example, in Lalitha Tenneti et al., *Role of Caspases in N-Methyl-D-Aspartate-Induced Apoptosis in Cerebrocortical Neurons*, 71(3) J. NEUROCHEM. 946-959 (1998); and R. James White & Ian J. Reynolds, *Mitochondrial Depolarization in Glutamate-Stimulated Neurons: An Early Signal Specific to Excitotoxin Exposure*, 16(18) J. NEUROSCI. 5688-5697 (1996).

The ability of a compound that selectively reduces persistent sodium current, such as a selective persistent sodium current antagonist, to reduce neuronal death or dysfunction can be assessed by analyzing an observable sign or symptom of nerve cell destruction in the presence and absence of treatment with the compound. Initiation of apoptotic death of neurons can have observable effects on cell function and morphology, as well as observable effects on tissues, organs and animals that contain dysfunctional or apoptotic neurons. Therefore, an indicator of neuronal damage can include observable parameters of molecular changes, such as increased expression of apoptosis-induced genes; cell function changes, such as reduced mitochondrial functions; cell morphological changes, such as cell shrinkage and blebbing; organ and tissue functional and morphological changes, such as the presence of an infarct or other lesion, the severity of which can be assessed by parameters including lesion volume and lesion size; physiological changes in animal models, including functional changes, such as loss of motor function, increased mortality and decreased survival, and behavioral changes, such as onset of dementia or loss of memory.

A reduction in an indicator of neuronal damage can be assessed in a cell, tissue, organ or animal by comparing an indicator of neuronal damage in at least two states of a cell, tissue, organ or animal. Thus, a reduction in an indicator of neuronal damage can be expressed relative to a control condition. A control condition can be, for example, a cell, tissue, organ or animal prior to treatment, in the absence of treatment, in the presence of a different treatment, in a normal animal or another condition determined to be appropriate by one skilled in the art.

XII. Pharmaceutical Compositions

As disclosed herein a selective persistent sodium current antagonist is administered to a mammal to treat a condition characterized by aberrant levels of sodium current or aberrant levels of intracellular nitric oxide. As used herein, the term "treating," when used in reference to administering to a mammal an effective amount of a selective persistent sodium current antagonist, means reducing a symptom of a condition characterized by aberrant levels of sodium current or aberrant levels of intracellular nitric oxide, or delaying or preventing onset of a symptom of a condition characterized by aberrant levels of sodium current or aberrant levels of intracellular nitric oxide in the mammal. For example, the term "treating" can mean reducing a symptom of a condition characterized by aberrant levels of sodium current or aberrant levels of intracellular nitric oxide by at least 30%, 40%, 60%, 70%, 80%, 90% or 100%. The effectiveness of a selective persistent sodium current antagonist in treating a condition characterized by aberrant levels of sodium current or aberrant levels of intracellular nitric oxide can be determined by observing one or more clinical symptoms or physiological indicators associated with the condition. An improvement in a condition characterized by aberrant levels of sodium current or aberrant levels of intracellular nitric oxide also can be indicated by a reduced need for a concurrent therapy. Those of skill in the art will know the appropriate symptoms or indicators associated with specific conditions and will know how to determine if an individual is a candidate for treatment with a selective persistent sodium current antagonist. In particular, it is understood that those skilled in the art will be able to determine if a condition if characterized by aberrant persistent sodium current, for example, by comparison of levels of persistent sodium channel expression or activity in cells from the individual with a normal control cells.

The appropriate effective amount to be administered for a particular application of the methods can be determined by those skilled in the art, using the guidance provided herein. For example, an effective amount can be extrapolated from in vitro and in vivo assays as described herein above. One skilled in the art will recognize that the condition of the patient can be monitored throughout the course of therapy and that the effective amount of a selective persistent sodium current antagonist that is administered can be adjusted accordingly.

The invention also can be practiced by administering an effective amount of persistent sodium current antagonist together with one or more other agents including, but not limited to, one or more analgesic agents. In such "combination" therapy, it is understood that the antagonist can be delivered independently or simultaneously, in the same or different pharmaceutical compositions, and by the same or different routes of administration as the one or more other agents.

Exemplary compounds that have at least 20-fold selectivity for reducing persistent sodium current relative to non-persistent sodium current include those shown in Formulas 1, 2, 3 and 4. Also encompassed by the invention are pharmaceutically acceptable salts, esters and amides derived from Formulas 1, 2, 3 or 4. Suitable pharmaceutically acceptable salts of the antagonists useful in the invention include, without limitation, acid addition salts, which can be formed, for example, by mixing a solution of the antagonist with a solution of an appropriate acid such as hydrochloric acid, sulfuric acid, fumaric acid, maleic acid, succinic acid, acetic acid, benzoic acid, citric acid, tartaric acid, carbonic acid or phosphoric acid. Where an antagonist carries an acidic moiety, suitable pharmaceutically acceptable salts thereof can include alkali salts such as sodium or potassium salts; alkaline earth salts such as calcium or magnesium salts; and salts formed with suitable organic ligands, for example, quaternary ammonium salts. Representative pharmaceutically acceptable salts include, yet are not limited to, acetate, benzenesulfonate, benzoate, bicarbonate, bisulfate, bitartrate, borate, bromide, calcium edetate, camsylate, carbonate, chloride, clavulanate, citrate, dihydrochloride, edetate, edisylate, estolate, esylate, fumarate, gluceptate, gluconate, glutamate, glycollylarsanilate, hexylresorcinate, hydrabamine, hydrobromide, hydrochloride, hydroxynaphthoate, iodide, isothionate, lactate, lactobionate, laurate, malate, maleate, mandelate, mesylate, methylbromide, methylnitrate, methylsulfate, mucate, napsylate, nitrate, N-methylglucamine ammonium salt, oleate, pamoate (embonate), palmitate, pantothenate, phosphate/diphosphate, polygalacturonate, salicylate, stearate, sulfate, subacetate, succinate, tannate, tartrate, teoclate, tosylate, triethiodide and valerate.

Thus, it is understood that the functional groups of antagonists useful in the invention can be modified to enhance the pharmacological utility of the compound. Such modifications are well within the knowledge of the skilled chemist and include, without limitation, esters, amides, ethers, N-oxides, and pro-drugs of the indicated antagonist. Examples of modifications that can enhance the activity of an antagonist include, for example, esterification such as the formation of C1 to C6 alkyl esters, such as C1 to C4 alkyl esters, wherein the alkyl group is a straight or branched chain. Other acceptable esters include, for example, C5 to C7 cycloalkyl esters and arylalkyl esters such as benzyl esters. Such esters can be prepared from the compounds described herein using conventional methods well known in the art of organic chemistry.

Other pharmaceutically acceptable modifications include the formation of amides. Useful amide modifications include, for example, those derived from ammonia; primary C1 to C6 dialkyl amines, where the alkyl groups are straight or branched chain; and arylamines having various substitutions.

In the case of secondary amines, the amine also can be in the form of a 5- or 6-member ring. Methods for preparing these and other amides are well known in the art.

It is understood that, where an antagonist useful in the invention has at least one chiral center, the antagonist can exist as chemically distinct enantiomers. In addition, where an antagonist has two or more chiral centers, the compound exists as diastereomers. All such isomers and mixtures thereof are encompassed within the scope of the indicated antagonist. Similarly, where an antagonist possesses a structural arrangement that permits the structure to exist as tautomers, such tautomers are encompassed within the scope of the indicated antagonist. Furthermore, in crystalline form, an antagonist can exist as polymorphs; in the presence of a solvent, an antagonist can form a solvate, for example, with water or a common organic solvent. Such polymorphs, hydrates and other solvates also are encompassed within the scope of the indicated antagonist as defined herein.

A selective persistent sodium current antagonist or other compound useful in the invention generally is administered in a pharmaceutical acceptable composition. As used herein, the term "pharmaceutically acceptable" refer to any molecular entity or composition that does not produce an adverse, allergic or other untoward or unwanted reaction when administered to a human or other mammal. As used herein, the term "pharmaceutically acceptable composition" refers to a therapeutically effective concentration of an active ingredient. A pharmaceutical composition may be administered to a patient alone, or in combination with other supplementary active ingredients, agents, drugs or hormones. The pharmaceutical compositions may be manufactured using any of a variety of processes, including, without limitation, conventional mixing, dissolving, granulating, dragee-making, levigating, emulsifying, encapsulating, entrapping, and lyophilizing. The pharmaceutical composition can take any of a variety of forms including, without limitation, a sterile solution, suspension, emulsion, lyophilizate, tablet, pill, pellet, capsule, powder, syrup, elixir or any other dosage form suitable for administration.

It is also envisioned that a pharmaceutical composition disclosed in the present specification can optionally include a pharmaceutically acceptable carriers that facilitate processing of an active ingredient into pharmaceutically acceptable compositions. As used herein, the term "pharmacologically acceptable carrier" refers to any carrier that has substantially no long term or permanent detrimental effect when administered and encompasses terms such as "pharmacologically acceptable vehicle, stabilizer, diluent, auxiliary or excipient." Such a carrier generally is mixed with an active compound, or permitted to dilute or enclose the active compound and can be a solid, semi-solid, or liquid agent. It is understood that the active ingredients can be soluble or can be delivered as a suspension in the desired carrier or diluent. Any of a variety of pharmaceutically acceptable carriers can be used including, without limitation, aqueous media such as, e.g., distilled, deionized water, saline; solvents; dispersion media; coatings; antibacterial and antifungal agents; isotonic and absorption delaying agents; or any other inactive ingredient. Selection of a pharmacologically acceptable carrier can depend on the mode of administration. Except insofar as any pharmacologically acceptable carrier is incompatible with the active ingredient, its use in pharmaceutically acceptable compositions is contemplated. Non-limiting examples of specific uses of such pharmaceutical carriers can be found in PHARMACEUTICAL DOSAGE FORMS AND DRUG DELIVERY SYSTEMS (Howard C. Ansel et al., eds., Lippincott Williams & Wilkins Publishers, 7$^{th}$ ed. 1999); REMINGTON: THE SCIENCE AND PRACTICE OF PHARMACY (Alfonso R. Gennaro ed., Lippincott, Williams & Wilkins, 20$^{th}$ ed. 2000); GOODMAN & GILMAN'S THE PHARMACOLOGICAL BASIS OF THERAPEUTICS (Joel G. Hardman et al., eds., McGraw-Hill Professional, 10$^{th}$ ed. 2001); and HANDBOOK OF PHARMACEUTICAL EXCIPIENTS (Raymond C. Rowe et al., APhA Publications, 4$^{th}$ edition 2003) which are hereby incorporated by reference in their entirety. These protocols are routine procedures and any modifications are well within the scope of one skilled in the art and from the teaching herein.

It is further envisioned that a pharmaceutical composition disclosed in the present specification can optionally include, without limitation, other pharmaceutically acceptable components, including, without limitation, buffers, preservatives, tonicity adjusters, salts, antioxidants, physiological substances, pharmacological substances, bulking agents, emulsifying agents, wetting agents, sweetening or flavoring agents, and the like. Various buffers and means for adjusting pH can be used to prepare a pharmaceutical composition disclosed in the present specification, provided that the resulting preparation is pharmaceutically acceptable. Such buffers include, without limitation, acetate buffers, citrate buffers, phosphate buffers, neutral buffered saline, phosphate buffered saline and borate buffers. It is understood that acids or bases can be used to adjust the pH of a composition as needed. Pharmaceutically acceptable antioxidants include, without limitation, sodium metabisulfite, sodium thiosulfate, acetylcysteine, butylated hydroxyanisole and butylated hydroxytoluene. Useful preservatives include, without limitation, benzalkonium chloride, chlorobutanol, thimerosal, phenylmercuric acetate, phenylmercuric nitrate and a stabilized oxy chloro composition, for example, PURITE®. Tonicity adjustors useful in a pharmaceutical composition include, without limitation, salts such as, e.g., sodium chloride, potassium chloride, mannitol or glycerin and other pharmaceutically acceptable tonicity adjustor. The pharmaceutical composition may be provided as a salt and can be formed with many acids, including but not limited to, hydrochloric, sulfuric, acetic, lactic, tartaric, malic, succinic, etc. Salts tend to be more soluble in aqueous or other protonic solvents than are the corresponding free base forms. It is understood that these and other substances known in the art of pharmacology can be included in a pharmaceutical composition useful in the invention.

An antagonist useful in a method of the invention is administered to a mammal in an effective amount. Such an effective amount generally is the minimum dose necessary to achieve the desired therapeutic effect, which can be, for example, that amount roughly necessary to reduce the symptoms associated with a neurological disorder, such as, e.g., epilepsy, cerebral hypoxia, cardiac ischemia, multiple sclerosis and amyotrophic lateral sclerosis. For example, the term "effective amount" when used with respect to treating a neurological disorder can be a dose sufficient to the symptoms, for example, by at least 30%, 40%, 50%, 60%, 70%, 80%, 90% or 100%. Such a dose generally is in the range of 0.1-1000 mg/day and can be, for example, in the range of 0.1-500 mg/day, 0.5-500 mg/day, 0.5-100 mg/day, 0.5-50 mg/day, 0.5-20 mg/day, 0.5-10 mg/day or 0.5-5 mg/day, with the actual amount to be administered determined by a physician taking into account the relevant circumstances including the severity of the neurological disorder, the age and weight of the patient, the patient's general physical condition, the cause of the neurological disorder and the route of administration. Where repeated administration is used, the frequency of administration depends, in part, on the half-life of the antagonist. Suppositories and extended release formulations can be useful in the invention and include, for example, dermal patches, formulations for deposit on or under the skin and formulations for intramuscular injection. It is understood that slow-release formulations also can be useful in the methods of the invention. The subject receiving the selective persistent sodium channel antagonist can be any mammal or other vertebrate capable of experiencing a neurological disorder, for example, a human, primate, horse, cow, dog, cat or bird.

Various routes of administration can be useful for treating a neurological disorder, such as, e.g., epilepsy, cerebral hypoxia, cardiac ischemia, multiple sclerosis and amyotrophic lateral sclerosis, according to a method of the invention. A pharmaceutical composition useful in the methods of the invention can be administered to a mammal by any of a variety of means depending, for example, on the type and location of a neurological disorder to be treated, the antagonist or other compound to be included in the composition, and the history, risk factors and symptoms of the subject. Routes of administration suitable for the methods of the invention include both systemic and local administration. As non-limiting examples, a pharmaceutical composition useful for treating a neurological disorder can be administered orally or by subcutaneous pump; by dermal patch; by intravenous, subcutaneous or intramuscular injection; by topical drops, creams, gels or ointments; as an implanted or injected extended release formulation; as a bioerodible or non-bioerodible delivery system; by subcutaneous minipump or other implanted device; by intrathecal pump or injection; or by epidural injection. An exemplary list of biodegradable polymers and methods of use are described in, e.g., Heller, *Biodegradable Polymers in Controlled Drug Delivery* (CRC CRITICAL REVIEWS IN THERAPEUTIC DRUG CARRIER SYSTEMS, Vol. 1. CRC Press, 1987); Vernon G. Wong, *Method for Reducing or Preventing Transplant Rejection in the Eye and Intraocular Implants for Use Therefor*, U.S. Pat. No. 6,699,493 (Mar. 2, 2004); Vernon G. Wong & Mae W. L. Hu, *Methods for Treating Inflammation-mediated Conditions of the Eye*, U.S. Pat. No. 6,726,918 (Apr. 27, 2004); David A. Weber et al., *Methods and Apparatus for Delivery of Ocular Implants*, U.S. Patent Publication No. US2004/0054374 (Mar. 18, 2004); Thierry Nivaggioli et al., *Biodegradable Ocular Implant*, U.S. Patent Publication No. US2004/0137059 (Jul. 15, 2004), which are hereby incorporated by reference in their entirety. It is understood that the frequency and duration of dosing will be dependent, in part, on the relief desired and the half-life of the selective persistent sodium current antagonist.

In particular embodiments, a method of the invention is practiced by peripheral administration of a selective persistent sodium current antagonist. As used herein, the term "peripheral administration" or "administered peripherally" means introducing an agent into a subject outside of the central nervous system. Peripheral administration encompasses any route of administration other than direct administration to the spine or brain. As such, it is clear that intrathecal and epidural administration as well as cranial injection or implantation are not within the scope of the term "peripheral administration" or "administered peripherally." It further is clear that some selective persistent sodium current antagonists can cross the blood-brain barrier and, thus, become distributed throughout the central and peripheral nervous systems following peripheral administration.

Peripheral administration can be local or systemic. Local administration results in significantly more of a pharmaceutical composition being delivered to and about the site of local administration than to regions distal to the site of administration. Systemic administration results in delivery of a pharmaceutical composition to essentially the entire peripheral nervous system of the subject and may also result in delivery to the central nervous system depending on the properties of the composition.

Routes of peripheral administration useful in the methods of the invention encompass, without limitation, oral administration, topical administration, intravenous or other injection, and implanted minipumps or other extended release devices or formulations. A pharmaceutical composition useful in the invention can be peripherally administered, for example, orally in any acceptable form such as in a tablet, liquid, capsule, powder, or the like; by intravenous, intraperitoneal, intramuscular, subcutaneous or parenteral injection; by transdermal diffusion or electrophoresis; topically in any acceptable form such as in drops, creams, gels or ointments; and by minipump or other implanted extended release device or formulation.

It is understood that modifications which do not substantially affect the activity of the various embodiments of this invention are also included within the definition of the invention provided herein. Accordingly, the following examples are intended to illustrate but not limit the present invention.

EXAMPLES

Example 1

High-throughput Screening Assay for Identification of Inhibitors of Persistent Sodium Current To identify compounds that inhibit persistent sodium current, a primary high-throughput screen was employed, see, e.g., Joseph S. Adorante et al., *High-throughput Screen for Identifying Channel Blockers that Selectively Distinguish Transient from Persistent Sodium Channels*, U.S. Patent Publication No. 2002/0077297 (Jun. 20, 2002), which is hereby incorporated by reference in its entirety.

I. Compound Identification Assay Overview

To examine the ability of test compounds to alter persistent sodium current, human embryonic kidney (HEK) cells were transfected with $Na_v1.3$ sodium channel to obtain cells that express sodium current capable of mediating persistent sodium current. HEK cells expressing $Na_v1.3$ (HEK-$Na_v1.3$) were added to assay plate wells containing a $Na^+$-free media and physiologic concentrations of K+ (4.5 mM) and preincubated for 20 minutes with ion-sensitive FRET dyes and either 5 µM of a test compound or a DMSO control. The assay plates were then transferred to a voltage/ion probe reader (VIPR) (Aurora Biosciences, San Diego, Calif.) and the VIPR was adjusted so that the fluorescent emission ratio from the donor ands acceptor FRET dyes equaled 1.0. To elicit persistent sodium current, a double addition protocol was performed by first adding an isotonic solution to adjust the concentration of sodium and potassium ions in the well to 110 mM and 10 mM, respectively, and measuring the resulting sodium-dependent depolarization and second by adding $K^+$ to a final concentration of 80 mM, and measuring potassium-dependent depolarization. Test compounds that block the $Na^+$ dependent signal, but not the $K^+$ dependent signal were selected for further analysis. The $Na^+$-dependent depolarization resulting from the persistent $Na^+$ was measured as shown in FIG. 2. The labeled boxes indicate the application of $Na^+$ or $K^+$. Circles indicate the control response with 0.1% DMSO added, triangles show the effects of the $Na^+$ channel inhibitor tetracaine (10 µM), and the diamonds show the response during the application of a non-specific channel blocker.

In this high-throughput assay, non-specific agents that inhibit membrane depolarizations induced by any effector must be distinguished from true persistent Na+ current antagonists, which block only Na+-dependent depolarizations. Therefore, a counter-screen to determine the ability of compounds to alter K+-dependent depolarization was performed. As shown in FIG. 2, following pre-incubation with vehicle alone (DMSO) both Na+ and K+ additions produced a robust depolarization as indicated by the increase in Rf/Ri. Tetracaine, a Na+ channel blocker, inhibited the Na+-dependent, but not the K+-dependent change in Rf/Ri. In contrast, a non-specific inhibitor of Na+ and K+-dependent depolarization blocked the change in Rf/Ri following either addition. This data demonstrates that selective antagonists of the persistent sodium current can be identified using the described method.

To eliminate compounds that non-specifically inhibited the Na+-dependent depolarization, data obtained using the above procedure was analyzed with respect to a counter-screen that used K+-dependent depolarization as a readout. To select hits from the primary screen, the data were plotted as histograms. Inhibition of the Na+-dependent depolarization was plotted against inhibition of the K+-dependent depolarization. Based on these data, the criteria for selection as a hit, was a greater or equal to 90% inhibition of the Na+-dependent depolarization and a less than or equal to 20% inhibition of the K+-dependent depolarization. This protocol provided a distinction between compounds that were inert or non-specific in their effects and compounds that specifically block the persistent sodium current.

II. Solutions

Solution compositions and volumes used in the assay are described below. Functions of some components of the solutions using the assay are as follows: (1) CC2-DMPE: a stationary coumarin-tagged phospholipid resonance energy donor. This dye is excited at 405 nm wavelength light and in the absence FRET emits fluorescence at 460 nm. (2) DiSBAC2(3) or DiSBAC6(3): mobile resonance energy acceptors that partition across the membrane as a function of the electric field. The excitation spectra for these dyes overlap the emission of the coumarin donor and, thus, they act as FRET acceptors. They have an emission spectrum in the range of 570 nm. (3) ESS-AY17: reduces the background fluorescence that complicates the assay. (4) $CdCl_2$ (400 μM) was included in the pre-incubation solutions to stabilize the membrane potential of the cells at negative resting potential, resulting in the maximum number of Na+ channels being available for activation. (5) Extracellular Cl— was replaced with $MeSO_3$ during preincubation and throughout the assay. This eliminates a complicating Cl— current during the assay and results in an amplified and more stable voltage-change induced by the persistent Na+ current. (6) 1st K+ addition: functions to depolarize the test cells to a voltage that activates substantial numbers of Na+ channels. (7) 2nd K+ addition: this addition produces a K+-dependent depolarization, which is used as a counterscreen to eliminated non-specific blockers.

III. Cell Culture

HEK-293 cells were grown in Minimum Essential Medium (Invitrogen, Inc., Carlsbad, Calif.) supplemented with 10% Fetal Bovine Serum (Invitrogen, Inc., Carlsbad, Calif.) and 1% Pennicillin-Streptomycin (Invitrogen, Inc., Carlsbad, Calif.). Medium for HEK-Na$_v$1.3 cells also contained 500 mg/ml G418 Geneticin (Invitrogen, Inc., Carlsbad, Calif.) and 2 μM TTX (Calbiochem, Inc., San Diego, Calif.) for maintaining selective pressure. Cells were grown in vented cap flasks, in 90% humidity and 10% CO2, to about 80% confluence and generally split by trypsinization 1:5 or 1:10.

HEK-Na$_v$1.3 cells were seeded in 96-well plates (Becton-Dickinson, San Diego, Calif.) coated with Matrigel (Becton-Dickinson, San Diego, Calif.) at 40,000 cells (in 100 μl culture medium) per well, and assayed the following day (16-20 hours). Cells were sometimes incubated in 96-well plates at somewhat lower densities (20,000 per well), and incubated for up to 40-48 hours.

IV. HEK-Na$_v$1.3 Handling and Dye Loading

Approximately 16 to 24 hours before the assay, HEK-Na$_v$1.3 cells were seeded in 96-well poly-lysine coated plates at 40,000 per well. On the day of the assay, medium was aspirated and cells were washed 3 times with 150 uL of Bath Solution #1 (BS#1) using CellWash (Thermo LabSystems, Franklin, Mass.).

A 20 μM CC2-DMPE solution was prepared by mixing coumarin stock solution with 10% Pluronic 127 1:1 and then dissolving the mix in the appropriate volume of BS#1. After the last wash, 50 ml of 20 μM CC2-DMPE solution was added to 50 mL of residual bath in each well to make 10 μM coumarin staining buffer. Plates were incubated in the dark for 30-60 minutes at room temperature.

While the cells were being stained with coumarin, a 10 μM DiSBAC2(3) solution in TEA-MeSO3 bath was prepared. In addition to oxonol, this solution contained any drug(s) being tested, at 4 times the desired final concentration (e.g. 20 μM for 5 μM final), 1.0 mM ESS-AY17, and 400 μM $CdCl_2$.

After 30-60 minutes of CC2-DMPE staining, the cells were washed 3 times with 150 μL of TEA-MeSO$_3$ buffer. Upon removing the bath, the cells were loaded with 80 μL of the DiSBAC2(3) solution and incubated for 20-30 minutes as before. Typically, wells in one column on each plate (e.g. column 11) were free of test drug(s) and served as positive and negative controls.

Once the incubation was complete, the cells were ready to be assayed on VIPR for sodium addback. 240 μL of NaMeSO3 buffer was added to stimulate the cells, resulting in a 1:4 dilution of the drugs; 240 μL of TEA-MeSO$_3$ buffer or 1 μM TTX was used as a positive control.

V. VIPR Instrumentation and Data Process

Optical experiments in microtiter plates were performed on the Voltage/ion Probe Reader (VIPR) using two 400 nm excitation filters and filter sticks with 460 nm and 570 nm filters on the emission side for the blue and red sensitive PMTs, respectively. The instrument was run in column acquisition mode with 2 or 5 Hz sampling and 30 seconds of recording per column. Starting volumes in each well were 80 ml; usually 240 mL was added to each well during the course of the experiment. The lamp was allowed to warm up for about 20 minutes, and power to the PMTs was turned on for about 10 minutes prior to each experiment.

Ratiometric measurements of changes in fluorescent emissions at 460- and 570 nm on the VIPR platform (Aurora Bioscience, San Diego, Calif.) demonstrated that this assay format produces a robust and reproducible fluorescent signal upon depolarization of HEK-Na$_v$1.3 cells with a Na+/K+ addition. From a normalized ratio of 1.0 in Na+-free media, Na+-dependent depolarization resulted in an increase in the 460/570 ratio to over 2.2 (FIG. 2). Inter-well analysis of the ratios indicated that the amplitude of signal was large enough and consistent enough to be used in high-throughput screening.

Data were analyzed and reported as normalized ratios of intensities measured in the 460 nm and 580 nm channels. The VIPR sampling rate varied between 2 and 5 Hz in different experiments, with 5 Hz used for higher resolution of the peak sodium responses. The process of calculating these ratios was performed as follows. On all plates, column 12 contained TEA-MeSO$_3$ buffer with the same DiSBAC2(3) and ESS-AY17 concentrations as used in the cell plates; however no cells were included in column 12. Intensity values at each wavelength were averaged for the duration of the scan. These average values were subtracted from intensity values in all assay wells. The initial ratio obtained from samples 5-10 (Ri) was defined as:

$$Ri = \frac{Intensity_{460nm,samples\ 5-10} - background_{460nm}}{Intensity_{580nm,samples\ 5-10} - background_{580nm}}$$

and the ratio obtained from sample f (Rf) was defined as:

$$Rf = \frac{Intensity_{460nm,samples\ f} - background_{460nm}}{Intensity_{580nm,samples\ f} - background_{580nm}}$$

Final data were normalized to the starting ratio of each well and reported as Rf/Ri. The fluorescent response in the Na$_v$1.3 persistent current assay reached a peak approximately 10 seconds following the start of the run, therefore, the maximum ratio was selected as the readout for the assay (FIG. 3).

VI. Assay Reproducibility and Resolution

The assay format described above allows for quality assurance by measuring both negative (DMSO 0.1%) and positive (tetracaine 10 µM) controls. Every 10th plate in an assay run was a control plate. The data from these plates were used to verify that the assay conditions were optimal and to normalize the data from the test compounds. FIG. 3 shows results from control plates from multiple assays.

Figure 3A:
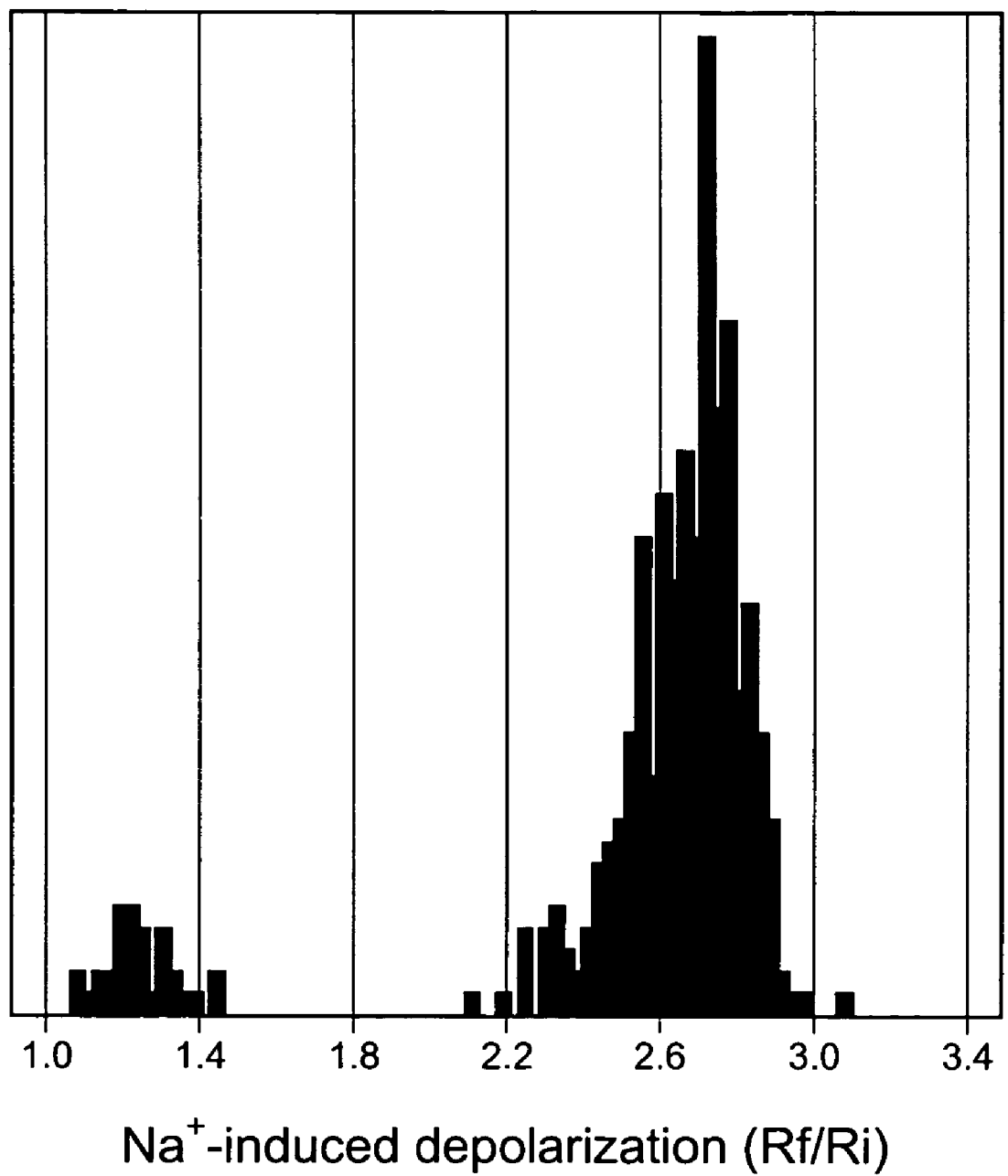
FIG. 3 shows data from assays in which the screening window for the persistent current assay is determined. To evaluate the size of the "screening window," data was examined from assays in which responses to sodium-dependent depolarization were measured in the presence of 10 µM Tetracaine to completely block the sodium-dependent depolarization or in the presence of a 0.1% DMSO control to obtain a maximum depolarization. Data were binned into histograms and a screening window (2) was calculated from the mean and standard deviation for the maximal and minimum values according to the equation: $Z=1-(3\times STD_{Max}+3\times STD_{Min})/(Mean_{Max}-Mean_{Min})$. Histograms A, B and C represent data obtained from three different assay plates. The screening window for a run was considered adequate $1.0 \geq Z \geq 0.5$.
Figure 3B:
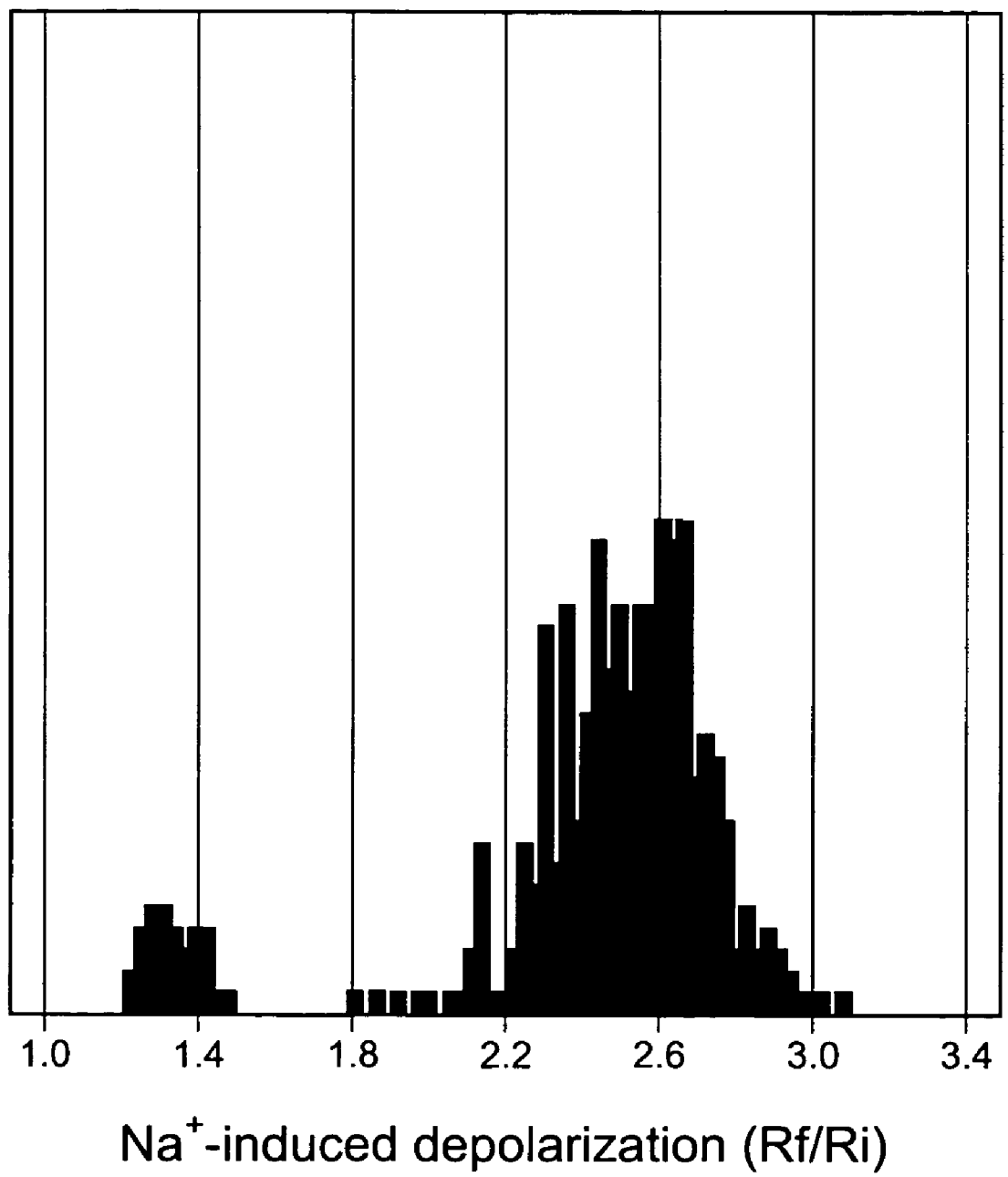
Figure 3C:
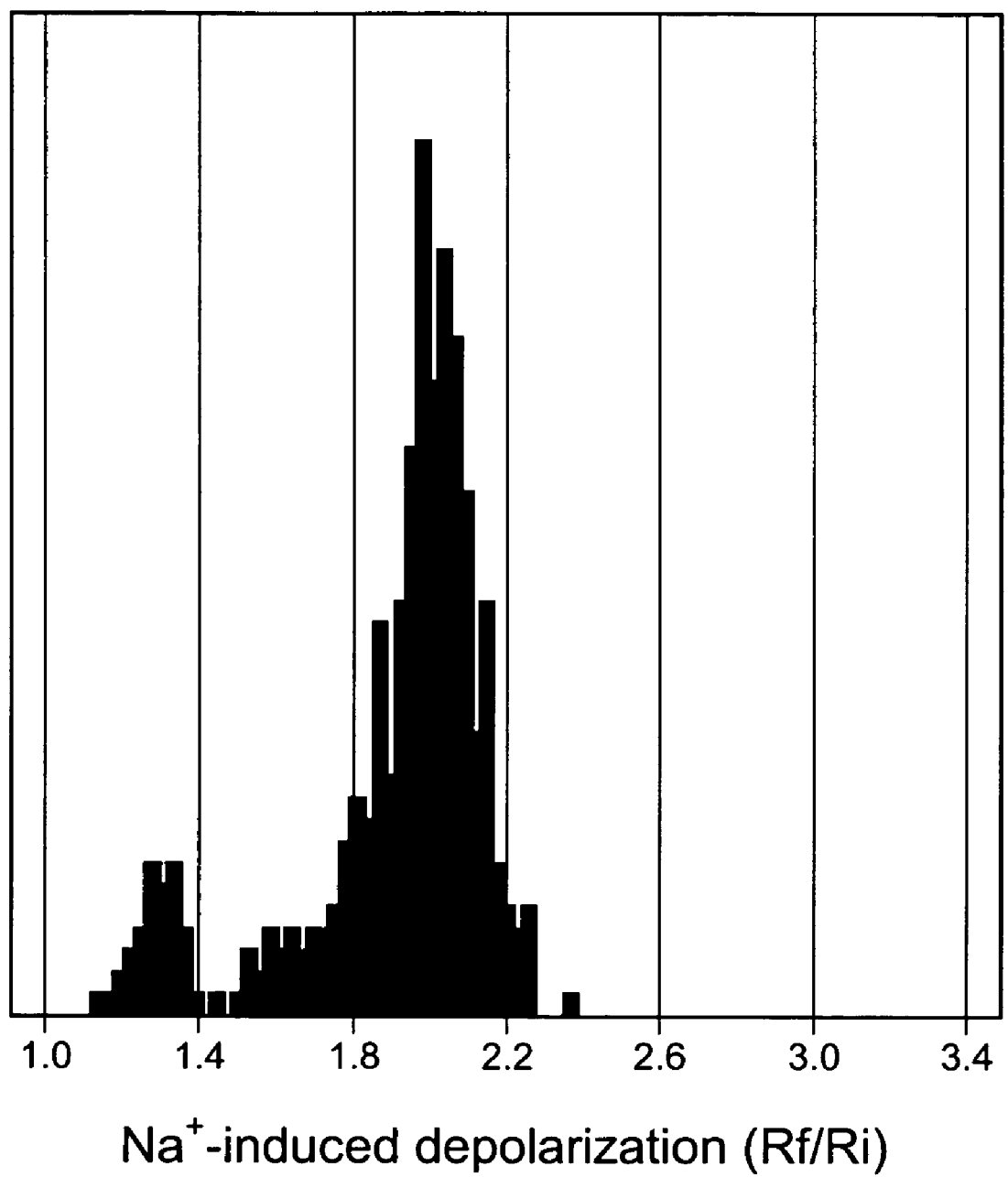

In FIG. 3, control plates having wells containing either 0.1% DMSO or 10 µM tetracaine were run after every ninth assay plate. The response to Na$^+$-dependent depolarization was measured and the data were binned into histograms as shown. The mean maximum response (Max) obtained in the presence of (0.1% DMSO) and the mean minimum response (Min) obtained in the presence of 10 µM tetracaine were determined. For quality control, data variance was compared to the difference between the maximum and minimum signals. This was accomplished by calculating a screening window (z) for each control plate. Data for the run was accepted if $1.0 \geq Z \geq 0.5$.

$$Z = 1 - \frac{3 \times STD_{max} + 3 \times STD_{min}}{Mean_{max} - Mean_{min}}$$

Example 2

Moderate-throughput Screening Assay for Selectivity of Inhibitors of Persistent Sodium Current Compounds obtained by the high-throughput screening described in Example 1 were tested for selectivity of blockade of persistent sodium current with respect to blockade of transient sodium current using a moderate-throughput screen. The selectivity assay utilizes Estim technology (Aurora Bioscience, San Diego, Calif.) to induce channel activation. This assay has an inherently greater time resolution than the high-throughput assay, and thus allows the measurement of both the transient and persistent components of the Na$^+$ currents within a single experiment.

I. Compound Selectivity Assay Overview

The Estim technology involves instrumenting 96-well plates with electrodes so that application of an appropriate voltage gradient across the well (electric field stimulation, EFS) can be used for activation of the ion channels in the target cells. EFS of HEK-293 cells expressing Na$_v$1.3 channels resulted in a rapid depolarization followed by a delayed repolarization. The transient Na$^+$ current drives the rapid depolarization while the persistent Na$^+$ current sustains the delayed repolarization. When similar experiments were performed in cells expressing channels that do not exhibit persistent currents, only rapid depolarization was seen. For quantification of the block of transient current, the amplitude of peak response was averaged for seven stimuli. The average response was converted to activity by normalizing against the difference between the responses in Ringer's solution with DMSO and Ringer's solution containing 10 µM tetracaine. Persistent current activity was calculated by integrating under the curve. The area obtained for each compound was normalized against the responses obtained with the DMSO control and in the presence of 10 µM tetracaine.

II. Cell Culture

Approximately 16 to 24 hours before the assay, HEK-Na$_v$1.3 cells were seeded in 96-well poly-lysine coated plates at 60,000 per well. On the day of the assay, medium was aspirated were cells were washed 3 times with 150 µL of HBSS using CellWash (Thermo LabSystems, Franklin, Mass.).

III. HEK-Na$_v$1.3 Handling and Dye Loading

A 20 µM CC2-DMPE solution was prepared by mixing coumarin stock solution with 10% Pluronic 127 1:1 and then dissolving the mix in the appropriate volume of HBSS. After the last wash, 50 µL of 20 µM CC2-DMPE solution was added to 50 µL of residual bath in each well to make 10 µM coumarin staining buffer. Plates were incubated in the dark for 30 minutes at room temperature.

While the cells were being stained with CC2-DMPE, a 0.2 µM DiSBAC6(3) solution in HBSS was prepared.

After 30 minutes of CC2-DMPE staining, the cells were washed 3 times with 150 µL of HBSS. After the last wash, 50 µL of 0.2 µM DiSBAC6(3) solution was added to 50 µL of residual bath in each well to make 0.1 µM oxonol staining buffer. Plates were then incubated in the dark for 15 minutes.

After 15 minutes of DiSBAC6(3) staining, the cells were washed again 3 times with 150 µL of HBSS. After the last wash, 50 µL of 1.0 µM ESS-AY17 solution was added to 50 µL of residual bath in each well to make 0.5 µM ESS. This solution also contained any drug(s) being tested, at twice the desired final concentrations. Plates were incubated in the dark again for 15 minutes. Once the incubation was complete, the cells were assayed on EFS/VSP reader.

III. Fast FRET Reader Instrumentation and Data Process

Optical experiments in microtiter plates were performed on the fast FRET Reader using two 400 nm excitation filters and filter sticks with 460 nm and 580 nm filters on the emission side for the blue and red sensitive PMTs, respectively. The instrument was run in column acquisition mode with 100 Hz sampling and 12 seconds of recording per column. Seven pulses were applied at 1 Hz, starting at 2 seconds. The lamp was allowed to warm up for about 20 minutes, and power to the PMTs was turned on for about 10 minutes prior to each experiment.

Data were analyzed and reported as normalized ratios of intensities measured in the 460 nm and 580 nm channels. The process of calculating these ratios was performed as follows. On all plates, column 12 contained. HBSS with the same ESS-AY17 concentration as used in the cell plates; however no cells were included in column 12. Intensity values at each wavelength were averaged for the duration of the scan. These average values were subtracted from intensity values in all assay wells. The initial ratio obtained from samples 50-100 (Ri) was defined as:

$$Ri = \frac{Intensity_{460nm, samples\ 50\text{-}100} - background_{460nm}}{Intensity_{580nm, samples\ 50\text{-}100} - background_{580nm}}$$

and the ratio obtained from sample f (Rf) was defined as:

$$Rf = \frac{Intensity_{460nm, samples\ f} - background_{460nm}}{Intensity_{580nm, samples\ f} - background_{580nm}}$$

Data were normalized to the starting ratio of each well and reported as Rf/Ri. The transient $Na^+$-current signal was calculated as average of the peaks resulting from the seven electric pulses applied in the course of recording. The persistent $Na^+$-current signal was calculated integrating the area under the total response during the seven electric pulses applied in the course of recording. Selectivity was determined by comparison of concentrations of agent required to block 50% of the persistent current ($IC_{50}$) vs. the $IC_{50}$ for the transient current.

Example 3

Electrophysiological Assay for Selectivity of Inhibitors of Persistent Sodium Current To confirm the blocking selectivity of test compounds for persistent sodium current, individual compounds were examined using a whole-cell patch clamp method.

HEK cells transfected with $Na_v1.3$ sodium channels that express transient and persistent sodium currents were plated onto glass coverslips and cultured in MEM cell culture media with Earle's salts and GlutaMAX (Invitrogen, Inc., Carlsbad, Calif.) supplemented with: 10% Fetal bovine serum, heat inactivated (Invitrogen, Inc., Carlsbad, Calif.), 0.1 mM MEM non-essential amino acids (Invitrogen, Inc., Carlsbad, Calif.), 10 mM HEPES (Invitrogen, Inc., Carlsbad, Calif.), 1% Penicillin/Streptomycin (Invitrogen, Inc., Carlsbad, Calif.).

After an incubation period of from 24 to 48 hours the culture medium was removed and replaced with external recording solution (see below). Whole cell patch clamp experiments were performed using an EPC10 amplifier (HEKA Instruments, Lambrecht, Germany.) linked to an IBM compatible personal computer equipped with PULSE software. Borosilicate glass patch pipettes were pulled to a fine tip on a P90 pipette puller (Sutter Instrument Co., Novato, Calif.) and were polished (Microforge, Narishige, Japan) to a resistance of about 1.5 Mohm when filled with intracellular recording solution (Table 1).

TABLE 1

| Patch Clamp Solutions | | | |
| --- | --- | --- | --- |
| External Recording Solution | | Internal Recording Solution | |
| Compound | Concentration | Compound | Concentration |
| NaCl | 127 mM | $CsMeSO_3$ | 125 mM |
| HEPES (free acid) | 10 mM | CsCl | 25 mM |
| KCl | 5 mM | NaHEPES | 10 mM |
| CsCl | 5 mM | Amphotericin | 240 µg/ml |
| Glucose | 10 mM | | |
| $MgCl_2$ | 0.6 mM | | |
| $CaCl_2$ | 1.2 mM | | |
| $CdCl_2$ | 200 µM | | |
| pH to 7.4 with NaOH @ room temp. 290 mOsm. | | pH 7.20 with CsOH 300 mOsm | |

Persistent and transient currents in HEK cells expressing $Na_v1.3$ channels were measured by applying 200-msec depolarizations from a holding potential of −90 mV to 0 mV. Background currents that remained in the presence of 500 nM TTX were subtracted from all traces. Drugs were perfused directly into the vicinity of the cells using a microperfusion system.

Figure 4:
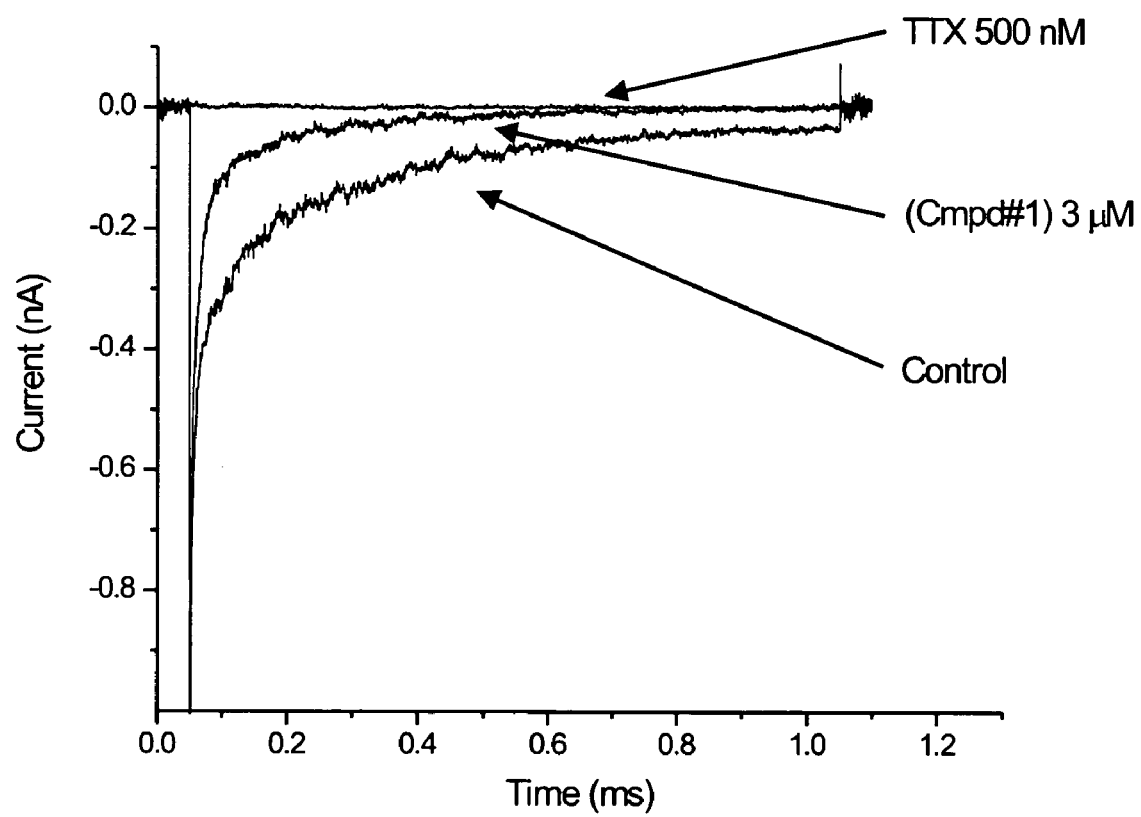
FIG. 4 shows sodium current traces before and after the addition of 3 µM Compound 1 or 500 nM TTX. HEK cells expressing $Na_v1.3$ channels were patch clamped in the perforated-patch mode. Currents were elicited by 200 msec test pulses to 0 mV from a holding potential of −90 mV.
Figure 5:
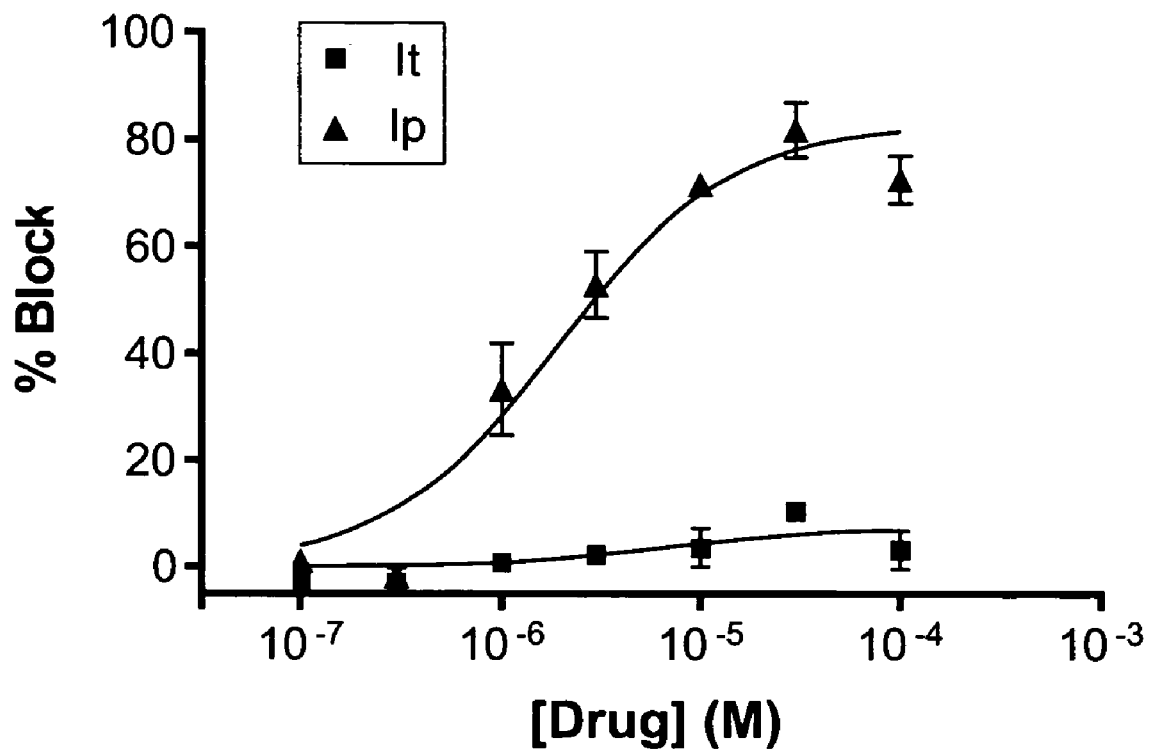
FIG. 5 shows a dose-response curve for Compound 1. The peak amplitudes of transient $Na^+$ current ($I_t$) and the steady state amplitude of the persistent current ($I_p$) were measured at various Compound 1 concentrations, normalized to amplitude of the control currents. The percent block was then plotted against drug concentration. Solid lines represent fits to the data with the Hill equation. The calculated $EC_{50}$ values and Hill coefficients are as follows: Hillslope, $I_t$ is 0.354 and $I_p$ is 0.733; $EC_{50}$, $I_t$ is 0.167 M and $I_p$ is $3.71\times10^{-6}$ M.

Under control conditions, depolarizing pulses elicited a large transient inward current that declined to a smaller persistent current, which remained stable during the remainder of the pulse (FIG. 4, control). Addition of 500 nM TTX completely blocked both the transient and persistent currents (FIG. 4, TTX). Application of 3 µM of Compound 1, produced a much different effect. Inspection of FIG. 4 reveals that the Compound 1 blocked 99% of the persistent current while only reducing the transient current by 16%. Dose-response analysis for Compound 1 demonstrates its significant selectivity for blocking the persistent sodium current relative to the transient sodium current over a four order of magnitude range (FIG. 5).

Example 4

Administering a Selective Persistent Sodium Current Antagonist in a Rodent Model Results in Reduced Epileptic Seizures This study examined the anti-seizure efficacy of Compound 1 against to reference compounds (Diazepam and Sipatrigine) using the audiogenic mouse model as the test platform.

DBA mice are well established in the literature as a model for audiogenic seizures (AGS). This genetically based model is attractive for testing potential therapeutics in that no treatment protocol is required to create the condition. It is classified as inherited idiopathic epilepsy with no known associated organic disease.

The AGS response in these mice consists of a progressive sequence of behaviors. The latency to onset may vary from 2 to 15 seconds, and is age variant. The initial wild running phase may be divided into an early running phase that varies from 5 tp 20 seconds, followed by a wild running phase that continues for 10-20 seconds. Wild running may progress to tonic/clonic seizures, with loss of righting ability, respiratory suppression and death.

We a scoring system to quantify the effects of the test compounds on the induction of seizures. The behavioral sequence was assigned ascending numerical values (Table 1), and the highest numerical value reached by an animal was that animal's score. Results are reported as an average score for ten animals in a treatment group.

TABLE 1

| | Seizure Scale |
|---|---|
| 1 | Staring |
| 2 | Head/body tremors/jerks |
| 3 | Tonic contraction/Straub tail |
| 4 | Wild running |
| 5 | Wild running/Jumping |
| 6 | Tonic Clonic Seizure |
| 7 | Convulsion |
| 8 | Death |

Animals. Male DBA/2 mice were obtained from Jackson Laboratories at 21 day post partum. The animals were acclimated for 1 or 2 days prior to use. Individual animal weights were recorded immediately before treatment. Surviving animals were euthanized within three days of completion of testing.

Seizure Induction. Mice were placed in a test chamber (25 cm i.d.) and exposed to pure tone sound of 11 kHz at a minimum of 116 dB for approximately 60 s until a sequential seizure response, consisting of an early wild running phase, followed by generalized myoclonus and tonic flexion and extension, was obtained. Non-responders were challenged up to five times. Ten animals were obtained by this method for each intended treatment group, with a standard deviation in their maximum score of less than 25%. The acoustic stimulus signal was produced using a signal generator and projected via four high-frequency ceramic speakers mounted on the roof of the chamber. Chamber calibration was performed daily to ensure consistent sound pressure. AGS behaviors were videotaped for later analysis.

I.P. injections: The 10 animals in each treatment group were injected intra-peritoneally with the test drug in a volume of 10 mL/kg of body weight. Injections were 60 min prior to sound challenge.

Data analyses: Data were tested for normal distribution, and (when normal) were analyzed using ANOVA followed by Student's t test. When the data were not normally distributed, analysis was with the Mann-Whitney rank sum test. Significance was set at $p<0.05$.

Results: Mean AGS scores for each group (with standard deviations) are shown for each treatment in Table 2. No control animals experienced full-blown convulsive seizures. Control values near five indicate that these animals entered the wild running phase and either did not progress to convulsions or exhibited infrequent or mild tonic-clonic seizures. Control animals exhibited tonic body contraction (back arching, hind leg rigidity), running and some body clonus (jerks, tremors). The response was quite variable with approximately 20% of the animals exhibiting very mild (if any) symptoms. No control animals developed powerful TCS symptoms that progressed to death.

Although the lack of a full-blown seizure response in the control animals limited the power of this study, compounds (Diazepam and Sipatrigine) that are known to reduce the behavioral response to sound-induced seizures in DBA mice were effective at the predicted doses. Compound 1 (1 mg/kg) also significantly reduced seizure response at 60 minutes after dosing. The estimated plasma concentration for Compound 1 at this time would be on approximately 5 µM, a concentration that should reduce the persistent sodium current by more than 60% while having only a limited effect on the transient current. The fact that statistically significant effects on seizure response were detected at this concentration in spite of both the high variability and the reduced therapeutic window in this assay indicates the efficacy of Compound 1 derives from its effect on the persistent sodium current. Table 2. Reduction of seizure score in DBA mice following treatment with potential anti-epileptic compounds.

TABLE 2

Reduction of seizure score in DBA mice following treatment with potential anti-epileptic compounds.

| Treatment | Dose (mg/kg) | Mean ± s.d. | p |
|---|---|---|---|
| Control | — | 4.8 ± 1.9 | |
| Diazepam | 0.15 | 3.1 ± 1.1 | 0.02 |
| Sipatrigine | 3 | 3.3 ± 1.7 | 0.04 |
| Compound 1 | 1 | 3.2 ± 2.3 | 0.04 |

Example 5

Synthesis of Exemplary Compounds Representative of Formula 1

A compound having general Formula 1, exemplified by thiophene-2-carboxylic acid (4-phenyl-butyl)-amide (Compound 1; FIG. 1) can be prepared as follows. A solution of thiophene-2-carbonyl chloride (147 mg, 1.0 mmol), triethylamine (101 mg, 1.0 mmol) in dichloromethane is treated with 4-phenylbutylamine (149 mg, 1.0 mmol). The reaction mixture is stirred until no further reaction occurs and is quenched by the addition of aqueous $NaHCO_3$ solution. The organic phase is collected and concentrated to give the title compound.

Example 6

Synthesis of Exemplary Compounds Representative of Formula 2

A compound having general Formula 2, exemplified by 1-Benzyl-4-(5-phenyl-[1,3,4]oxadiazol-2-yl)-pyridine (Compound 2; FIG. 1) can be prepared as follows. A solution of 4-(5-phenyl-[1,3,4]oxadiazol-2-yl)-pyridine (223 mg, 1.0 mmol) is prepared by the method of H. Smith Broadbent, et al., *Quinoxalines. I. Preparation and Stereochemistry of Decahydroquinoxalines*, 82(1) J. AMER. CHEM. SOC. 189-193 (1960) in chloroform is treated with benzylbromide (171 mg, 1.0 mmol). The reaction is stirred until no further reaction occurs. The reaction mixture is concentrated to give the title compound.

Example 7

Synthesis of Exemplary Compounds Representative of Formula 3

A compound having general Formula 3, exemplified by 6-Isopropyl-3-methyl-2-{4-[(4-propoxy-benzylidene)-amino]-benzylidene}-cyclohexanone (Compound 3; FIG. 1) can be prepared as follows. A solution of menthone (154 mg, 1.0 mmol) and 4-aminobenzaldehyde (121 mg, 1.0 mmol) in dimethylsulfoxide is treated with potassium hydroxide (56 mg, 1.0 mmol). The reaction is stirred until no futher reaction occurs. The reaction mixture is poured into ethyl acetate and water. The organic phase is collected, dried and concentrated to give 2-(4-Amino-benzylidene)-6-isopropyl-3-methyl-cyclohexanone. The 2-(4-Amino-benzylidene)-6-isopropyl-3-methyl-cyclohexanone is dissolved in dichloromethane and treated with 4-propoxybenzaldehyde (164 mg, 1.0 mmol) and anhydrous $Na_2SO_4$. The reaction mixture is stirred until no further reaction occurs. The reaction mixture is filtered and concentrated to give the title compound.

Example 8

Synthesis of Exemplary Compounds Representative of Formula 4

A compound having general Formula 4, exemplified by 3-(2,2,2-Trifluoro-acetylamino)-benzoic acid 2-oxo-2-phenyl-ethyl ester (Compound 4; FIG. 1) can be prepared as follows. A solution of 3-aminobenzoic acid (137 mg, 1.0 mmol) in dichloromethane is treated with trifluoroacetic anhydride (420 mg, 2.0 mmol). The reaction mixture is stirred until no further reaction occurs. The reaction mixture is concentrated to give 3-(2,2,2-Trifluoro-acetylamino)-benzoic acid. A solution of 3-(2,2,2-Trifluoro-acetylamino)-benzoic acid (233 mg, 1.0 mmol) and 2-hydroxyacetophenone (136 mg, 1.0 mmol) in dimethylformamide and diisopropylethylamine (260 mg, 2.0 mmol) is treated with HBTU (379 mg, 1.0 mmol). The reaction mixture is stirred until no further reaction occurs. The reaction is poured into ethyl acetate and water. The organic phase is collected, dried and concentrated to give the title compound.

Example 9

Oral Administration of a Persistent Sodium Current Blocker to Treat Epilepsy

This example shows a method of persistent sodium current blocker (PSCB) therapy using a pharmaceutically acceptable composition comprising a PSCB compound to treat a neuropathy. While the example illustrates the use of a PSCB to treat eplilepsy, any neuropathic condition resulting from aberrant activity of a persistent current, such as, e.g., headache, pain, inflammatory diseases, movement disorders, tumors, birth injuries, developmental abnormalities, neurocutaneous disorders, autonomic disorders, and paroxysmal disorders, can also be treated using this method.

A patient presents neuropathic symptoms that are diagnosed as an epilepsy. The patient is treated orally with a therapeutically-effective amount of a pharmaceutically acceptable composition comprising a PSCB over a period of several months. The patent is reassessed after this treatment and it is found that the patient's epileptic seizures have subside. Repeated administration of the PSCB composition maintains this sustained relief from epileptic seizures.

Example 10

Oral Administration of a Persistent Sodium Current Blocker to Treat Cerebral Hypoxia This example shows a method of persistent sodium current blocker (PSCB) therapy using a pharmaceutically acceptable composition comprising a PSCB compound to treat a hypoxia. While the example illustrates the use of a PSCB to treat cerebral hypoxia, any hypoxia resulting from a loss of oxygen to a portion of the body, such as, e.g., diffusion hypoxia, hypoxic hypoxia, cell hypoxia, ischemic hypoxia, or any other accidental or purposeful reduction or elimination of oxygen supply to a tissue, can also be treated using this method.

A patient presents symptoms that are diagnosed as cerebral hypoxia. The patient is treated orally with a therapeutically-effective amount of a pharmaceutically acceptable composition comprising a PSCB over a period of several months. The patent is reassessed after this treatment and it is found that the patient's symptoms have subside. Continued administration of the PSCB composition maintains alleviation of these symptoms.

Example 11

Oral Administration of a Persistent Sodium Current Blocker to Treat Cardiac Ischemia This example shows a method of persistent sodium current blocker (PSCB) therapy using a pharmaceutically acceptable composition comprising a PSCB compound to treat an ischemia. While the example illustrates the use of a PSCB to treat myocardiac ischemia, any ischemia resulting from a loss of blood to a portion of the body, such as, e.g., cerebral ischemia, myoischemia, diabetes ischemia, ischemia retinae, postural ischemia, or any other accidental or purposeful reduction or complete obstruction of blood supply to a tissue, can also be treated using this method.

A patient presents symptoms that are diagnosed as myocardiac ischemia. The patient is treated orally with a therapeutically-effective amount of a pharmaceutically acceptable composition comprising a PSCB over a period of several months. The patent is reassessed after this treatment and it is found that the patient's symptoms have subside. Continued administration of the PSCB composition maintains alleviation of these symptoms.

Example 12

Oral Administration of a Persistent Sodium Current Blocker to Treat Multiple Sclerosis This example shows a method of persistent sodium current blocker (PSCB) therapy using a pharmaceutically acceptable composition comprising a PSCB compound to treat multiple sclerosis.

A patient presents symptoms that are diagnosed as multiple sclerosis. The patient is treated orally with a therapeutically-effective amount of a pharmaceutically acceptable composition comprising a PSCB over a period of several months. The patent is reassessed after this treatment and it is found that the patient's symptoms have stablize. Continued administration of the PSCB composition maintains prevents continued progression of the disease.

Example 13

Oral Administration of a Persistent Sodium Current Blocker to Treat Amyotrophic Lateral Sclerosis This example shows a method of persistent sodium current blocker (PSCB) therapy using a pharmaceutically acceptable composition comprising a PSCB compound to treat amyotrophic lateral sclerosis.

A patient presents symptoms that are diagnosed as amyotrophic lateral sclerosis. The patient is treated orally with a therapeutically-effective amount of a pharmaceutically acceptable composition comprising a PSCB over a period of several months. The patent is reassessed after this treatment and it is found that the patient's symptoms have stablize.

Continued administration of the PSCB composition maintains prevents continued progression of the disease.

Example 14

Oral Administration of a Persistent Sodium Current Blocker to Treat Aberrant Nitric Oxide Levels This example shows a method of persistent sodium current blocker (PSCB) therapy using a pharmaceutically acceptable composition comprising a PSCB compound to treat aberrant nitric oxide levels.

A patient presents symptoms that are diagnosed as aberrant nitric oxide levels. The patient is treated orally with a therapeutically-effective amount of a pharmaceutically acceptable composition comprising a PSCB over a period of several months. The patent is reassessed after this treatment and it is found that the patient's symptoms have subside. Continued administration of the PSCB composition maintains alleviation of these symptoms.

Although the invention has been described with reference to the disclosed embodiments, those skilled in the art will readily appreciate that the specific experiments detailed are only illustrative of the invention. Various modifications can be made without departing from the spirit of the invention.

What is claimed:

1. A method of treating an epileptic condition in a mammal, comprising administering to said mammal an effective amount of a selective persistent sodium channel antagonist, wherein said antagonist has at least 20-fold selectivity for a persistent sodium current relative to a transient sodium current, and wherein said antagonist is a compound included in formula 4, or a pharmaceutically acceptable salt, ester, amide, stereoisomer or racemic mixture thereof:

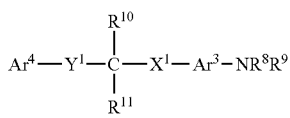

wherein,
  $Ar^3$ is phenyl or a substituted phenyl;
  $Ar^4$ is phenyl or a substituted phenyl;
  $X^1$ is absent or selected from the group consisting of

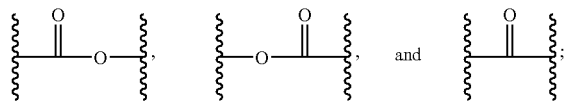

$Y^1$ is absent or selected from the group consisting of

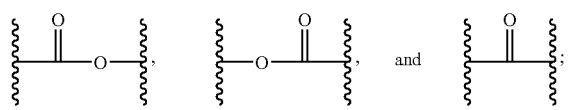

$R^8$ and $R^9$ are independently selected from the group consisting of hydrogen, $COCF_3$ and a $C_1$ to $C_8$ alkyl;
  $R^{10}$ and $R^{11}$ are independently selected from the group consisting of hydrogen, hydroxy, halogen, and a $C_1$ to $C_8$ alkyl.

2. The method of claim 1, wherein said persistent sodium current is $Na_v1.1$ persistent current.
3. The method of claim 1, wherein said persistent sodium current is $Na_v1.2$ persistent current.
4. The method of claim 1, wherein said persistent sodium current is $Na_v1.3$ persistent current.
5. The method of claim 1, wherein said persistent sodium current is $Na_v1.5$ persistent current.
6. The method of claim 1, wherein said persistent sodium current is $Na_v1.6$ persistent current.
7. The method of claim 1, wherein said persistent sodium current is $Na_v1.7$ persistent current.
8. The method of claim 1, wherein said persistent sodium current is $Na_v1.8$ persistent current.
9. The method of claim 1, wherein said persistent sodium current is $Na_v1.9$ persistent current.
10. The method of claim 1, wherein said mammal is a human.
11. The method of claim 1, wherein said antagonist has at least 50-fold selectivity for said persistent sodium current relative to said transient sodium current.
12. The method of claim 1, wherein said antagonist has at least 200-fold selectivity for said persistent sodium current relative to said transient sodium current.
13. The method of claim 1, wherein said antagonist has at least 400-fold selectivity for said persistent sodium current relative to said transient sodium current.
14. The method of claim 1, wherein said antagonist has at least 600-fold selectivity for said persistent sodium current relative to said transient sodium current.
15. The method of claim 1, wherein said antagonist has at least 1000-fold selectivity for said persistent sodium current relative to said transient sodium current.
16. The method of claim 1, wherein said antagonist is administered peripherally.
17. The method of claim 1, wherein said antagonist is administered systemically.
18. The method of claim 1, wherein said antagonist is administered orally.
19. The method of claim 1, wherein said antagonist is administered in a sustained release formula.
20. The method of claim 1, wherein said antagonist is administered in a bioerodible delivery system.
21. The method of claim 1, wherein said antagonist is administered in a non-bioerodible delivery system.
22. The method of claim 1, wherein said $Ar^3$ is phenyl.
23. The method of claim 1, wherein said $Ar^3$ is a substituted phenyl.
24. The method of claim 23, wherein said substituted phenyl is substituted with one or more of halogen, a $C_1$ to $C_8$ alkyl, $NO_2$, $CF_3$, $OCF_3$, $OCF_2H$, CN, or $(CR^5R^6)_cN(R^7)_2$
  wherein,
    $R^5$ and $R^6$ are independently selected from the group consisting of hydrogen, hydroxy, fluoro, and a $C_1$ to $C_8$ alkyl;
    $R^7$ is selected from the group consisting of hydrogen, and a $C_1$ to $C_8$ alkyl; and
    c is 0, 1, 2, 3, 4, or 5.
25. The method of claim 1, wherein said $Ar^4$ is phenyl.
26. The method of claim 1, wherein said $Ar^4$ is a substituted phenyl.
27. The method of claim 26, wherein said substituted phenyl is substituted with one or more of halogen, a $C_1$ to $C_8$ alkyl, $NO_2$, $CF_3$, $OCF_3$, $OCF_2H$, CN, or $(CR^5R^6)_cN(R^7)_2$ wherein,
R⁵ and R⁶ are independently selected from the group consisting of hydrogen, hydroxy, fluoro, and a $C_1$ to $C_8$ alkyl;
R⁷ is selected from the group consisting of hydrogen, and a $C_1$ to $C_8$ alkyl; and
c is 0, 1, 2, 3, 4, or 5.

28. The method of claim 1, wherein said R⁸ is hydrogen, methyl, ethyl, propyl, or isopropyl.

29. The method of claim 1, wherein said R⁹ is hydrogen, methyl, ethyl, propyl, or isopropyl.

30. The method of claim 1, wherein said R¹⁰ is hydrogen, methyl, ethyl, propyl, or isopropyl.

31. The method of claim 1, wherein said R¹¹ is hydrogen, methyl, ethyl, propyl, or isopropyl.

32. The method of claim 22, wherein said antagonist is 3-(2,2,2-Trifluoro-acetylamino)-benzoic acid 2-oxo-2-phenyl-ethyl ester.

33. The method of claim 25, wherein said antagonist is

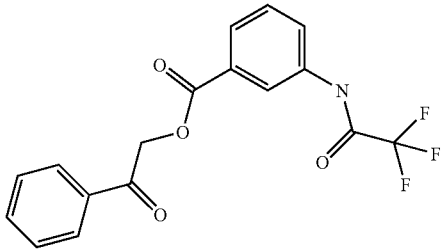

34. The method of claim 1, wherein said epileptic condition is a partial-onset seizure.

35. The method of claim 34, wherein said partial-onset seizure is selected from the group consisting of a simple partial seizure, a complex partial seizure and a secondarily generalized tonic-clonic seizure.

36. The method of claim 1, wherein said epileptic condition is a generalized-onset seizure.

37. The method of claim 36, wherein said generalized-onset seizure is selected from the group consisting of an absence seizure, a tonic seizure, a clonic seizure, a myoclonic seizure, a primary generalized tonic-clonic seizure, and an atonic seizure.

38. The method of claim 1, wherein said epileptic condition is an unclassified seizure.

39. The method of claim 1, wherein said epileptic condition is a localization-related syndrome.

40. The method of claim 1, wherein said epileptic condition is a generalized-onset syndrome.

41. The method of claim 1, wherein said epileptic condition is an inherited epileptic condition.

42. The method of claim 41, wherein said inherited epileptic condition is selected from the group consisting of an idiopathic epilepsy, a Severe Myoclonic Epilepsy in Infancy (SMEI), a Borderline SMEI (SMEB), and a Generalized Epilepsy with Febrile Seizures Plus (GEFS+).

43. The method of claim 1, wherein said effective amount reduces the symptoms of an epileptic condition by at least 30%.

44. The method of claim 1, wherein said effective amount reduces the symptoms of an epileptic condition by at least 50%.

45. The method of claim 1, wherein said effective amount reduces the symptoms of an epileptic condition by at least 70%.

46. The method of claim 1, wherein said effective amount reduces the symptoms of an epileptic condition by at least 90%.

* * * * *

UNITED STATES PATENT AND TRADEMARK OFFICE
CERTIFICATE OF CORRECTION

PATENT NO. : 7,728,034 B2 Page 1 of 5
APPLICATION NO. : 11/326264
DATED : June 1, 2010
INVENTOR(S) : George R. Ehring et al.

It is certified that error appears in the above-identified patent and that said Letters Patent is hereby corrected as shown below:

On the Title page, in field (56), in column 2, under "Other Publications", line 16, delete "Neurogegenerative" and insert -- Neurodegenerative --, therefor.

On the Title page, in field (56), in column 2, under "Other Publications", line 43, delete "Na+/Ca2+" and insert -- $Na^+/Ca^{2+}$ --, therefor.

Title page 2, in column 1, under "Other Publications", line 7, delete "Na+" and insert -- $Na^+$ --, therefor.

Title page 2, in column 1, under "Other Publications", line 21, delete "Na (+)" and insert -- $Na^{(+)}$ --, therefor.

Title page 2, in column 2, under "Other Publications", line 35, delete "Na+" and insert -- $Na^+$ --, therefor.

Title page 3, in column 1, under "Other Publications", line 6, delete "Ca2+" and insert -- $Ca^{2+}$ --, therefor.

Title page 3, in column 1, under "Other Publications", line 16, delete "Tubermammillary" and insert -- Tuberomammillary --, therefor.

In column 1, line 27, after "are" delete "a".

In column 3, line 54, delete "6;" and insert -- 6. --, therefor.

In column 4, line 19, delete "arylalkyl," and insert -- arylalkyl; --, therefor.

In column 4, line 21, delete "arylalkyl;" and insert -- arylalkyl. --, therefor.

In column 4, line 48, delete "5; and" and insert -- 5. --, therefor.

Signed and Sealed this

Tenth Day of August, 2010

David J. Kappos
*Director of the United States Patent and Trademark Office*

In column 5, line 13, delete "steroisomer," and insert -- stereoisomer, --, therefor.

In column 6, line 54, delete "Nav1.3, Nav1.5, Nav1.6 and Nav1.9," and insert -- $Na_v1.3$, $Na_v1.5$, $Na_v1.6$ and $Na_v1.9$, --, therefor.

In column 6, line 60, delete "Tubermammillary" and insert -- Tuberomammillary --, therefor.

In column 7, line 38, delete "$Ca2^+$" and insert -- $Ca^{2+}$ --, therefor.

In column 8, line 63-64, delete "used-herein," and insert -- used herein, --, therefor.

In column 9, line 26, delete "sporatic," and insert -- sporadic, --, therefor.

In column 9, line 42, delete "extrapyramidial" and insert -- extrapyramidal --, therefor.

In column 10, line 25, delete "$Na_v$ 1.2, $Na_v$ 1.3, $Na_v$ 1.5 and $Na_v$ 1.6," and insert -- $Na_v1.2$, $Na_v1.3$, $Na_v1.5$ and $Na_v1.6$, --, therefor.

In column 12, line 6, delete "tetrotoxin" and insert -- tetrodotoxin --, therefor.

In column 12, line 7, delete "extracelluar" and insert -- extracellular --, therefor.

In column 12, line 51, delete "tetrotoxin" and insert -- tetrodotoxin --, therefor.

In column 13, line 40, delete "ophthalmolscopic" and insert -- ophthalmoscopic --, therefor.

In column 13, line 41, delete "microaneruysms," and insert -- microaneurysms, --, therefor.

In column 13, line 57, delete "retinia," and insert -- retina, --, therefor.

In column 14, line 30, delete "sporatic" and insert -- sporadic --, therefor.

In column 15, line 54, delete "Ca2+" and insert -- $Ca^{2+}$ --, therefor.

In column 16, line 24, delete "neurogenenration" and insert -- neurodegeneration --, therefor.

In column 17, line 56, delete "degeneration" and insert -- degeneration, --, therefor.

In column 18, line 4, delete "Pigment Epitheliitis," and insert -- Pigment Epithelitis, --, therefor.

In column 18, line 33, delete "Accosiated" and insert -- Associated --, therefor.

In column 19, line 19, delete "schemia" and insert -- Ischemia --, therefor.

In column 19, line 35, delete "Neurogegenerative" and insert -- Neurodegenerative --, therefor.

In column 19, line 40, delete "ischemia," and insert -- Ischemia, --, therefor.

CERTIFICATE OF CORRECTION (continued)
U.S. Pat. No. 7,728,034 B2

In column 19, line 59, delete "Na(+)" and insert -- Na$^{(+)}$ --, therefor.

In column 22, line 58, delete "steroisomer" and insert -- stereoisomer --, therefor.

In column 23, line 36-37, delete "arylalkyl," and insert -- arylalkyl; --, therefor.

In column 23, line 44, delete "5; and" and insert -- 5. --, therefor.

In column 24, line 25, delete "(CR$^5$R$^6$)CN(R$^7$)$_2$," and insert -- (CR$^5$R$^6$)$_c$N(R$^7$)$_2$, --, therefor.

In column 24, line 61, delete "(CR$^5$R$^6$)$_c$N(R$^7$)$_2$, and" and insert -- (CR$^5$R$^6$)$_c$N(R$^7$)$_2$; and --, therefor.

In column 25, line 57, after " 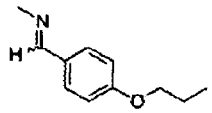 " insert -- ; --.

In column 26, line 26, delete "With" and insert -- with --, therefor.

In column 26, line 35, delete "subtituents." and insert -- substituents. --, therefor.

In column 27, line 4, delete "alkyaryl," and insert -- alkylaryl, --, therefor.

In column 27, line 29, delete "flow," and insert -- flow --, therefor.

In column 28, line 14, delete "hipppocampal" and insert -- hippocampal --, therefor.

In column 28, line 55, delete "e.g," and insert -- e.g., --, therefor.

In column 33-34, line 1, delete " 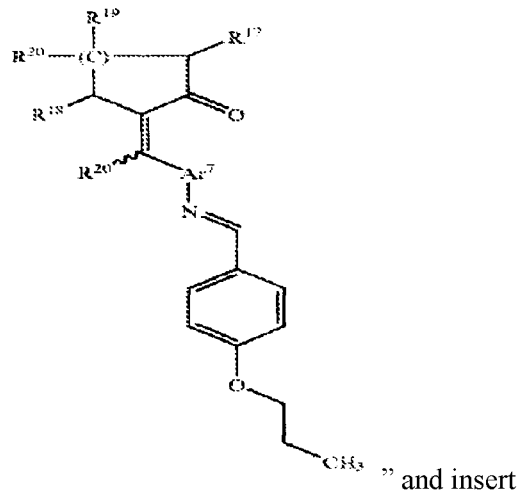 " and insert

CERTIFICATE OF CORRECTION (continued)
U.S. Pat. No. 7,728,034 B2

-- 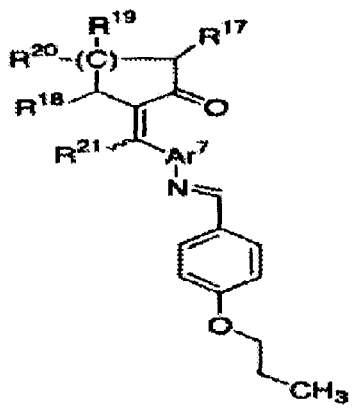 --, therefor.

In column 36, line 41, delete "isothionate," and insert -- isethionate, --, therefor.

In column 41, line 60, delete "Pennicillin-" and insert -- Penicillin- --, therefor.

In column 42, line 23, delete "TEA-MeSO3" and insert -- TEA-MeSO$_3$ --, therefor.

In column 42, line 36, delete "NaMeSO3" and insert -- NaMeSO$_3$ --, therefor.

In column 42, line 41, delete "Voltage/ion" and insert -- Voltage/Ion --, therefor.

In column 46, line 58, delete "tp" and insert -- to --, therefor.

In column 46, line 62, delete "We" and insert -- We used --, therefor.

In column 47, line 13, delete "Animals." and insert -- Animals: --, therefor.

In column 47, line 19, delete "Seizure Induction." and insert -- Seizure Induction: --, therefor.

In column 48, line 2-4, after "sodium current." delete "Table 2. Reduction of seizure score in DBA mice following treatment with potential anti-epileptic compounds.".

In column 48, line 62, delete "futher" and insert -- further --, therefor.

In column 49, line 37, delete "eplilepsy," and insert -- epilepsy, --, therefor.

In column 50, line 49, delete "stablize." and insert -- stabilize. --, therefor.

In column 50, line 67, delete "stablize." and insert -- stabilize. --, therefor.

In column 53, line 17, in claim 32, delete "acetylamino) -benzoic" and insert -- acetylamino)-benzoic --, therefor.

CERTIFICATE OF CORRECTION (continued)
U.S. Pat. No. 7,728,034 B2

In column 53, line 25, in claim 33, after " 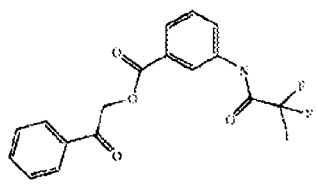 " insert -- . --.